US 6,551,334 B2

(12) United States Patent
Blatter et al.

(10) Patent No.: US 6,551,334 B2
(45) Date of Patent: *Apr. 22, 2003

(54) EXTERNALLY DIRECTED ANASTOMOSIS SYSTEMS AND EXTERNALLY POSITIONED ANASTOMOSIS FENESTRA CUTTING APPARATUS

(75) Inventors: Duane D. Blatter; Kenneth C. Goodrich, both of Salt Lake City; Mike C. Barrus, Bountiful; Bruce M. Burnett, Salt Lake City; Nemo J. Tullius, Jr., Tayorsville, all of UT (US)

(73) Assignee: Integrated Vascular Interventional Technologies, LC, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/736,781

(22) Filed: Dec. 14, 2000

(65) Prior Publication Data

US 2001/0016749 A1 Aug. 23, 2001

Related U.S. Application Data

(63) Continuation-in-part of application No. 09/460,740, filed on Dec. 14, 1999, and a continuation-in-part of application No. 09/293,366, filed on Apr. 16, 1999.

(51) Int. Cl.[7] ............................................. A61B 17/32
(52) U.S. Cl. ..................... 606/153; 606/170; 606/184; 600/567
(58) Field of Search ................... 606/149, 150, 606/151, 153, 159, 167, 170, 184; 600/566, 567; 128/898

(56) References Cited

U.S. PATENT DOCUMENTS 1,052,374 A    2/1913  Parr
2,192,699 A    4/1940  Storz (List continued on next page.)

FOREIGN PATENT DOCUMENTS

| WO | WO 93/00868 | 1/1993 | ............. A61F/2/06 |
| WO | WO 97/12555 | 4/1997 | ............. A61B/17/11 |
| WO | WO 98/06356 | 2/1998 | ............. A61F/2/06 |
| WO | WO 98/19629 | 5/1998 | ............. A61F/2/06 |
| WO | WO 98/19634 | 5/1998 | ............. A61F/2/06 |
| WO | WO 99/11180 | 3/1999 | ............. A61B/17/11 |

OTHER PUBLICATIONS

Bass, Lawrence S. MD, and Michael R. Treat MD, Laser Tissue Welding: A Comprehensive Review of Current and Future Clinical Applications, Laser Surgery and Medicine Principles and Practice, 1996, pp. 381–415.

(List continued on next page.)

Primary Examiner—Julian W. Woo
(74) Attorney, Agent, or Firm—Stoel Rives LLP

(57) ABSTRACT

Anastomosis procedures and anastomosis cutting procedures are achieved with an anvil apparatus that is externally positioned through the wall of a vessel into the vessel lumen. The externally positioned anvil apparatus has an anvil that engages a cutter to form a vessel opening. The anvil is larger than the cutter to enable the vessel to be cut as it is compressed between the cutter and the anvil. The anvil may have a spherical engaging end for use with a cylindrical cutter for forming circular openings in a manner such that the anvil self centers. The anvil and cutter may also be adapted to form elliptical openings. The balloon may be solid or deployable.

40 Claims, 36 Drawing Sheets

U.S. PATENT DOCUMENTS

| | | | |
|---|---|---|---|
| 2,434,030 A | 1/1948 | Yeomans | |
| 2,818,852 A | 1/1958 | Kugler | |
| 3,104,666 A | 9/1963 | Hale et al. | |
| 3,254,650 A | 6/1966 | Collito | |
| 3,258,012 A | 6/1966 | Nakayama et al. | |
| 3,701,352 A | 10/1972 | Bosworth | 128/305 |
| 3,776,237 A | 12/1973 | HIll et al. | 128/305 |
| 3,837,345 A * | 9/1974 | Matar | 606/159 |
| 4,018,228 A | 4/1977 | Goosen | |
| 4,216,776 A | 8/1980 | Downie et al. | |
| 4,233,981 A | 11/1980 | Schomacher | |
| 4,243,048 A * | 1/1981 | Griffin | 600/567 |
| 4,294,255 A | 10/1981 | Geroc | 128/334 C |
| 4,366,819 A | 1/1983 | Kaster | |
| 4,493,321 A | 1/1985 | Leather | 128/305 |
| 4,523,592 A | 6/1985 | Daniel | |
| 4,553,542 A | 11/1985 | Schenck et al. | |
| D281,721 S | 12/1985 | Scanlan | D24/28 |
| 4,607,637 A | 8/1986 | Berggren et al. | |
| 4,657,019 A | 4/1987 | Walsh et al. | |
| 4,667,673 A | 5/1987 | Li | 128/334 C |
| 4,721,109 A | 1/1988 | Healey | |
| 4,752,024 A | 6/1988 | Green et al. | |
| 4,819,637 A | 4/1989 | Dormandy, Jr. et al. | |
| 4,846,186 A | 7/1989 | Box et al. | |
| 4,848,367 A | 7/1989 | Avant et al. | |
| 4,861,336 A | 8/1989 | Helzel | |
| 4,873,977 A | 10/1989 | Avant et al. | |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 4,930,674 A | 6/1990 | Barak | |
| 5,035,702 A | 7/1991 | Taheri | |
| 5,047,039 A | 9/1991 | Avant et al. | |
| 5,047,041 A | 9/1991 | Samuels | |
| 5,129,913 A | 7/1992 | Ruppert | |
| 5,192,294 A | 3/1993 | Blake, III | |
| 5,222,970 A | 6/1993 | Reeves | |
| 5,254,113 A | 10/1993 | Wilk | |
| 5,290,306 A | 3/1994 | Trotta et al. | |
| 5,336,233 A | 8/1994 | Chen | |
| 5,366,462 A | 11/1994 | Kaster et al. | |
| 5,392,979 A | 2/1995 | Green et al. | |
| 5,411,475 A | 5/1995 | Atala et al. | |
| 5,456,712 A | 10/1995 | Maginot | |
| 5,465,895 A | 11/1995 | Knodel et al. | |
| 5,478,320 A | 12/1995 | Trotta | |
| 5,478,354 A | 12/1995 | Tovey et al. | |
| 5,522,834 A | 6/1996 | Fonger et al. | |
| D372,310 S | 7/1996 | Hartnett | |
| 5,549,122 A | 8/1996 | Detweilwer | 128/898 |
| 5,613,979 A | 3/1997 | Trotta et al. | |
| 5,616,114 A | 4/1997 | Thornton et al. | |
| 5,620,649 A | 4/1997 | Trotta | |
| 5,634,936 A | 6/1997 | Linden et al. | |
| 5,643,305 A | 7/1997 | Al-Tameem | 606/180 |
| 5,662,580 A | 9/1997 | Bradshaw et al. | |
| 5,662,700 A | 9/1997 | Lazarus | |
| 5,690,662 A | 11/1997 | Chiu et al. | |
| 5,695,504 A | 12/1997 | Gifford, III et al. | |
| 5,702,412 A | 12/1997 | Popov et al. | |
| 5,732,872 A | 3/1998 | Bolduc et al. | |
| 5,766,158 A | 6/1998 | Opolski | |
| 5,779,731 A | 7/1998 | Leavitt | |
| 5,817,113 A | 10/1998 | Gifford, III et al. | 606/153 |
| 5,830,222 A | 11/1998 | Makower | |
| 5,830,228 A | 11/1998 | Knapp et al. | |
| 5,843,027 A | 12/1998 | Stone et al. | |
| 5,843,088 A | 12/1998 | Barra et al. | |
| 5,860,992 A | 1/1999 | Daniel et al. | |
| 5,861,005 A | 1/1999 | Kontos | |
| 5,868,763 A | 2/1999 | Spence et al. | |
| 5,893,369 A | 4/1999 | LeMole | |
| 5,910,153 A | 6/1999 | Mayenberger | |
| 5,951,576 A | 9/1999 | Wakabayashi | |
| 5,954,735 A | 9/1999 | Rygaard | 606/153 |
| 5,976,178 A | 11/1999 | Goldsteen et al. | 623/1 |
| 6,007,576 A | 12/1999 | McClellan | |
| 6,022,367 A | 2/2000 | Sherts | |
| 6,036,700 A | 3/2000 | Stefanchik et al. | |
| 6,036,710 A * | 3/2000 | McGarry et al. | 606/184 |
| 6,068,637 A | 5/2000 | Popov et al. | 606/159 |
| 6,080,173 A | 6/2000 | Williamson, IV et al. | |
| 6,080,176 A | 6/2000 | Young | |
| 6,117,148 A | 9/2000 | Ravo et al. | |
| 6,171,319 B1 | 1/2001 | Nobles et al. | |
| 6,176,413 B1 | 1/2001 | Heck et al. | |
| 6,190,396 B1 | 2/2001 | Whitin et al. | 606/144 |
| 6,209,773 B1 | 4/2001 | Bolduc et al. | 606/176.1 |
| 6,241,743 B1 | 6/2001 | Levin et al. | 606/153 |
| 6,248,117 B1 | 6/2001 | Blatter | |
| 6,280,460 B1 | 8/2001 | Bolduc et al. | 606/222 |
| 6,355,050 B1 | 3/2002 | Andreas et al. | 606/144 |
| 6,358,258 B1 | 3/2002 | Arcia et al. | 606/139 |
| 6,391,038 B2 | 5/2002 | Vargas et al. | |
| 2002/0082614 A1 | 6/2002 | Logan et al. | |

OTHER PUBLICATIONS

Boeckx, Willy D. MD, PhD, Scanning Electron Microscopic Analysis of the Stapled Microvascular Anastomosis in the Rabbit, http://198.76.172.231/cgi–bin/bio/con/annals/atseq/63/S128/1997/ALL, Ann of Thorac Surgery, 1997, pp. 63:S128–34.

Boeckx, Willy D. MD, PhD, et al., Scanning Electron Microscopic Analysis of the Stapled Microvascular Anastomosis in the Rabbit, Ann Thorac Surg, 1997, pp. 63:S128–34.

Borst, Cornelium MD, PhD, et al., Minimally Invasive Coronary Artery Bypass Grafting: On the Beating Heart and via Limited Access, Ann Thorac Surg, 1997, pp. S1–S5.

Brittinger, Wolf Dieter et al., Vascular Access for Hemodialysis in Children, Pediatric Nephrology, 1997, pp. 11:87–95.

Cecchetti, W., et al., 980nm High Power Diode Laser in Surgical Applications, Biomedical Optical Instrumentation and Laser–Assisted Biotechnology, 1996, pp. 227–230.

Chikamatsu, Eiji MD, et al., Comparison of Laser Vascular Welding, Interrupted Sutures, and Continuous Sutures in Growing Vascular Anastomoses, Lasers in Surgery and Medicine, vol. 16, No. 1, 1995, pp. 34–40.

Cooley, Brain C. MD, Heat–induced Tissue Fusion for Microvascular Anastomosis, Microsurgery, vol. 17, No. 4, 1996, pp. 198–208.

Cope, Constantin and Stanley Baum, Catheters, Methods, and Injectors for Superselective Catheterization, Abram's Angiography Vascular and Interventional Radiology, vol. 1, Fourth Edition, pp. 155–165.

D'Amelio, Frank D. et al., Fiber Optic Angioscopes, Novel Optical Fiber Techniques for Medical Applications, vol. 494, Aug. 21, 1984, pp. 44–51.

Deckelbaum, Lawrence I. MD, Cardiovascular Applications of Laser Technology, Laser Surgery and Medicine Principles and Practice, 1996, pp. 1–27.

Dumanian, G.A. MD et al., A New Photopolymerizable Blood Vessel Glue That Seals Human Vessel Anastomoses Without Augmenting Thrombogenicity, Plastic and Reconstructive Surgery, vol. 95, No. 5, Apr. 1995, pp. 901–907.

Dumitras, D.C. D.C.A. DUTU, Surgical Properties and Applications of Sealed–Off $CO_2$ Lasers, Biomedical Optical Instrumentation and Laser–Assisted Biotechnology, 1996, pp. 231–239.

Falciai, R. et al., Oxide Glass Hollow Fiber for $CO_2$ Laser Radiation Transmission, Novel Optical Fiber Techniques for Medical Applications, vol. 494, Aug. 21, 1984, pp. 84–87.

Gershony, Gary MD et al., Novel Vascular Sealing Device for Closure of Percutaneous Vascular Access Sites, Catherization and Cardiovascular Diagnosis, Sep. 1998, pp. 82–88.

Giele, Henk M.B.B.S., Histoacryl Glue as a Hemostatic Agent in Microvascular Anastomoses, Plastic and Reconstructive Surgery, vol. 94, No. 6, Nov. 1994, p. 897.

Goldman, Leon and W.A. Taylor, Development of a Laser Intravascular Fiber Optic Probe for the Treatment of Superficial Telangiectasia of the Lower Extremity in Man, Novel Optical Fiber Techniques for Medical Applications, vol. 494, Aug. 21, 1984, pp. 76–83.

Gray, John L. MD et al., FGF–1 Affixation Stimulates ePTFE Endothelialization without Intimal Hyperplasia[1,2], Journal of Surgical Research Clinical and Laboratory Investigation, vol. 57, No. 5, Nov. 1994, pp. 596–612.

Greisler, Howard P. et al., Biointeractive Polymers and Tissue Engineered Blood Vessels, Biomaterials, vol. 17, No. 3, Feb. 1996, pp. 329–336.

Han, Seung–kyu MD, PhD et al., Microvascular Anastomosis with Minimal Suture and Fibrin Glue: Experimental and Clinical Study, Microsurgery, vol. 18, No. 5, 1998, pp. 306–311.

Haruguchi, Hiroaki et al., Clinical Application of Vascular Closure Staple Clips for Blood Access Surgery, ASAIO Journal, Sep.–Oct. 1998, pp. M562–564.

Humar, Abhinav MD et al, The Acutely Ischemic Extremity After Kidney Transplant An Approach to Management, Surgery, Mar. 1998, pp. 344–350.

Jaber, Saad F. MD et al., Role of Flow Measurement Technique in Anastomotic Quality Assessment in Minimally Invasive CABG, Ann Thorac Surg, 1998, pp. 66:1087–92.

Jones, Jon W. MD, A New Anastomotic Technique in Renal Transplants Reduces Warm Ischemia Time,Clinical Transplantation, 1998, 12:70–72.

Jules S. Scheltes, Msc, et al., Assessment of Patented Coronary End–to–Side Anastomotic Devices Using Micromechanical Bonding, Ann Thorac Surg, 2000, pp. 218–221.

Keskil, S. et al., Early Phase Alterations in Endothelium Dependent Vasorelaxation Responses Due to Aneurysm Clip Application and Related Manipulations, The Euroepan Journal of Neurosurgery, vol. 139, No. 1, 1997, pp. 71–76.

Kirschner, R.A. The Nd:YAG Laser–13 Applications in Surgery, Laser Systems for Photobiology and Photomedicine, 1991, pp. 53–56.

Kung, Robert T.V. PhD et al., Absorption Characteristics at 1.9 μm Effect on Vascular Welding, Lasers in Surgery and Medicine, vol. 13, No. 1, 1993, pp. 12–17.

Lanzetta, M. MD, et al., Fibroblast Growth Factor Pretreatment of 1–MM PTFE Grafts, Microsurgery, vol. 17, No. 11, 1996, pp. 606–611.

Ling Zhang, et al., Venous Microanastomosis with the Unilink System, Sleeve, and Suture Techniques: A Comparative Study in the Rat, Journal of Reconstructive Microsurgery, vol. 13, No. 4, May 1997, pp. 257–262.

Lisi, Gianfranco MD et al., Nonpenetrating Stapling: A Valuable Alternative for Coronary Anastomoses? Ann Thorac Surg 1998, 66, pp. 1705–1708.

Marek, Christopher A., BS et al., Acute Thrombogenic Effects of Fibrin Sealant on Microvascular Anastomoses in a Rat Model, Annals of Plastic Surgery, Oct. 1998, pp. 415–419.

Menovsky, Thomas MD et al, Use of Fibrin Glue to Protect Tissue During $CO_2$ Laser Surgery, The Laryngoscope, vol. 108, No. 9, pp. 1390–1393.

Mignani, A.G. and A.M. Scheggi, The Use of Optical Fibers in Biomedical Sensing, Laser Systems for Photobiology and Photomedicine, 1991, pp. 233–245.

Nataf, Patrick MD et al., Facilitated Vascular Anastomoses: The One Shot Device, Ann of Thorac Surg, 1998, pp. 66:1041–1044.

Nataf, Patrick MD, et al, Nonpenetrating Clips for Coronary Anastomosis, Ann Thorac Surg, 1997, pp. 63:S135–7.

Nataf, Patrick MD, et al., Nonpenetrating Clips for Coronary Anastomosis, http://198.76.172.231/cgi–bin/bio/con/annals/atseq/63/S135/1997/ALL, Ann of Thorac Surg, 1997, pp. 63:S135–7.

Nelson, Christine C. MD, et al., Eye Shield for Patients Undergoing Laser Treatment, American Journal of Ophthalmology, Series 3, vol. 110, No. 1, Jul. 1990, pp. 39–43.

Niemz, Markolf H. References, Laser–Tissue Interactions—Fundamentals and Applications, Springer, 1996, pp. 267–290.

Niemz, Markolf H. Interaction Mechanisms, Laser–Tissue Interacitons—Fundamentals and Applications, Springer, 1996, pp. 45–47.

Niemz, Markolf H. Lasers in Angioplsty and Cardiology, Laser–Tissue Interactions—Fundamentals and Applications, Springer, 1996, pp. 216–221.

Papalois, V.E. et al., Use of Vascular Closure Staples in Vascular Access for Dialysis, Kidney and Pancreas Transplantation, International Surgery, Apr.–Jun. 1998, pp. 177–180.

Perkins, Rodney MD, Lasers in Medicine, Lasers Invention to Application, 1987, pp. 101–110.

Piano, Giancarlo MD et al., Assessing Outcomes, Costs, and Benefits of Emerging Technolgy for Minimally Invasive Saphenous Vein In Situ Distal Arterial Bypasses, Archives of Surgery, Jun. 1998, pp. 613–618.

Pikoulis, Emmanouil MD, et al., Rapid Arterial Anastomosis with Titanium Clips, The American Journal of Surgery, Jun. 1998, pp. 494–496.

Poppas, Dix P. MD et al., Preparation of Human Albumin Solder for Laser Tissue Welding, Laser in Surgery and Medicine, vol. 13, No. 5, 1993, pp. 577–580.

Reardon, M. J. et al., Coronary Artery Bypass Conduits: Review of Current Status, The Journal of Cardiovascular Surgery, Jun. 1997, pp. 201–209.

Reichenspumer, Hermann MD, PhD et al., Minimally Invasive Coronary Artery Bypass Grafting: Port–Access Approach Versus Off–Pump Techniques, Ann of Thorac Surg, 1998, pp. 66:1036–1040.

Rouhi, A. Maureen, Contemporary Biomaterials, Chemical & Engineering News, vol. 77, No. 3, Jan. 1999, pp. 51–63.

Russel, D.A. et al., A Comparison of Laser and Arc–Lamp Spectroscopic Systems for In–Vivo Pharmacokinetic Measurements of Photosensitizers Used in Photodynamic Therapy, Laser Systems for Photobiology and Photomedicine, 1991, 193–199.

Saitoh, Satoru MD and Yukio Nakatsuchi MD, Telescoping and Glue Technique in Vein Grafts for Arterial Defects, Plastic and Reconstructive Surgery, vol. 96, No. 6, No. 1995, pp. 1401–1408.

Sanborn, Timothy A. Laser Angioplasty, Vascular Medicine A Textbook of Vascular Biology and Diseases, pp. 771–787.

Schnapp, Lynn M. MD, Elmer's Glue Elsie and You: Clinical Applications of Adhesion Molecules, The Mount Sinai Journal of Medicine, May 1998, pp. 224–231.

Self, Steven B. MD et al., Limited Thrombogenicity of Low Temperature, Laser–Welded Vascular Anastomoses, Lasers in Surgery and Medicine, vol. 18, No. 3, 1996, pp. 241–247.

Shennib, Hani MD et al., Computer–Assisted Telemanipulation: An Enabling Technology for Endoscopic Coronary Artery Bypass, Ann Thorac Surg 1998, pp. 66:1060–3.

Shindo, Maisie L. MD et al., Use of a Mechanical Microvascular Anastomotic Device in Head and Neck Free Tissue Transfer, Archives of Otolaryngology–Head & Neck Surgery, May, 1996, pp. 529–532.

Shinoka, Toshiharu MD et al., Creation of Viable Pulmonary Artery Autografts Through Tissue Engineering, The Journal of Thoracic and Cardiovascular Surgery, Mar. 1998, pp. 536–546.

Spinelli, P. et al., Endoscopic Photodynamic Therapy: Clinical Aspects, Laser Systems for Photobiology and Photomedicine, 1991, pp. 149–155.

Stephenson, Jr., Edward R MD et al, Robotically Assisted Microsurgery for Endoscopic Coronary Artery Bypass Grafting, Ann of Thorac Surg, 1998, pp. 66:1064–1067.

Tulleken, Cornelis A. F. MD PhD, et al., Nonocclusive Excimer Laser–Assisted End–to–Side Anastomosis, Ann Thorac Surg, 1997, pp. 63:S138–42.

Tulleken, Cornelis A. F. MD, PhD, et al., Nonocclusive Excimer Laser–Assisted End–to–Side Anastomosis, http://198.76.172.231/cgi–bin/bio/con/annals/atseq/63/S138/1997/ALL, Ann Thorac Surg, 1997, pp. 63:S138–42.

Turi, Zoltan G., MD et al., Plugging the Artery With a Suspension: a Cautious Apprasial, Catherization and Cardiovascular Diagnosis, Sep. 1998, pp. 90–91.

Underwood, M.J. et al., Autogenous Arterial Grafts for Coronary Bypass Surgery: Current Status and Future Perspectives, International Journal of Cardiology 46, 1994, pp. 95–102.

Viligiardi, R. et al., Excimer Laser Angioplasty in Human Artery Disease, Laser Systems for Photobiology and Photomedicine, 1991, pp. 69–72.

Web Page, http://198.76.172.231/cgi–bin/bio/con/annuals/atseq/63/S122/1997 figs/5081f6, The Microvascular Anastomotic System as marketed by the Medical–Surgical Division of 3M Health Care, The Society of Thoracic Surgeons, 1997.

Weinschelbaum, Ernesto MD et al., Left Anterior Descending Coronary Artery Bypass Grafting Through Minimal Thoracotomy, Ann Thoracic Surg, 1998, pp. 66:1008–11.

Werker, Paul M. N. MD, Ph.D, et al., Review of Facilitated Approaches to Vascular Anastomosis Surgery, Ann Thorac Surg, 1997, pp. S122–S127.

Zarge, Joseph I. MD et al, Fibrin Glue Containing Fibroblast Growth Factor Type 1 and Heparin Decreases Platelet Deposition, The American Journal of Surgery, Aug. 1997, pp. 188–192.

USSC Brochure for the VCS® Clip Applier System, Improve Patency and Reduce or Time in Vascular Anastomoses, 1995.

Jimenez–Martinez, M. MD et al., *Isolated Tricuspid Endocarditis with Ventricular Septal Defect*, *The Journal of Thoracic and Cardiovascular Surgery*, vol. 61, No. 5, 1971 pp. 665–709.

* cited by examiner

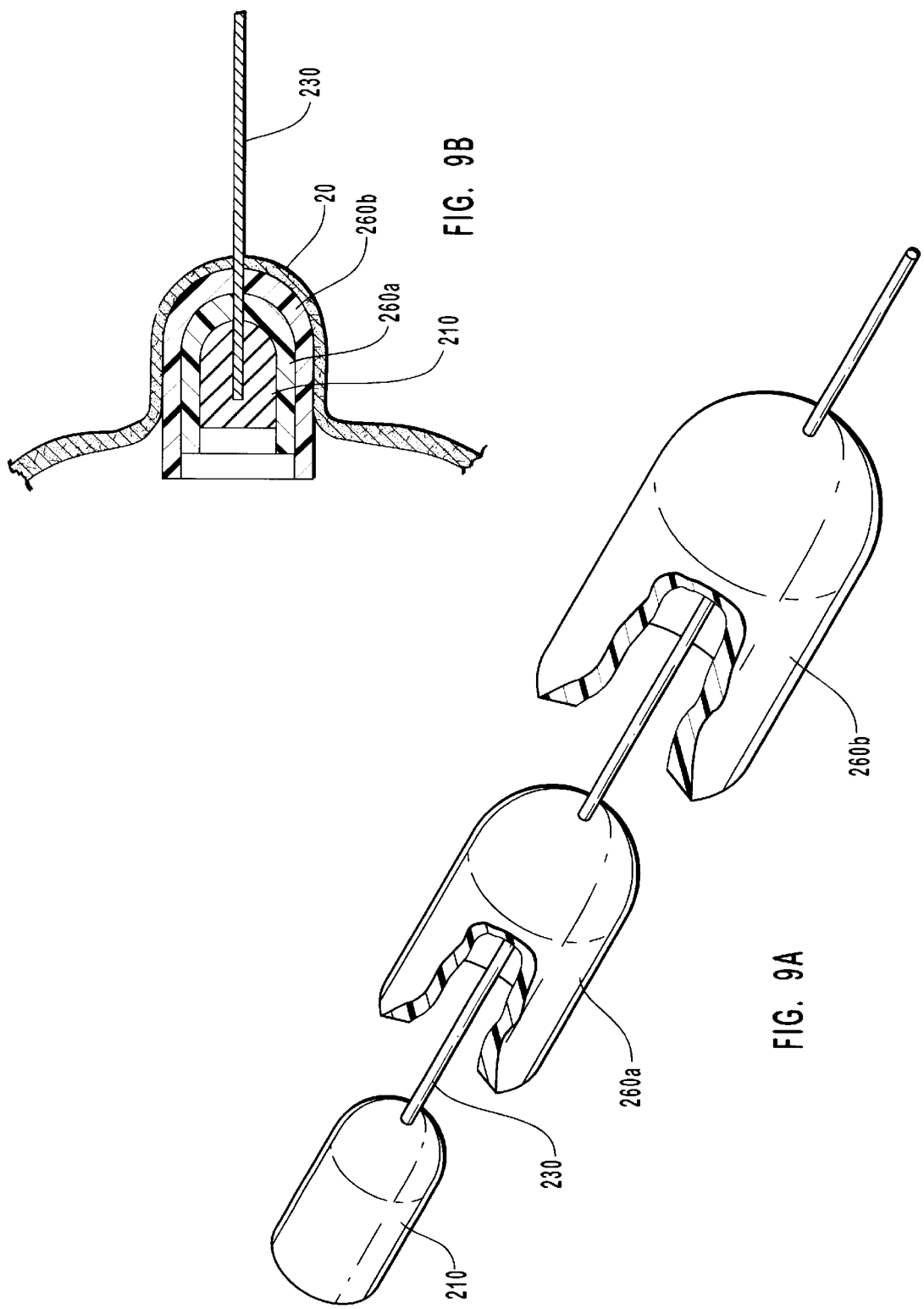

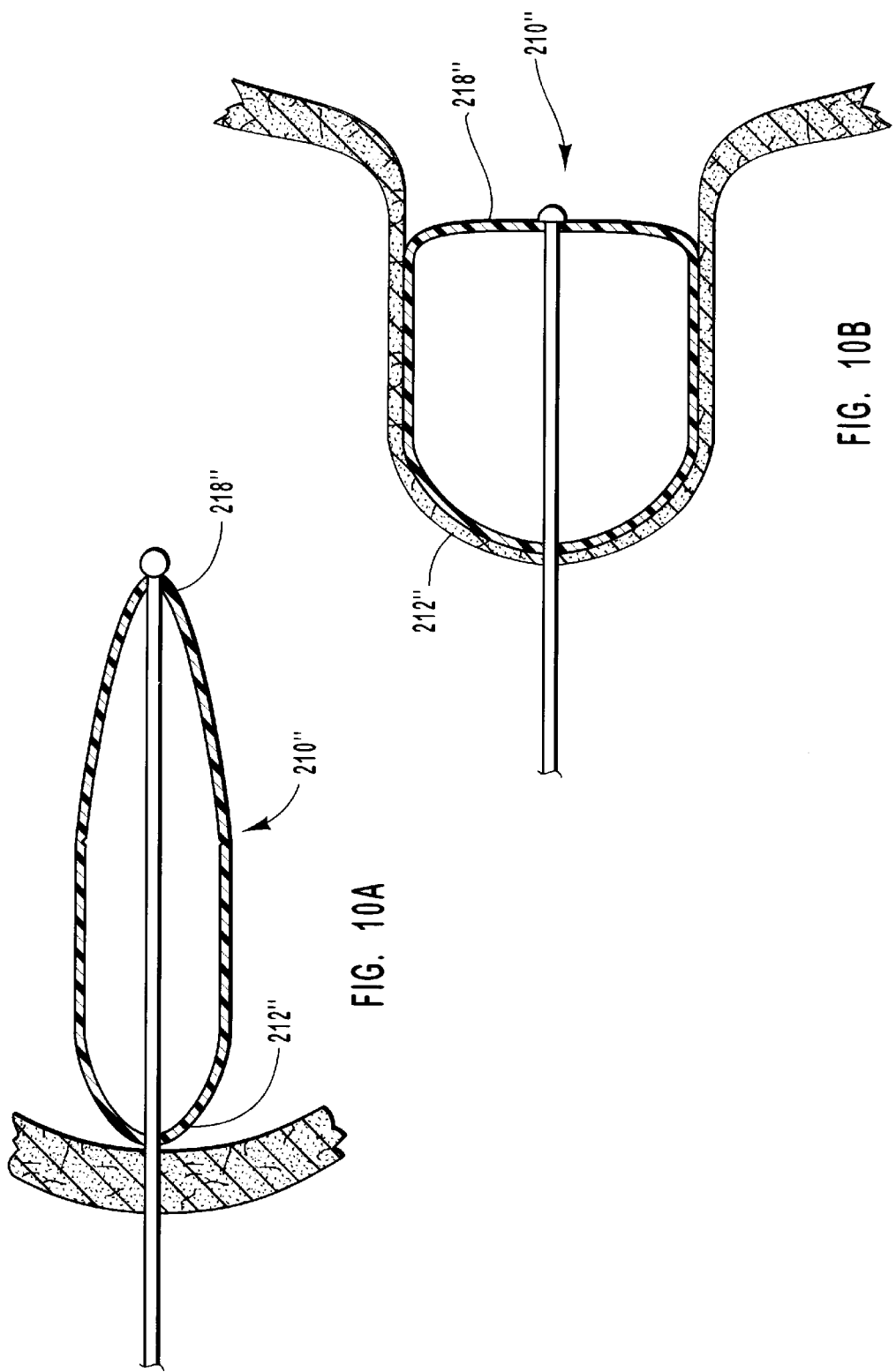

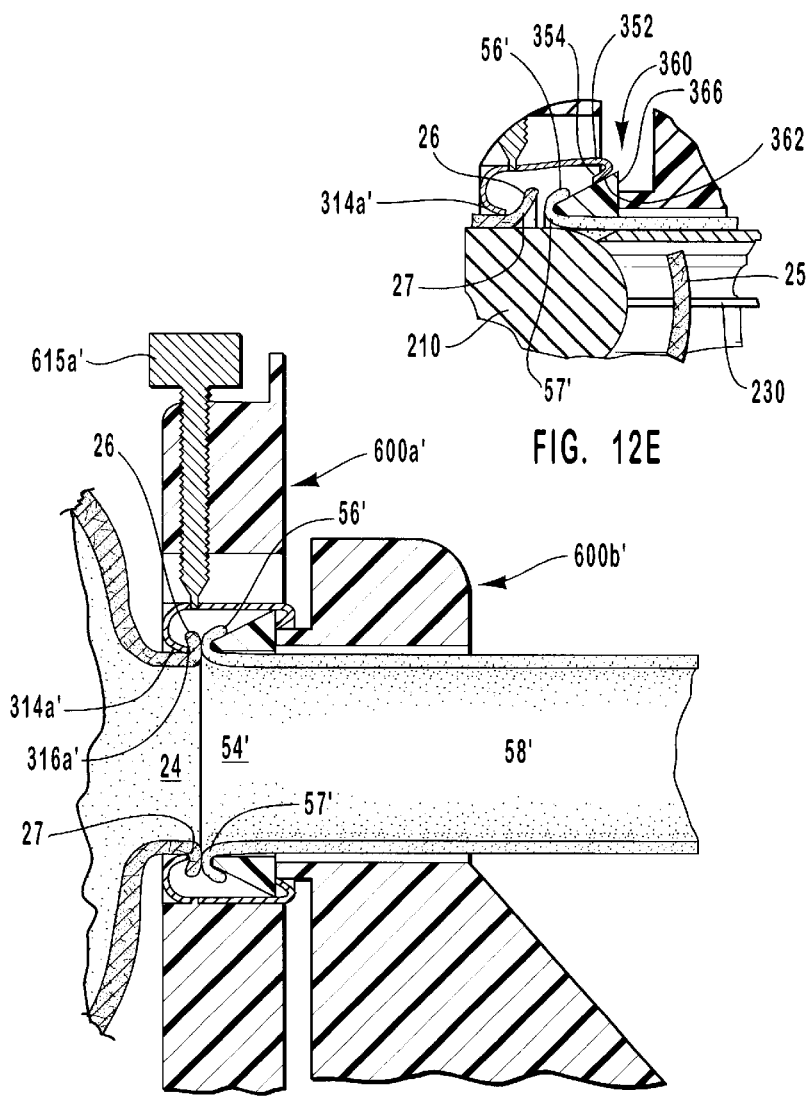
FIG. 12E
FIG. 12F
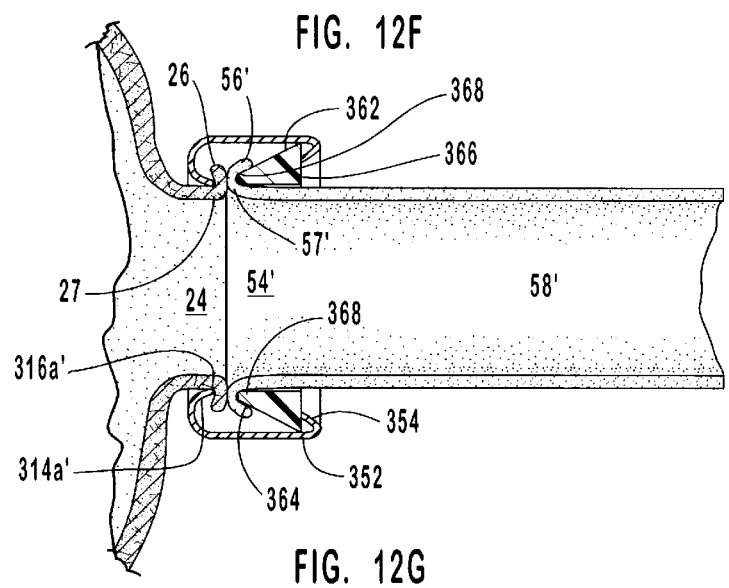
FIG. 12G

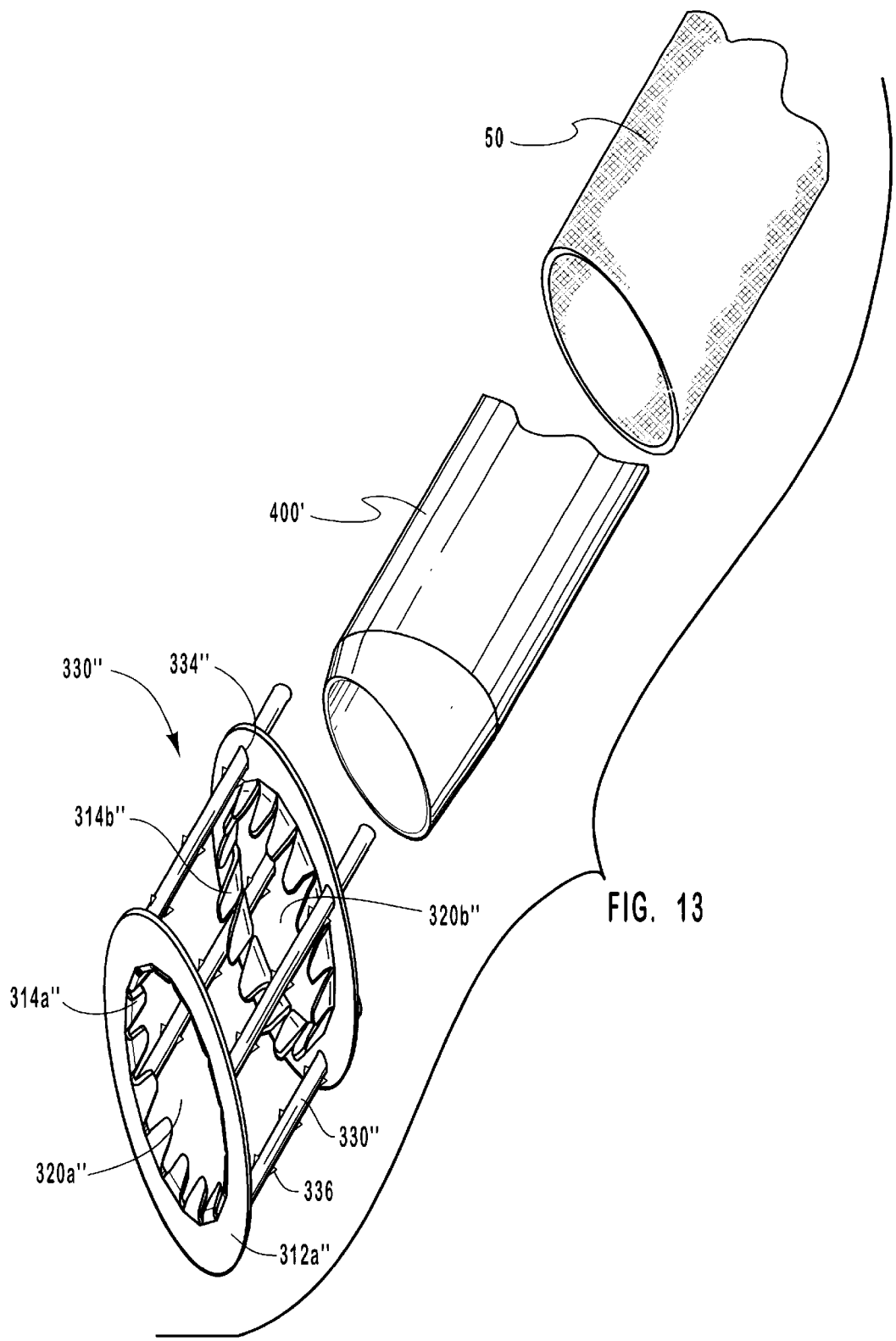

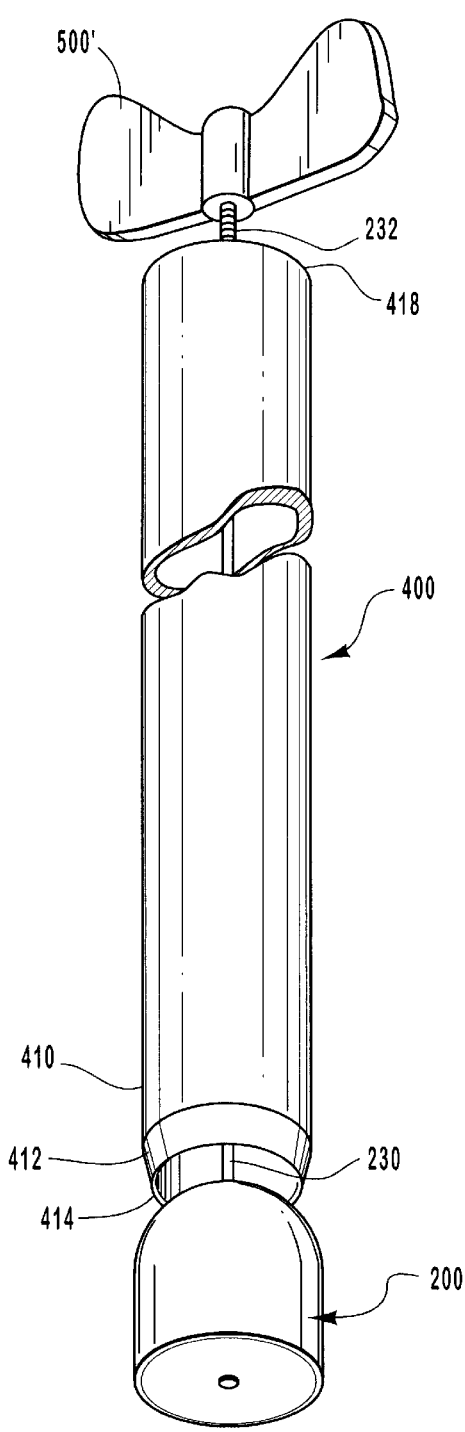
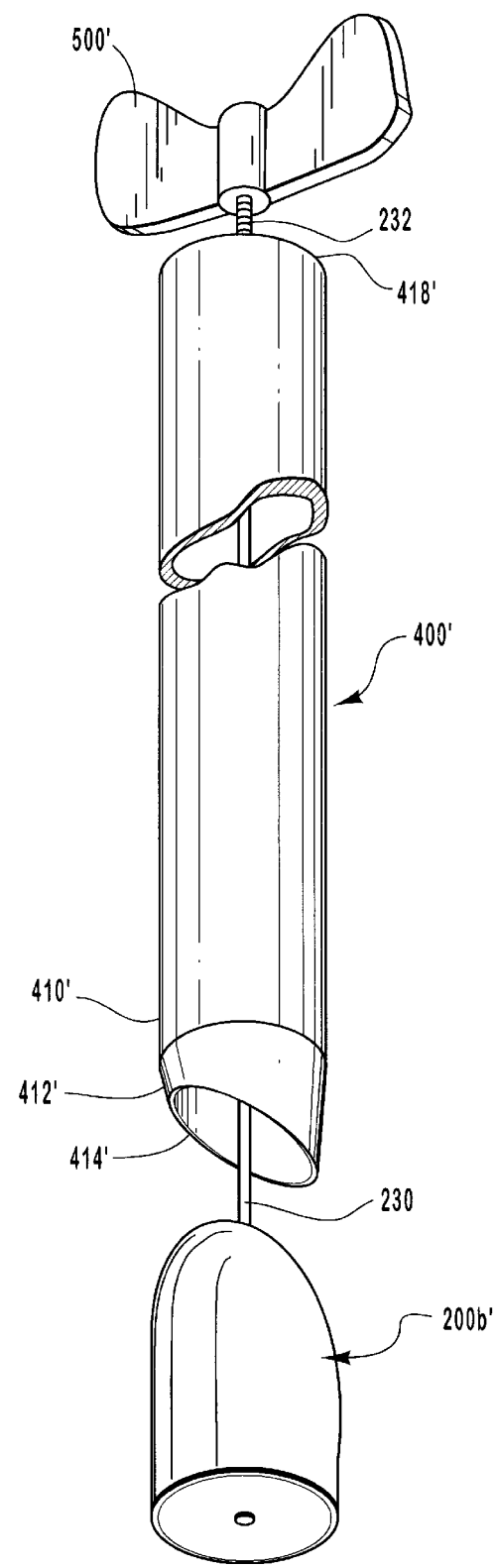
FIG. 14A
FIG. 14B

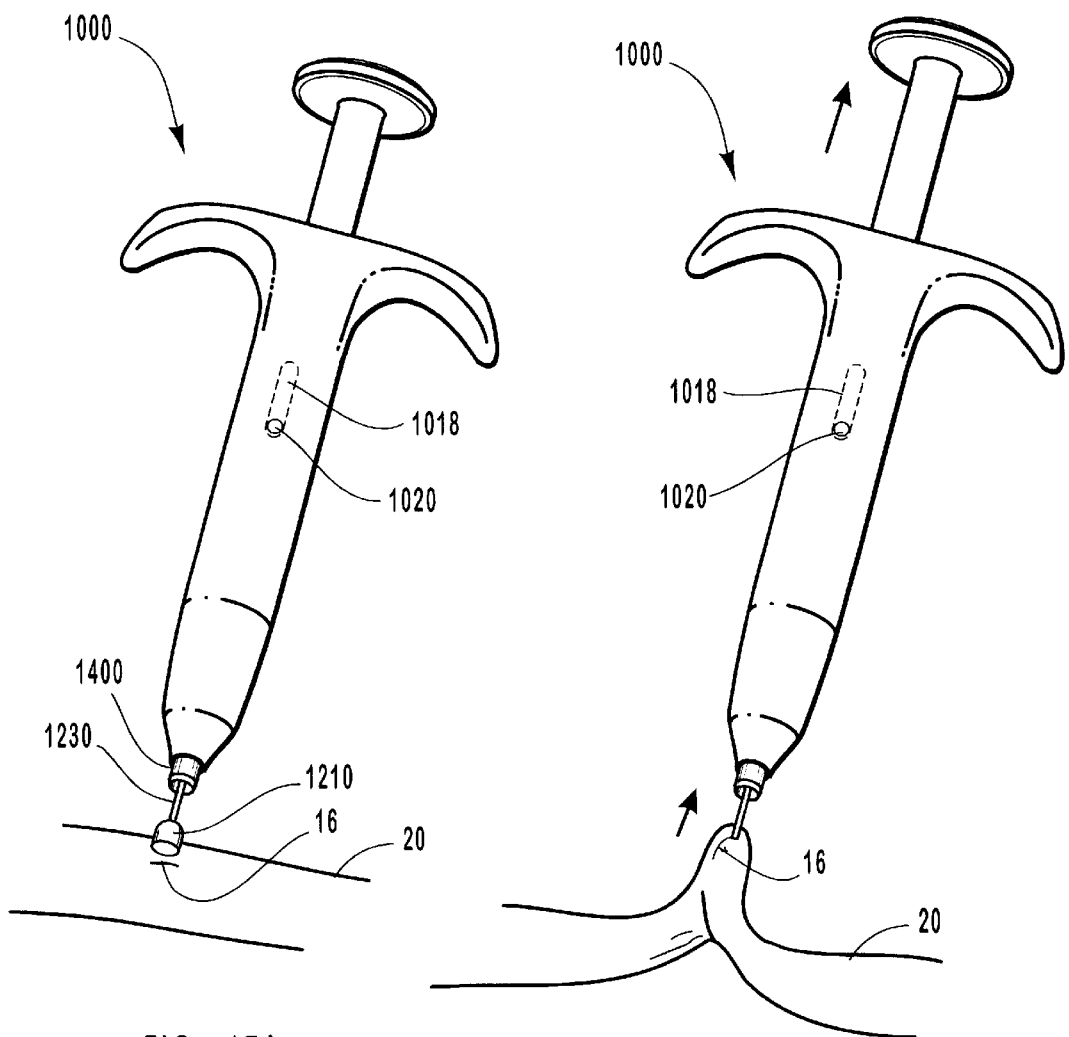
FIG. 17A
FIG. 17B
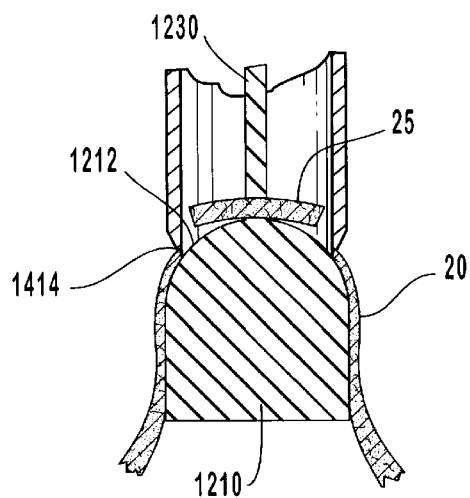
FIG. 17C

EXTERNALLY DIRECTED ANASTOMOSIS SYSTEMS AND EXTERNALLY POSITIONED ANASTOMOSIS FENESTRA CUTTING APPARATUS

RELATED APPLICATIONS

The present application is a continuation-in-part patent application of U.S. application Ser. No. 09/293,366 filed Apr. 16, 1999 and U.S. patent application Ser. No. 09/460,740 entitled Compression Plate Anastomosis Apparatus which was filed on Dec. 14, 1999 on behalf of Duane D. Blatter, Kenneth C. Goodrich, Mike Barrus, and Bruce M. Burnett. Ser. No. 09/460,740 is incorporated herein by specific reference.

BACKGROUND OF THE INVENTION

1. The Field of the Invention

The present invention is directed generally to anastomosis methods, systems and devices. More specifically the present invention is directed to compression plate vascular anastomosis methods, systems and devices with the use of a vascular anvil.

2. Relevant Technology

Endoscopic applications are generally used in intracavity procedures such as intrathoracic and intraabdominal procedures. Peripheral techniques are usually employed in other body regions, such as arms and legs. It is desirable to be able to provide by active endoscopic or peripheral procedures a variety of medical services that are currently provided by techniques that are more invasive and more demanding in time and in medical resources and skills. This goal is justified by the efficiency, effectiveness, safety, low cost, and preventive accomplishments of active endoscopic or peripheral procedures. In particular, this invention provides new methods, devices and systems for performing vascular anastomoses by intraluminally directed active endoscopic or peripheral procedures. The intraluminally directed or intravascular part of the procedures of this invention is based on an examination performed by, for example, fluoroscopy, and extraluminal manipulation is performed endoscopically or according to a peripheral technique.

One aspect of this invention encompasses the quasi-simultaneity of the exploration, diagnosis and corrective tasks that can be achieved in vascular anastomoses performed by the active endoscopic or peripheral procedures of this invention. Another aspect of this invention includes the minimally invasive character of the vascular anastomoses that are performed by the active endoscopic or peripheral procedures of this invention. These procedures are also characterized by comparatively reduced requirements of medical facilities and skill. To more effectively describe and enable the present invention, a review of some basic terminology and related technology is offered in the immediately following subsections.

2.1. Terminology

An anastomosis is an operative union of two hollow or tubular structures. Anastomotic structures can be part of a variety of systems, such as the vascular system, the digestive system or the genitourinary system For example, blood is shunted from an artery to a vein in an arteriovenous anastomosis, and from the right pulmonary artery to the superior vena cava in a cavopulmonary anastomosis. In other examples, afferent and efferent loops of jejunum are joined in a Braun's anastomosis after gastroenteroscopy, the ureter and the Fallopian tube are joined in a ureterotubal anastomosis, and the ureter and a segment of the sigmoid colon are joined in a ureterosigmoid anastomosis. In microvascular anastomosis, very small blood vessels are anastomosed usually under surgical microscope.

An anastomosis is termed end-to-end when the terminal portions of tubular structures are anastomosed, and it is termed end-to-side when the terminal portion of a tubular structure is anastomosed to a lateral portion of another tubular or hollow structure. In an end-to-side anastomosis, we often refer to the structure whose end is anastomosed as the "graft vessel" while the structure whose side wall is anastomosed is referred to as the "receiving structure".

Anastomotic material typically includes autologous material, but it can also include heterologous material or synthetic material. An autologous graft is a graft in which the donor and recipient areas are in the same individual. Heterologous material is derived from an animal of a different species. The graft can be made of a synthetic material such as expanded polytetrafluoroethylene ("ePTFE"). Wolf Dieter Brittinger, Gottfried Walker, Wolf-Dieter Twittenhoff, and Norbert Konrad, *Vascular Access for Hemodialysis in Children, Pediatric Nephrology*, Vol. 11 (1997) pp. 87–95.

A nonocclusive anastomosis is typically an end-to-side anastomosis in which the flow of matter through the vessel that is anastomosed in its side is not interrupted while the anastomosis is performed. Most conventional techniques for vascular anastomosis require the interruption of blood flow through the receiving vessel while the anastomosis is performed.

Although the parts of a blood vessel are designated by well-known terms in the art, a few of these parts are briefly characterized here for introducing basic terminology. A blood vessel is in essence a tubular structure. In general, the region comprised within tubular walls, such as those defining a blood vessel or the walls defining the tubular member of an endoscope, is termed the lumen or the intraluminal space. A lumen that is not occluded is a patent lumen and the higher the patency of a blood vessel, the less disrupted the blood flow through such vessel is. A reduction of a blood vessel's patency can be caused by a stenosis, which is generally a stricture or narrowing of the blood vessel's lumen. A hyperplasia, or tissue growth, can also reduce a blood vessel's patency. Reduction of blood vessel patency, and in general a disruption in a vessel's blood flow, can lead to ischemia, which is a local lack of oxygen in tissue due to a mechanical obstruction of the blood supply.

A stent is a device that can be used within the lumen of tubular structures to assure patency of an intact but contracted lumen. Placement of a stent within an occluded blood vessel is one way of performing an angioplasty, which is an operation for enlarging a narrowed vascular lumen. Angioplasty and bypass are different ways for reestablishing blood supply, an operation that is called revascularization.

A blood vessel is composed of three distinct layers. From inside to outside, these layers include the intima, the media and the adventitia. The intima is a single layer of flat cells that collectively line the lumen. The media is a thick middle layer composed of smooth muscle cells. The adventitia is an outer layer that comprises fibrous covering.

Angiography is a technique for performing a radiograph of vessels after the injection of a radio-opaque contrast material. This technique usually requires percutaneous injection of a radio-opaque catheter and positioning under fluoroscopic control. An angiogram is a radiograph obtained by angiography. Fluoroscopy is an examination technique with an apparatus, the fluoroscope, that renders visible the patterns of X-rays which have passed through a body under examination.

2.2 Related Technology

The operative union of two hollow or tubular structures requires that the anastomosis be tight with respect to the flow of matter through such structures and also that the anastomosed structures remain patent for allowing an uninterrupted flow of matter therethrough. For example, anastomosed blood vessels should not leak at the anastomosis site, the anastomotic devices should not significantly disrupt the flow of blood, and the anastomosis itself should not cause a biological reaction that could lead to an obstruction of the anastomosed blood vessels. In particular, anastomosed blood vessels should remain patent and they should ideally not develop hyperplasia, thrombosis, spasms or arteriosclerosis.

Because anastomosed structures are composed of tissues that are susceptible to damage, the anastomosis should furthermore not be significantly detrimental to the integrity of these tissues. For example, injury to endothelial tissue and exposure of subintimal connective tissue should be minimized or even eliminated in vascular anastomosis.

Because structures to be anastomosed are internal, an anastomosis requires a degree of invasion. The invasive character of an anastomosis, however, should be minimized subject to the reliable performance of a satisfactory anastomosis. Accordingly, there has been a noticeable trend during the last quarter of this century towards less invasive surgical intervention, a surgical style that is termed minimally invasive surgery. This style is characterized by pursuing a maximal treatment effect with minimal damage to surrounding and overlying normal structures. In addition, successful minimally invasive procedures should procure patency and they should minimize damage to the tissues of the anastomosed structures themselves.

A plurality of factors provide a propitious environment for this trend towards minimally invasive surgery. These factors include the development of high-technology diagnostic devices, the innate characteristics of human psychology and economic imperatives.

High-technology diagnostic devices such as flexible fiberoptic endoscopes and intravascular catheters have considerably enhanced our ability for performing a reliable spaciotemporal location of disease. More specifically, these devices permit the early and accurate determination of disease processes and their loci. Furthermore, it is known that the earlier a tumor or growth can be identified, the more responsive it is to therapy by a minimally invasive technique. See Rodney Perkins, *Lasers in Medicine in Lasers—Invention to Application*, edited by John R. Whinnery, Jesse H. Ausubel, and H. Dale Langford, p. 104, National Academy of Engineering, National Academy Press, Washington, D.C. 1987. (This article will hereinafter be referred to as "*Lasers—Invention to Application*"). See also Edward R. Stephenson, Sachin Sankholkar, Christopher T. Ducko, and Ralph J. Damiano, *Robotically Assisted Microsurgery for Endoscopic Coronary Artery Bypass Grafting, Annals of Thoracic Surgery*, Vol. 66 (1998) p. 1064. (This article will hereinafter be referred to as "*Endoscopic Coronary Artery Bypass Grafting*").

Human psychology also contributes to the growing trend towards minimally invasive techniques. This is attributed to the accepted prevailing preference of a minimally invasive technique with respect to a more invasive surgical technique whenever the outcomes of these two techniques are equivalent.

Finally, minimally invasive techniques are generally cost effective to insurers and to society in general because they are performed on an outpatient basis or else they require comparatively shorter hospitalization time. Furthermore, the less tissue is invasively effected in a procedure, the more likely it is that the patient will recover in a comparatively shorter period of time with lower cost hospitalization. Therefore, economic factors also favor the development of minimally invasive techniques because they can be performed with lower morbidity risk and they satisfy economic imperatives such as reduced cost and reduced loss of productive time. See Rodney Perkins in *Lasers—Invention to Application*, p. 104; *Endoscopic Coronary Artery Bypass Grafting*, pp. 1064, 1067.

Particularly in the field of vascular anastomosis, it is acknowledged that there is an increasing demand for an easier, quicker, less damaging, but reliable procedure to create vascular anastomosis. This demand is further revitalized by the movement of vascular procedures towards minimally invasive procedures. See Paul M. N. Werker and Moshe Kon, *Review of Facilitated Approaches to Vascular Anastomosis Surgery, Annals of Thoracic Surgery*, Vol. 63 (1997) pp. S122–S127. (This work will hereinafter be referred to as "*Review of Facilitated Approaches to Vascular Anastomosis*").

Conventional exploration and anastomosis techniques are not always implemented in such a way as to satisfy the demand for an easier, quicker, less damaging, but reliable vascular anastomosis. The following overview of conventional exploration and anastomosis techniques closes this background section on related technology.

Exploration of a blood vessel typically provides necessary information for locating and diagnosing vascular abnormalities such as those that reduce vascular patency. This exploration can rely on examination techniques such as angiography and endoscopy. Vascular abnormalities are usually detected fluoroscopically according to an angiography procedure. When it is concluded that the appropriate corrective action requires an anastomosis, conventional procedures ordinarily follow a sequence in which the anastomosis is not performed at the time when the initial exploration and diagnostic are performed, but at a later time and in a typically different clinical setup. Accordingly, the time and resources that are spent during the exploration and diagnostic phases are not directly employed in the performance of an appropriate corrective action, such as an anastomosis.

By performing an anastomosis considerably after the initial exploration has taken place and in a different location and clinical environment, these conventional procedures also waste a significant part of the information acquired at the exploration phase. Images obtained during an angiographic procedure are typically recorded on film or digital medium. In current clinical practice, these recorded images are reviewed in a subsequent clinical setting and based upon a knowledge of external anatomy, the lesion location and optimal site for anastomosis are estimated. This process sacrifices potentially useful information. Fluoroscopic visualization is no longer available without repeating the angiogram procedure, and in conventional practice external anatomic localization is used in correlation with previously recorded images. In addition to this external inspection, conventional procedures could rely on imaging for determining the optimal anastomosis site when corrective action is taken. However, having to reacquire information leads to a waste of resources, it significantly increases the period of time from exploration to corrective action, it is an additional burden on the patient, and it enhances the invasive character of the treatment that is administered to the patient. Furthermore, reacquisition of information might have to be done in an environment that demands higher skills and more resources than they would have been otherwise needed For example, the opening of a body cavity to expose the anatomical region around a potential anastomosis site, the determination of the optimal anastomosis site by external inspection, and the surgical performance of the anastomosis are part of a treatment that is more complex, requires practitioners with more training, and may be more time and resource consuming than the treatment provided by the methods, systems and apparatuses of the present invention.

Vascular anastomosis techniques can be classified in a plurality of groups. Although with various degrees of success, all these techniques generally intend to provide leak-proof joints that are not susceptible to mechanical failure, and they also intend to minimize damage and reduce the undesirable effects of certain operational features that may lead to post-anastomosis complications. Damage to be minimized and operational features whose undesirable effects should be reduced include endothelial coverage injury, exposure of subintimal connective tissue, exposure of an intraluminal foreign component, blood flow interruption, irregularities at the junction, adventitial tissue stripping, intimal injury, installment of a foreign rigid body, use of materials that may have toxic effects, damage to surrounding tissue, extensive vessel eversion, and tissue plane malalignment. Post-anastomosis complications include intimal hyperplasia, atherosclerosis, thrombosis, stenosis, tissue necrosis, vascular wall thinning, and aneurism formation. In addition, vascular anastomosis techniques are characterized by varying abilities to successfully cope with the dilating character of the structures to be anastomosed, their diversity in size, and the possibility that at least one structure may grow after the anastomosis has been performed. Other variables that partially determine the suitability of a specific anastomosis technique include the nature of the material to be anastomosed (for example, autologous, heterologous, or synthetic), the desired reduction in operative time, the skill requirements, and the healing time.

Each one of the techniques discussed hereinbelow for joining anastomosed structures presents a compromise for reducing undesirable effects in the practice of vascular anastomosis. High standards in one or a few aspects of the anastomosis can sometimes be achieved only at the expense of sacrificing what otherwise would have been the benefits of other aspects of the anastomosis.

Since early in the 20th century when vessel anastomoses were performed with an acceptable degree of reliability, the standard for creation of a vascular anastomosis has been manual suturing. *Review of Facilitated Approaches to Vascular Anastomosis*, p. S122. Suturing devices and methods are still being developed with the aim at performing less invasive surgical procedures within a body cavity. See, for example, U.S. Pat. No. 5,860,992 disclosing devices and methods for suture placement while performing less invasive procedures.

Regarding the application of sutures in vascular anastomoses, it has been generally reported that "the insertion of transmural stitches, even in experienced hands that employ atraumatic techniques and fine sutures, causes significant damage to the vessel wall. As the result of this the subendothelial matrix becomes exposed to the bloodstream and initiates the formation of a thrombus. The same process takes place at the actual site of the anastomosis in the case of intima-intima apposition. These processes are multifactorial but can cause obstruction of the complete anastomosis, especially in small vessels." *Review of Facilitated Approaches to Vascular Anastomosis*, p. S122. In addition to proximal occlusion, needle-and-suture-radiated intimal penetration is believed to represent a source of platelet emboli, which can cause distal embolization and thus a hazard in brain revascularization and myocardial circulation. Patrick Nataf, Wolff Kirsch, Arthur C. Hill, Toomas Anton, Yong Hua Zhu, Rarmzi Ramnadan, Leonardo Lima, Alain Pavie, Christian Cabrol, and Iradj Gandjbakhch, *Nonpenetrating Clips for Coronary Anastomosis, Annals of Thoracic Surgery*, Vol. 63 (1997) p. S137. (This article will hereinafter be referred to as *"Nonpenetrating Clips for Coronary Anastomosis"*). Furthermore, it is considered that "suture anastomosis of small vessels is time-consuming and tedious and demands a long and continuous training if high patency rates are to be regularly achieved." Willy D. Boeckx, Oliskevigius Darius, Bert van den hof, and Carlo van Holder, *Scanning Electron Microscopic Analysis of the Stapled Microvascular Anastomosis in the Rabbit, Annals of Thoracic Surgery*, Vol. 63 (1997) p. S128. (This work will hereinafter be referred to as *"Microscopic Analysis of Stapled Microvascular Anastomosis"*). In contrast, in all specialties that employ vascular surgery, "there is an increasing demand for a simple, time-saving, but reliable automated, semiautomated, or at least facilitated method to replace the process of manually sutured anastomosis. The most important reason for this demand is the movement of cardiac bypass surgery toward a minimally invasive and possibly even an endoscopic procedure." *Review of Facilitated Approaches to Vascular Anastomosis*, p. S122. In this respect, improvement "may come from techniques that do not lead to exposure of [a] damaged vessel wall to the bloodstrean." Id., p. S122.

Besides the group that includes techniques which rely on suturing, vascular anastomosis techniques can generally be classified in four groups depending on how the tissue is joined and on the type of device or material used for joining the tissue of the anastomosed vessels. These groups are: Stapling and clipping techniques, coupling techniques, pasting techniques, and laser techniques. Id., pp. S122–S127.

2.2.1. Stapling and clipping techniques

Although some staplers have been reported as providing leaky joints, a variety of staplers have been developed for end-to-end and for end-to-side anastomosis. U.S. Pat. No. 5,366,462 discloses a method of end-to-side vascular anastomosis. According to this method, the end of the graft blood vessel that is to be anastomosed is everted by 180°; one end of the staple pierces both vessels with punctures exposed to the blood flow and the other end of the staple pierces the outside of the receiving vessel. U.S. Pat. No. 5,732,872 discloses a surgical stapling instrument that comprises an expandable anvil for aiding in the stapling of a 180° everted end of a graft vessel to a receiving vessel. This patent also discloses a stapling instrument for joining the 180° everted second end of a graft vessel whose opposite end has already been anastomosed. To anastomose this second end, this technique requires clearance around the area in which the anastomosis is performed, exposure of the receiving blood vessel, external anatomic identification, and significant external manipulation in the open area around the anastomosis site. U.S. Pat. No. 4,930,674 discloses methods of end-to-end and end-to-side anastomosis and a surgical stapler that comprises a vessel gripping structure for joining the 180° everted end of a graft vessel to another vessel. U.S. Pat. No. 5,695,504 discloses methods and a system for performing an end-to-side vascular anastomosis, where the system is applicable for performing an anastomosis between a vascular graft and the ascending aorta in coronary artery bypass surgery, particularly in port-access coronary artery bypass graft surgery. This system includes a staple with a configuration that combines the functions of an anchor member and a coupling member into a one-piece anastomosis staple. U.S. Pat. No. 5,861,005 discloses an arterial stapling method and device for stapling an opening in an anatomical structure, whether the opening is deliberately formed or accidentally caused. This device employs a balloon catheter that helps positioning the stapling mechanism properly on the organ to be stapled.

Some stapling devices rely on access to the anastomosis area through an opening that might be as big as or comparable to typical openings that are required in surgical procedures. Furthermore, the 180° eversion of vessel ends is viewed as an operation that can be difficult, particularly in sclerotic vessels. *Review of Facilitated Approaches to Vascular Anastomosis*, p. S123.

In general, clipping techniques rely on arcuate legged clips for achieving a flanged, nonpenetrated, intiral approximation of the anastomosed structures. Reportedly, the use of clips leads to a biologically and technically superior anastomosis as compared to the penetrating microsuture. *Review of Facilitated Approaches to Vascular Anastomosis*, p. S123. By approximating the everted walls of the two vessels to be anastomosed, a clipping technique avoids stitching and reportedly the subsequent risk of intimal hyperplasia. Gianfranco Lisi, Louis P. Perrault, Philippe Menasché, Alain Bel, Michel Wassef, Jean-Paul Vilaine, and Paul M. Vanhoutte, Nonpenetrating Stapling: *A Valuable Alternative to Coronary Anastomoses, Annals of Thoracic Surgery*, Vol. 66 (1998) p. 1707. In addition, maintenance of an uninjured endothelial coverage and avoidance of exposure of subintimal connective tissue are considered important features because "regenerated endothelium presents selective dysfunction that may predispose to spasm and atherosclerosis, thereby affecting both medium-term and long-term graft patency" and the risk of thrombosis at the anastomotic site can be reduced. Id., p. 1707.

Nonpenetrating vascular closure staples ("VCS") have been used in anastomoses performed to provide access for dialysis, as well as in kidney and pancreas transplantation. It has been concluded in light of these anastomoses that "the fact that VCS staples are interrupted and do not disrupt the endothelium or have an intraluminal component makes them ideal" for achieving the goals of kidney transplantation. V. E. Papalois, J. Romagnoli, and N. S. Hakim, *Use of Vascular Closure Staples in Vascular Access for Dialysis, Kidney and Pancreas Transplantation, International surgery*, Vol. 83 (1998) p. 180. These goals include the avoidance of postoperative thrombosis and the avoidance of renal artery stenosis. As with kidney transplants, no anastomotic abnormalities were detected in pancreatic transplants, where the avoidance of arterial stenosis is also very important. Id., p. 180. The results of anastomoses performed for providing vascular access for dialysis were also reported successful. Id., p. 179. In addition, it has been reported that the "VCS applier is easy to manipulate, is as safe as hand-suture methods, and has time saving potential. VCS clips are useful for vascular anastomoses of blood access." Hiroaki Haruguchi, Yoshihiko Nakagawa, Yasuko Uchida, Junichiro Sageshima, Shohei Fuchinoue and Tetsuzo Agishi, *Clinical Application of Vascular Closure Staple Clips for Blood Access Surgery, ASAIO Journal*, Vol. 44(5) (1998) pp. M562–M564.

In a study of microvascular anastomosis of rabbit carotid arteries, some anastomosis were stapled using nonpenetrating 0.9 mm microclips and some anastomosis were conventionally sutured. Arcuate-legged, nonpenetrating titanium clips are applied according to a clipping technique in an interrupted fashion to everted tissue edges at high compressive forces. It is considered that this technique "enables rapid and precise microvascular reconstructions, but requires both training and evertable tissue walls." *Nonpenetrating Clips for Coronary Anastomosis, Annals of Thoracic Surgery*, p. S135. An example of this clip applier is the VCS device, Autosuture, United States Surgical Corporation, Norwalk, Connecticut. *Nonpenetrating Clips for Coronary Anastomosis*, pp.S135–S137. U.S. Pat. No. 5,702,412 discloses a method and devices for performing end-to-side anastomoses where the side wall of one of the structures is cut from the intraluminal space of the graft vessel and the anastomosed structures can be secured by a plurality of clips or by suturing.

It has been concluded that stapled microvascular anastomosis is fast and reliable and histomorphologic examination of the anastomotic site revealed no major differences between sutured and stapled groups. *Microscopic Analysis of Stapled Microvascular Anastomosis*, p. S128. Furthermore, it has also been reported that the "clipped anastomotic technique has a rapid learning curve, the same safety as suture methods, and the potential for facilitating endoscopic vascular reconstruction." *Nonpenetrating Clips for Coronary Anastomosis*, p. S135. In a study undertaken to compare VCS clips with sutured arterial end-to-end anastomosis in larger vessels, it was concluded that this type of anastomosis "can be performed more rapidly with VCS clips than continuous sutures", and that VCS clips "are potentially useful situations where the clamp time of the vessel is critical." Emmanouil Pikoulis, David Burris, Peter Rhee, Toshiya Nishibe, Ari Leppaniemi, David Wherry and Norman Rich, *Rapid Arterial Anastomosis with Titanium Clips, The American Journal of Surgery*, Vol. 175 (1998) pp. 494–496.

Nevertheless, clipping may lead to irregularities at the junction of the anastomosed vessels. In addition, it has been reported that "both periadventitial tissue stripping and microvascular clip application have deleterious effects in the early postoperative period" and that "temporary clips with a lesser width must be used in place of microvascular clips" while performing microvascular anastomosis. S. Keskil, N. Ceviker, K. Baykaner, Ö. Uluoğlu and Z. S. Ercan, *Early Phase Alterations in Endothelium Dependent Vasorelaxation Responses Due to Aneurysm Clip Application and Related Manipulations, Acta Neurochirurgica*, Vol. 139(1) (1997) pp. 71–76.

2.2.2. Coupling

Tissue bonding by coupling with the aid of devices such as stents, ferrules, or rings without staples is considered to be older than stapling. Among the more recent devices and techniques, U.S. Pat. No. 4,523,592 discloses anastomotic coupling means capable of end-to-end and end-to-side anastomosis without resorting to suturing. The vessels are coupled with a pair of coupling disc members that cooperatively lock and secure the everted tissue from the anastomosed structures. These everted tissues remain in intima-intima contact with no foreign material exposed to the lumen of the anastomosed vessels. U.S. Pat. Nos. 4,607,637, 4,917, 090 and 4,917,091 also disclose the use of anastomosis rings and an instrument for joining vessels or tubular organs which are threaded to the annular devices before the joining. The instrument and the anastomosis rings are shaped and adapted to be utilized mainly in microsurgery. U.S. Pat. Nos. 4,657,019 and 4,917,087 disclose devices, kits and methods for non-suture end-to-end and end-to-side anastomosis of tubular tissue members that employ tubular connection members and provide intima-intira contact at the anastomosis site with no foreign material exposed to the lumen of the vessels being joined. An annuli pair that provides an anastomotic clamp and that is especially adapted for intraluminal disposition is disclosed in U.S. Pat. No. 5,336,233. Because of the intraluminal disposition, this device is exposed to the blood flow in the anastomosed vessels. U.S. Pat. No. 4,907,591 discloses a surgical instrument for use in the installation of an assembly of interlocking coupling members to achieve compression anastomosis of tubular structures. Other coupling devices include the use of intraluminal soluble stents and extraluminal glues, such as cyanoacrylates, for creating nonsuture anastomoses. Reportedly, 98% patency was obtained with these soluble polyvinyl alcohol stents. *Review of Facilitated Approaches to Vascular Anastomosis*, pp. S124–S125. An absorbable anastomotic device for microvascular surgery relies on the cuffing principle with injection-molding techniques using the polymer polyglactin. Vessel ends that are everted 180° are joined in this technique by an interconnecting collar so that an intima-intima seal is achieved. Reportedly, 96% patency was obtained with these absorbable interconnecting collars. *Review of Facilitated Approaches to Vascular Anastomosis*, p. S125.

The major advantage of a coupling microvascular anastomotic device has been reported to be the reduction in the time needed for a venous anastomosis, which decreases the total ischemic time. Maisie L. Shindo, Peter D. Constantino, Vincent P. Nalbone, Dale H. Rice and Uttan IC Sinha, *Use of a Mechanical Microvascular Anastomotic Device in Head and Neck Free Tissue Transfer, Archives of Otolaryngology—Head & Neck Surgery*, Vol. 122(5) (1996) pp. 529–532. Although a number of coupling techniques do not place any foreign body in the intraluminal space of the anastomosed vessels, it is considered that the use of a foreign rigid body such as a ring that encloses a dynamically dilating structure is a disadvantage of this type of technique. Furthermore, this type of technique is viewed as not being flexible enough for its application to significant vessel size discrepancies in end-to-side anastomosis, and the devices are characterized as being of limited availability and needed in sets of different sizes. *Microscopic Analysis of Stapled Microvascular Anastomosis*, p. S128. In addition, most coupling techniques require considerable eversion, incisions and mounting of the coupling devices that are difficult or impossible to apply endoscopically.

2.2.3. Adhesives

Pasting by applying adhesives or glues is widely employed in medicine. Several glues have been tested in anastomotic procedures, including fibrin glue, cyanoacrylic glues and photopolymerizable glues.

Fibrin glue is a biological two-component sealant comprising fibrinogen solution to and thrombin combined with calcium chloride solution. These components are typically available deep-frozen in preloaded syringes, and they are mixed during application after thawing. Commercially available fibrin glue Tissucol has reportedly been approved by the Food and Drug Administration for use in the United States. See, Thomas Menovsky and Joost de Vries, *Use of Fibrin Glue to Protect Tissue During $CO_2$ Laser Surgery, Laryngoscope* Vol. 108 (1998) pp. 1390–1393. This article will hereinafter be referred to as *"Fibrin Glue in Laser Surgery."*

The use of fibrin glue has been found to be practical in telescoping anastomoses and in microanastomoses. Satoru Saitoh and Yukio Nakatsuchi, *Telescoping and Glue Technique in Vein Grafts for Arterial Defects, Plastic and Reconstructive Surgery*, Vol. 96(6) (1995) pp. 1401–1408; Seung-Kyu Han, Sung-Wook Kim and Woo-Kyung Kim, *Microvascular Anastomosis With Minimal Suture and Fibrin Glue: Experimental and Clinical Study, Microsurgery*, Vol. 18(5) (1998) pp. 306–311. In contrast, it has been reported that the application of thrombin-based fibrin sealant (fibrin glue) to microvascular anastomoses can have noticeable deleterious effects, particularly when used in venous anastomosis. Christopher A. Marek, Lester R. Amiss, Raymond F. Morgan, William D. Spotnitz and David B. Drake, *Acute Thrombogenic Effects of Fibrin Sealant on Microvascular Anastomoses in a Rat Model, Annals of Plastic Surgery*, Vol. 41(4) (1998) pp. 415–419.

A biological procoagulant solution has been described as promising. The mixture contains bovine microfibrillar collagen and thrombin. Gary Gershony, John M. Brock and Jerry S. Powell, *Novel Vascular Sealing Device for Closure of Percutaneous Vascular Access Sites, Catheterization and Cardiovascular Diagnosis*, Vol. 45(1) (1998) pp. 82–88; Ted Feldman, *Percutaneous vascular Closure: Plugs, Stitches, and Glue, Catheterization and Cardiovascular Diagnosis*, Vol. 45(1) (1998) p. 89; Zoltan G. Turi, *Plugging the Artery With a Suspension: A Cautious Appraisal, Catheterization and Cardiovascular Diagnosis*, Vol. 45(1) (1998) pp. 90–91.

Cyanoacrylic glues tested on vessels include methyl cyanoacrylate and butyl cyanoacrylate, such as Histoacryl glue (butyl-2-cyanoacrylate). The ultra-violet polymerizable glue polyethyleneglycol 400 diacrylate has also been tested and reported that it "is able to effectively seal vessel puncture sites and anastomotic junctions without acutely augmenting local vascular thrombogenicity." G. A. Dumanian, W. Dascombe, C. Hong, K. Labadie, K. Garrett, A. S. Sawhney, C. P. Pathak, J. A. Hubbell and P. C. Johnson, *A new Photopolymerizable Blood Vessel Glue That Seals Human Vessel Anastomoses Without Augmenting Thrombogenicity, Plastic and Reconstructive Surgery*, Vol. 95(5) (1995) pp. 901–907.

Glues used in anastomotic practice face the challenges inherent to factors that include toxicity, thrombogenicity, vascular wall thinning, and mechanical strength of the joint. *Review of Facilitated Approaches to Vascular Anastomosis*, p. S125; Henk Giele, *Histoacryl Glue as a Hemostatic Agent in Microvascular Anastomoses, Plastic and Reconstructive Surgery*, Vol. 94(6) (1994) p. 897.

2.2.4. Lasers

Lasers have been used in angioplastic revascularization since about 1984. See for example, Markolf H. Niemz, *Laser Tissue Interactions*, pp. 216–221, Springer Verlag 1996, (this work will hereinafter be referred to as "*Laser Tissue Interactions*"); R. Viligiardi, V. Gallucci, R. Pini, R. Salimbeni and S. Galiberti, *Excimer Laser Angioplasty in Human Artery Disease, in Laser Systems in Photobiology and Photomedicine*, edited by A. N. Chester, S. Martellucci and A. M. Scheggi, pp. 69–72, Plenum Press, New York, 1991; Timothy A. Sanborn, *Laser Angioplasty, in Vascular Medicine*, edited by Joseph Loscalzo, Mark A. Creager and Victor Brounwald, pp. 771–787, Little Brown Co. Whereas balloon angioplasty typically fractures, compresses or displaces plaque material, laser angioplasty typically removes plaque material by vaporizing it. Lawrence I. Deckelbaum, *Cardiovascular Applications of Laser Technology, in Laser Surgery and Medicine*, edited by Carmen A. Puliafito, pp. 1–27, Wiley-Liss, 1996.

The refinement of anastomosis techniques that rely on laser has been progressing since the reportedly first use of a neodymium yttrium-aluminum-garnet laser ("Nd-YAG laser") on vascular anastomosis in 1979. Particularly in an end-to-side vascular anastomosis, the end of a graft in the form of a tubular structure is connected to the side wall of a receiving vessel so that the anastomosed end of the graft encompasses the anastomosis fenestra, or artificial window, that has been formed into the side wall of the receiving vessel. Consequently, lasers can be used in anastomoses for welding the anastomosed structures and/or for opening the anastomosis fenestra. In addition to YAG lasers, such as Nd-YAG and Ho-YAG lasers, Excimer, diode, $CO_2$ and argon lasers have also been used in vascular anastomoses.

Laser welding has been defined as the process of using laser energy to join or bond tissues. Typically, laser welding relies on photothermal effects, but efforts are being made to develop laser welding that relies on photochemical effects, where the laser radiation activates cross-linking agents that are expected to produce stronger links than those produced by photothermal welding. Lawrence S. Bass and Michael R. Treat, *Laser Tissue Welding. A Comprehensive Review of Current and Future Clinical Applications, in Laser Surgery and Medicine*, edited by Carmen A. Puliafito, pp. 381–415. (This work will hereinafter be referred to as "*Laser Tissue Welding*").

Generally, the use of lasers in anastomotic practice faces the challenges inherent to factors that include the cost of laser purchase, maintenance and training, radiation damage to surrounding tissue, aneurism formation, the need for about three or four sutures (versus the nine or ten sutures applied in conventional anastomosis), side effects of heat-induced tissue welding, and mechanical failure at the anastomosis site. *Review of Facilitated Approaches to Vascular Anastomosis*, pp. S125–S126; *Laser Tissue Welding*, pp. 407–410; Brian C. Cooley, *Heat-Induced Tissue Fusion For Microvascular Anastomosis, Microsurgery*, Vol 17(4) (1996) pp. 198–208. It has been reported, however, that the "nonocclusive Excimer laser-assisted anastomosis technique is safe and yields a high long-term patency rate in neurosurgical patients" and that there might be indications for this method in coronary bypass surgery. Cornelis A. F. Tulleken, Rudolf M. Verdaasdonk, and Hendricus J. Mansvelt Beck, *Nonocclusive Excimer Laser—Assisted End-to-Side Anastomosis, Annals of Thoracic Surgery*, Vol. 63 (1997) pp. S138–S142. (This article will hereinafter be referred to as "*Nonocclusive Excimer Laser—Assisted End-to-Side Anastomosis*"). In addition, laser anastomosis is considered to offer moderately reduced operative time, reduced skill requirements, faster healing, ability to grow, and possibly reduced intimal hyperplasia. *Laser Tissue Welding*, pp. 407–410 (further reporting on selected microvascular anastomosis studies with lasers that include $CO_2$, argon, and diode lasers). Furthermore, research is being done to replace some of the initial laser sources by other lasers that are believed to be more suitable for clinical applications. For example, recent work with the 980 nm diode laser indicates that it may "replace in the near future laser sources of older conception such as the Nd-YAG." W. Cecchetti, S. Guazzieri, A. Tasca and S. Martellucci, 980 nm *High Power Diode Laser in Surgical Applications, in Biomedical Optical Instrumentation and Laser—Assisted Biotechnology*, edited by A. M. Verga Scheggi, S. Martellucci, A. N. Chester and R. Pratesi, pp. 227–230, Kluwer Academic Publishers, Dordrecht, The Netherlands, 1996.

The $CO_2$ laser can seal blood vessels, including small blood vessels of about 0.5 mm in diameter or less and it has been used in microvascular anastomosis such as in human lympho-venous anastomosis. D. C. Dumitras and D. C. A. Dutu, *Surgical Properties and Applications of Sealed-off $CO_2$, Lasers, in Biomedical Optical Instrumentation and Laser—Assisted Biotechnology*, edited by A. M. Verga Scheggi, S. Martellucci, A. N. Chester and R. Pratesi, pp. 231–239, Kluwer Academic Publishers, Dordrecht, The Netherlands, 1996. In addition to the $CO_2$ laser which is an efficient vaporizer of tissue, other lasers that effectively vaporize tissue include the argon and the KTP/532 lasers. *Lasers—Invention to Application*, p. 106.

The argon laser has been reported to offer advantages over conventional end-to-end anastomosis procedures applied to growing vessels. Eiji Chikamatsu, Tsunehisa Sakurai, Naomichi Nishikimi, Takashi Yano and Yuji Nimura, *Comparison of Laser Vascular Welding, Interrupted Sutures, and Continuous Sutures in Growing Vascular Anastomoses, Lasers in Surgery and Medicine*, Vol. 16(1) (1995) pp. 34–40. It has also been reported that low temperature argon laser welding limits anastomotic thrombogenicity, which is thought of as a factor that may improve early patency of venous and small arterial bypass grafts. Steven B. Self, Douglas A. Coe and Jarnes M. Seeger, *Limited Thrombogenicity of Low Temperature Laser—Welded Vascular Anastomoses, Lasers in Surgery and Medicine*, Vol. 18(3) (1996) pp. 241–247.

The use of laser for medical purposes requires safety measures for protecting health care practitioners who handle the laser device and for shielding surrounding tissues and avoiding unintended radiation induced damage. Laser shield materials include layers of polymethylmethacrylate and tin-foil. See, Christine C. Nelson, Krystyna A. Pasyk and Gregory L. Dootz, *Eye Shield for Patients Undergoing Laser Treatment, American Journal of Ophthalmology* Vol. 110 (1990) pp. 39–43. Laser shield materials are known and they have been disclosed in a variety of sources such as Alex Mallow and Leon Chabot, *Laser Safety Handbook*, Van Nostrand Reinhold Co., New York (1978), and A. Roy Henderson, *A Guide to Laser Safety*, Chapman & Hall, London (1997). In particular, for example, the biological sealant fibrin glue can prevent severe damage to tissue when accidentally exposed to $CO_2$ laser radiation and intraoperative coating with fibrin glue can serve as a shield to protect arteries, veins, and nerves from accidental $CO_2$ laser exposure. Furthermore, it is considered that the use of fibrin glue for laser radiation protective processes "is especially attractive in . . . fields in which the glue is already used for sealing." *Fibrin Glue in Laser Surgery* at p. 1393.

2.2.5. Other Devices and Techniques

It is known that some anastomosis techniques combine different approaches. For example, biological glues that are based on proteins and other compounds are combined with laser radiation in laser soldering. "Laser soldering is a bonding technique in which a proteinaceous solder material is applied to the surfaces to be joined followed by application of laser light to seal the solder to the tissue surfaces." *Laser Tissue Welding*, pp. 389–392. Egg albumin, heterologous fibrin glue, and human albumin have been used as laser solders, also known as adjuvant materials for laser tissue welding. Dix P. Poppas, Theodore J. Choma, Christopher T. Rooke, Scott D. Klioze and Steven M. Schlossberg, *Preparation of Human Albumin Solder for Laser Tissue Welding, Lasers in Surgery and Medicine*, Vol. 13(5) (1993) pp. 577–580.

In an even newer technique, a chromophore is added to the solder to achieve photoenhancement effects that lead to an enhanced light absorption in the solder and not in the nontargeted tissue. Id., p. 391. In laser sealing, also known as laser-activated tissue sealing, sutured or stapled repairs are reinforced with laser solder, which is expected to provide "the strength and security of sutures and the watertightness of solder." Id., pp. 403–404.

The graft in a vascular anastomosis does not necessarily have to be an autologous blood vessel. In addition to ePTFE tubular grafts that have been referred to in a preceding subsection, several synthetic materials for vascular grafts have been used or are being developed.

Synthetic biomaterials that are being developed include polymeric materials with the proteins elastin and fibronectin. A. Maureen Rouhi, *Contemporary Biomaterials, Chemical & Engineering News*, Vol. 77(3) (1999) pp. 51–63.

ePTFE has been used with a variety of coatings. One type of coating includes fibrin glue that contains fibroblast growth factor type 1 and heparin. John L. Gray, Steven S. Kang, Gregory C. Zenni, Dae Un Kim, Petre I. Kim, Wilson H. Burgess, William Drohan, Jeffrey A. Winkels, Christian C. Haudenschild and Howard P. Greisler, *FGF-1 Affixation Stimulates ePTFE Endothelialization without Intimal Hyperplasia, Journal of Surgical Research*, Vol. 57(5) (1994) pp. 596–612; Joseph I. Zarge, Vicki Husak, Peter Huang and Howard P. Greisler, *Fibrin Glue Containing Fibroblast Growth Factor Type 1 and Heparin Decreases Platelet Deposition, The American Journal of Surgery*, Vol. 174(2) (1997) pp. 188–192; Howard P. Greisler, Claire Gosselin, Dewei Ren, Steven S. Kang and Dae Un Kim, *Biointeractive Polymers and Tissue Engineered Blood Vessels, Biomaterials*, Vol. 17(3) (1996) pp. 329–336. Another coating contains basic fibroblast growth factor in fibrin glue. M. Lanzetta, D. M. Crowe and M. J. Hickey, *Fibroblast Growth Factor Pretreatment of 1-mm PTFE Grafts, Microsurgery*, Vol. 17(11) (1996) pp. 606–611.

Other grafts comprise a synthetic biodegradable tubular scaffold, such as a vessel made of polyglactin/polyglycolic acid, that has been coated with autologous cells from a tissue culture. Toshiharu Shinoka, Dominique Shum-Tim, Peter X. Ma, Ronn E. Tanel, Noritaka Isogai, Robert Langer, Joseph P. Vacanti and John E. Mayer, Jr., *Creation of Viable Pulmonary Artery Autografts Through Tissue Engineering, The Journal of Thoracic and Cardiovascular Surgery*, Vol. 115(3) (1998) pp. 536–546.

A common feature of most conventional stapling, coupling and clipping techniques, particularly when applied to small-diameter vessels, is that they require a temporary interruption of the blood stream in the recipient vessel, a disruption that is thought to be not very well tolerated in cardiac bypass surgery. *Review of Facilitated Approaches to Vascular Anastomosis*, p. S126. In revascularization procedures of the brain, temporary occlusion of a proximal brain artery may cause brain ischemia, and consequently a non-occlusive anastomosis technique is required. *Nonocclusive Excimer Laser—Assisted End-to-Side Anastomosis*, p. 141. As the instrumentation that is needed at the anastomosis site becomes complex and cumbersome, a wider open area is needed for accessing the anastomosis site, thus leading to an increasingly invasive procedure. Furthermore, conventional anastomosis techniques are usually performed at a site that is determined by external observation of the affected area. This observation is performed at a time and in a medical setup that are different from the time and medical setup of a previous exploratory or diagnosis procedure.

Techniques that require the perforation of blood vessel tissue have raised concerns regarding intimal injury, adventitial stripping, tissue plane malalignment, and anastomotic bleeding. In addition, techniques that rely on devices that are exposed to the blood flow may lead to technical problems associated with a persistent intraluminal foreign body. These factors are thought to "contribute to both early and late anastomotic failure, particularly in the form of neointimal hyperplasia." *Nonpenetrating Clips for Coronary Anastomosis*, p. S135.

The need for completely endoscopic anastomosis procedures has been clearly expressed in the context of coronary artery bypass grafting. For example, it is currently acknowledged that "the goal of a completely endoscopic coronary artery bypass procedure has not yet been realized, and will require further technological advances." *Endoscopic CoronaryArtery Bypass Grafting*, p. 1064. Furthermore, totally endoscopic coronary artery bypass grafting "is perceived by many as the ultimate surgical model of minimally invasive coronary artery bypass grafting". Hani Shennib, Amr Bastawisy, Michael J. Mack, and Frederic H. Moll, *Computer—Assisted Telemanipulation: An Enabling Technology for Endoscopic Coronary Artery Bypass, Annals of Thoracic Surgery*, Vol. 66 (1998) p. 1060.

Minimally invasive vascular grafting according to a peripheral procedure is equally desirable, and minimally invasive active endoscopic or peripheral methods, systems and devices are specially desirable. In addition, methods, systems and devices that can be used in catheter directed as well as in non-catheter directed vascular anastomosis are particularly desirable because sometimes an occluded or damaged vessel does not permit catheterization from a point that is too far from the anastomosis site.

These methods, systems and apparatuses are specially desirable when, in particular, they are versatile enough as to be able to incorporate a plurality of the desirable features that have been discussed hereinabove while reviewing different groups of vascular anastomosis techniques. This desirability is consistent with the reported expectation that reliable methods for facilitated anastomosing of vessels will be developed by combining the best features of a variety of techniques. *Review of Facilitated Approaches to Vascular Anastomosis*, p. S126.

Each one of the afore-mentioned patents and publications is hereby incorporated by reference in its entirety for the material disclosed therein.

OBJECTS AND BRIEF SUMMARY OF THE INVENTION

Conventional anastomosis techniques do not rely on intraluminally directed anastomosis procedure. It is therefore desirable to provide methods, systems and devices for achieving intraluminally directed anastomosis.

An object of the present invention is to provide apparatus, methods, systems for performing an anastomosis through use of an intraluminally directed anvil apparatus or alternatively an externally positioned anvil apparatus.

Another object of this invention is to provide systems and apparatus that work in conjunction with an intraluminally directed anvil apparatus to anastomose vessels together.

Additionally, another object of this invention is to provide methods, systems, and devices for joining vessels together in a secure manner such that the portions defining the openings of the vessels are not penetrated.

Additionally, another object of this invention is to provide methods, systems, and devices for joining vessels together through the use of plates that are guided to each other by guides.

Still another object of the present invention is to provide methods, systems, and devices that are versatile enough to be able to suitably combine a variety of cutting, welding, and joining techniques in the practice of vascular anastomosis.

A feature of this invention is that the anvil apparatus can be positioned in a vessel intraluminally such that an anvil abuts the wall of the vessel with an anvil pull extending through an initial piercing in the vessel wall. This is preferably achieved through the use of a catheter inserted into and along the intraluminal space of a receiving blood vessel. Because the initial piercing is too small for the anvil to pass through, the anvil pull can be pulled in a manner that causes the wall of the vessel to be distended.

The opening is formed in a manner that consistently creates a complete cut having a perimeter with a desired shape such as a circle or an ellipse depending on the type of anastomosis. The precision of the cutting is due to several features. As mentioned above, the vessel wall is distended over the anvil which enables the wall to be stretched. This assists in creating a clean cut. The anvil is larger than the cutter so that the cut is formed due to the pressure between anvil and the cutter instead of forcing the vessel between the cutter and the anvil. Also, the anvil is preferably configured such that it has an engaging end that is convex and is more preferably spherical so that when engaged by a cylindrical cutter the cutter can self center on the engaging end. The cutter is also preferably spring biased which provides increased pressure for engaging the anvil.

The ability to distend the vessel wall is particularly useful when a compression plate apparatus is utilized to join the vessels. This compression plate apparatus includes two opposing and generally annular compression plates in a generally coaxial orientation. The end of the graft vessel that is to be anastomosed is everted onto one of the compression plates. The anvil pull is used to distend the receiving vessel wall such that it extends into compression plate apparatus. With the other compression plate placed at and around the anastomosis site, an anastomosis fenestra is opened in the wall of the receiving vessel. This anastomosis fenestra is opened within the annular region generally defined by the compression plate located at and around the anastomosis site. With the aid of the anvil of this invention, the contour of the anastomosed fenestra is engaged with the compression plate which opposes the compression plate that carries the graft vessel. This engagement is preferably accomplished with the aid of holding tabs protruding from the compression plate placed around the anastomosis fenestra. The degree to which the anvil has distended the receiving vessel before formation of the fenestra determines the size of the portion defining the vessel opening that remains in the compression plate apparatus. By adequately distending the receiving vessel wall, the portion defining the opening can be captured by the compression plate apparatus and everted. The graft vessel is subsequently approached to the anastomosis fenestra by reducing the separation between the compression plates, so that the graft vessel causes the eversion of the contour of the anastomosis fenestra by appropriately sliding on the surface of the anvil. Once the portion of the vessel that defines the opening has been everted then the compression plate apparatus can be compressed in a manner such that the everted portion of the receiving vessel is held against the everted portion of the other vessel such as a graft vessel. The relative separation of the compression plates is reduced to the extent necessary to bring the everted edges of the anastomosed structures into contact engagement so that a leak proof anastomosis is achieved.

A feature of the present invention is that the compression plate apparatus is suitable for end-to-side anastomosis in addition to side-to-side anastomosis. Furthermore, the compression plate apparatus of this invention provides support to the anastomosed structures in a manner such that the compression plates do not disrupt the periodic dilation of the anastomosed structures as is required by the characteristics of the blood flow that circulates therethrough. Moreover, the compression plate apparatus of this invention is used, together with the anvil, to evert the contour of the anastomosed fenestra in the receiving vessel while the anastomosis takes place. In addition, the compression plate apparatus of this invention can be used in conjunction with an anvil and anvil pull, regardless of whether the vascular anvil and wire are introduced into the receiving blood vessel with the aid of a catheter or directly into the intraluminal space through a small incision at the anastomosis site.

Another feature of the present invention is that the anvil is configured in a way such that it cooperates with the cutting element in the opening of the anastomosis fenestra and it also cooperates with the compression plate apparatus in the eversion of the edge of the anastomosed fenestra. By joining the everted contour of the anastomosis fenestra with the everted edge of the graft vessel, significant exposure to the blood flow of the cut portion of the anastomosed structures is avoided. Furthermore, the use of the anvil in a plurality of operations permits a considerable simplification of the anastomosis procedure. These operations include the abutting of the receiving blood vessel wall at the anastomosis site, the opening of the anastomosis fenestra in the receiving blood vessel, the eversion of edge of the anastomosis fenestra, and the joining of the anastomosed structures.

As discussed in more detail hereinbelow, the opening of the anastomosis fenestra can be performed mechanically or with the aid of a radiation-based device. The graft vessel is joined to the wall of the receiving blood vessel by a compression plate device. This device is configured in a manner such that it permits the use of supplementing joining techniques and combinations thereof. These techniques include welding, soldering, and gluing. Moreover, the signaling of the anastomosis site is preferably performed with the aid of a mechanical device such as the combination of a wire and an anvil.

The compression plate apparatus may be two opposing plates that are guided to each other as they are compressed together by guides which ensure that the plates maintain a parallel orientation with respect to each other. The compression plate apparatus may also be a snap-fit apparatus which ensures that the vessels are held together without penetrating the portions of the vessels that define the openings.

Many of the features obtained through the use of an intraluminally directed anvil apparatus can also be utilized in conjunction with an externally positioned anvil apparatus. For example, the advantageous cutting properties achieved with an intraluminally positioned anvil apparatus engaging a cutter as described above can also be used by an anvil apparatus that has been positioned within the lumen of a vessel by inserting the anvil through an insertion opening in the vessel.

An external anastomosis operator is also provided that controls the anastomosis procedure once the anvil pull extends out of the wall of the vessel and can be engaged. The external anastomosis operator enables the anastomosis procedure to mechanized so that it is rapidly and reliably completed in a highly controlled manner. The external anastomosis operator can also be utilized with an anvil apparatus that has been positioned externally into a vessel as well as the compression plates.

One advantage of performing a minimally invasive anastomosis under the active endoscopic or peripheral procedure that is based on the methods, systems, and devices of the present invention is that its practice does not require the training in surgical methods and techniques that the practice of surgery requires. Cross-specialty teams of practitioners including those with training in endovascular intervention as well as conventional surgical training can consequently perform minimally invasive anastomoses according to the methods, apparatuses, and systems of this invention.

Another feature of the active endoscopic or peripheral procedure of this invention is that it directly employs information while it is being acquired in an angiographic examination. This efficient use of information, and in particular imaging, has the advantage that the anastomosis is actually performed in less time and without having to rely on the correlation of previously recorded images with external anatomic inspection for locating the optimal anastomosis site. The shorter procedure according to this invention consequently requires less or no hospitalization time and less medical resources.

Still another feature of the active endoscopic or peripheral procedure of this invention is that it requires no sutures. The avoidance of sutures has the advantages of reducing the invasive character of the procedure, reducing the number of mechanical elements in the practice of the anastomosis, and shortening the time needed to perform the anastomosis.

By not requiring the interruption of blood flow in the receiving blood vessel, the active endoscopic or peripheral procedure of this invention advantageously reduces or even eliminates the risk of ischemia in organs that receive their main supply of blood through the receiving blood vessel. Furthermore, the exposure of the anastomosis area is reduced because no devices have to be introduced to temporarily interrupt blood flow. This feature advantageously enhances the minimally invasive character of the methods, systems, and apparatuses of this invention and the intervention time for the practice of the anastomosis.

The minimal disruption of blood flow in the receiving blood vessel by the active endoscopic or peripheral procedure of this invention advantageously makes it suitable in the context of coronary artery bypass grafting (CABG), whether blood circulation is intracorporeal or extracorporeal, and whether the grafting is performed on a beating heart or an arrested heart.

A feature of the catheter assisted endoscopic or peripheral procedure of this invention is the versatility of the vascular anvil and wire for signaling the anastomosis site and of the extravascular device and cooperatively performing the anastomosis. Accordingly, a variety of devices and techniques can be advantageously combined in the context of this invention to enhance the performance of its methods. systems and devices.

These and other objects, features, and advantages of the present invention will become more filly apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 9A is a perspective view of a mechanically expandable anvil.

FIG. 9B is a cross-sectional view of the anvil shown in FIG. 9A.

FIG. 10A is a perspective view of another mechanically expandable anvil.

FIG. 10B is a cross-sectional view of the anvil shown in FIG. 10A.

FIG. 12E is an enlarged partial cross-sectional view of the compression plate apparatus shown in FIG. 12D in the next phase as the graft vessel everts the portion of the blood vessel defining the first vessel opening.

FIG. 12F is a cross-sectional view of the compression plate apparatus shown in FIG. 12B in the next phase after the second compression plate has been compressed towards the first compression plate such that the everted graft vessel contacts the everted blood vessel.

FIG. 12G is a cross-sectional view of the compression plate apparatus shown in FIG. 12C with the anastomosed structure after the anvil apparatus and the cutter have been removed.

FIG. 13 is a perspective view of guided compression plate apparatus adapted for use in joining vessels at angles with elliptical openings with a graft vessel ready to be received through a cutter and loaded onto the holding tabs of the second compression plate.

FIG. 14A is a perspective view of a cutter ready to engage an anvil with a thread anvil pull extending through the cutter to an anvil pull engager to form a circular opening.

FIG. 14B is a perspective view of a cutter ready to engage an anvil with a thread anvil pull extending through the cutter to an anvil pull engager to form an elliptical opening.

FIG. 17A is a perspective view of an externally positioned anastomosis fenestra cutting apparatus inserting an anvil through an insertion opening into the lumen of a blood vessel.

FIG. 17B is a perspective view of an externally positioned anastomosis fenestra cutting apparatus distending the vessel and being readied to cooperate with an anvil.

FIG. 17C is a cross-sectional view and the anvil pull of the externally positioned anastomosis fenestra cutting apparatus shown in FIGS. 17A–17B pulling the anvil so that the engaging end of the anvil engages the cutter and forms an opening.

DETAILED DESCRIPTION OF THE PREFERRED EMBODIMENTS

The present invention focuses on vascular anastomosis methods, systems, and devices as well as related technology for forming the openings that are subsequently anastomosed together. Numerous designs are disclosed herein for achieving the desired anastomosis. The following discussion focuses mainly on the use of an intraluminally directed anvil apparatus and an external anastomosis operator that work together with various anastomosis plate apparatus to join vessels together. However, some features of the intraluminally directed anvil apparatus can also be utilized with externally positioned anvil apparatuses that are inserted into a lumen through the wall of the lumen and are then utilized. Such externally positioned anvil apparatuses are also described.

Some of the main components that are utilized in accordance with the preferred methodology for intraluminally directed anastomosis procedures include a catheter system 100 and an intraluminally directed anvil apparatus 200. The catheter system 100 is used to remotely position the intraluminally directed anvil apparatus 200 from a catheterization site to an anastomosis site. At the anastomosis site, additional main components are utilized with the intraluminally directed anvil apparatus 200 including a compression plate apparatus 300 and an external anastomosis operator 700. The methodology for using these components is initially described in the context of joining an end of an attaching vessel to a side of a receiving vessel, however, the same methodology can be used with other anastomosis procedures such as side-to-side anastomosis as also described below.

This methodology is described in the subsection below that is entitled Methodology Overview. The main components are described in detail in the Methodology Overview including the catheter system 100, the intraluminally directed anvil apparatus 200, the compression plate apparatus 300 and the external anastomosis operator 700. These components are also described and contrasted with other embodiments of these components in sections entitled Anvils, Compression plate apparatus, External Anastomosis Operators. Additional methodologies for utilizing these components and alternative embodiments of these components are described in sections entitled Side-to-Side Anastomosis, Externally Directed Anastomosis, and Externally Positioned Anastomosis Fenestra Cutting Apparatus.

Methodology Overview

Figure 1:
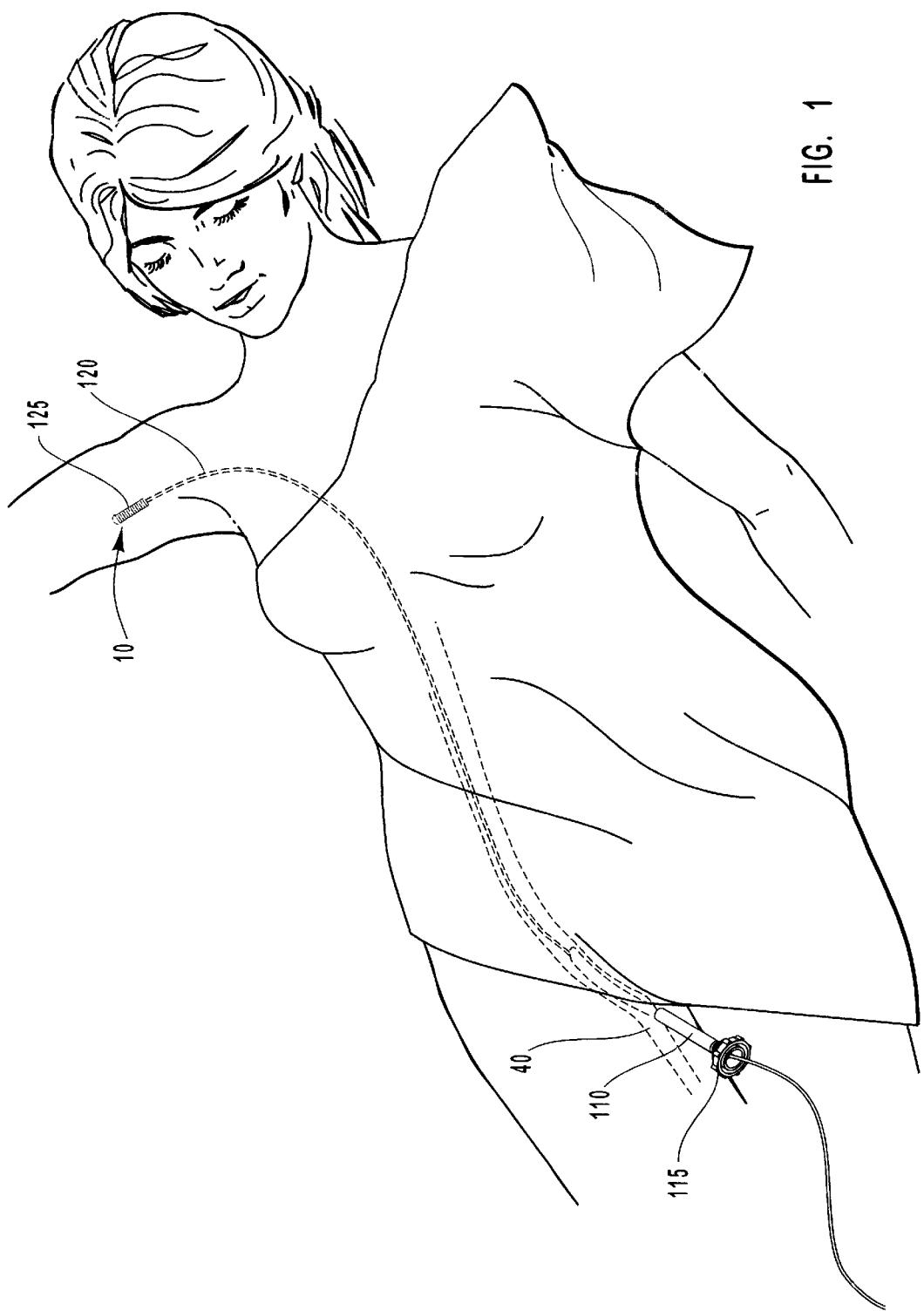
FIG. 1 is a perspective view of a patient receiving a catheter at a catheterization site as a guide wire is directed to a remote anastomosis site.

To optimally position intraluminally directed anvil apparatus 100, catheter system 100 is utilized as shown in FIG. 1 and FIGS. 2A–2F. FIG. 1 depicts a patient undergoing the initial step of a procedure utilized to remotely position the intraluminally directed anvil apparatus 200 at an anastomosis site 10 in a blood vessel 20 (not shown in FIG. 1) in the chest or arm such as the brachial artery from a catheterization site 40 in a blood vessel in the patient's leg, the femoral artery. Catheter system 100 is shown in FIG. 1 with an introducer 110 inserted at catheterization site 40 in the femoral artery. Introducer 110 permits a guide wire 120 to be inserted to the anastomosis site. Guide wire 120 preferably utilizes a coil 125 to minimize the potential of the guide wire 120 to cause damage. Guide wire 120 typically follows a fluoroscopic device, an endoscopic device or some other remote viewing instrumentation or imaging technique used to determine the location for the anastomosis site 10 such as the proximity of a blood vessel occlusion or another abnormality that has been detected by a conventional exploration technique. Any conventional guide wire suited for inserting both diagnostic and therapeutic catheters may be utilized such as those disclosed in U.S. Pat. No. 4,846,186, which is hereby incorporated by reference in its entirety, and catheters and guide wires for vascular and interventional radiology are disclosed in *Catheters, Methods, and Injectors*, at 155–174, which is also hereby incorporated by reference in its entirety.

Hub 115 is shows at the proximal end of guide wire 120 in FIG. 1. The proximal end of a catheter system such as catheter system 100 comprises one or a plurality of access ports or luer fittings such as hub 115. For the purpose of simplicity, the proximal end of the various catheters depicted in FIG. 2A–2E are not shown. However, the manufacture and handling of a catheter system with a plurality of lumens and a plurality of access ports are known to those of ordinary skill in the art. For example, U.S. Pat. Nos. 5,662,580 and 5,616,114, which have herein been incorporated by reference in their entirety, disclose catheters with a plurality of access ports or luer fittings and a plurality of lumens.

Figure 2A:
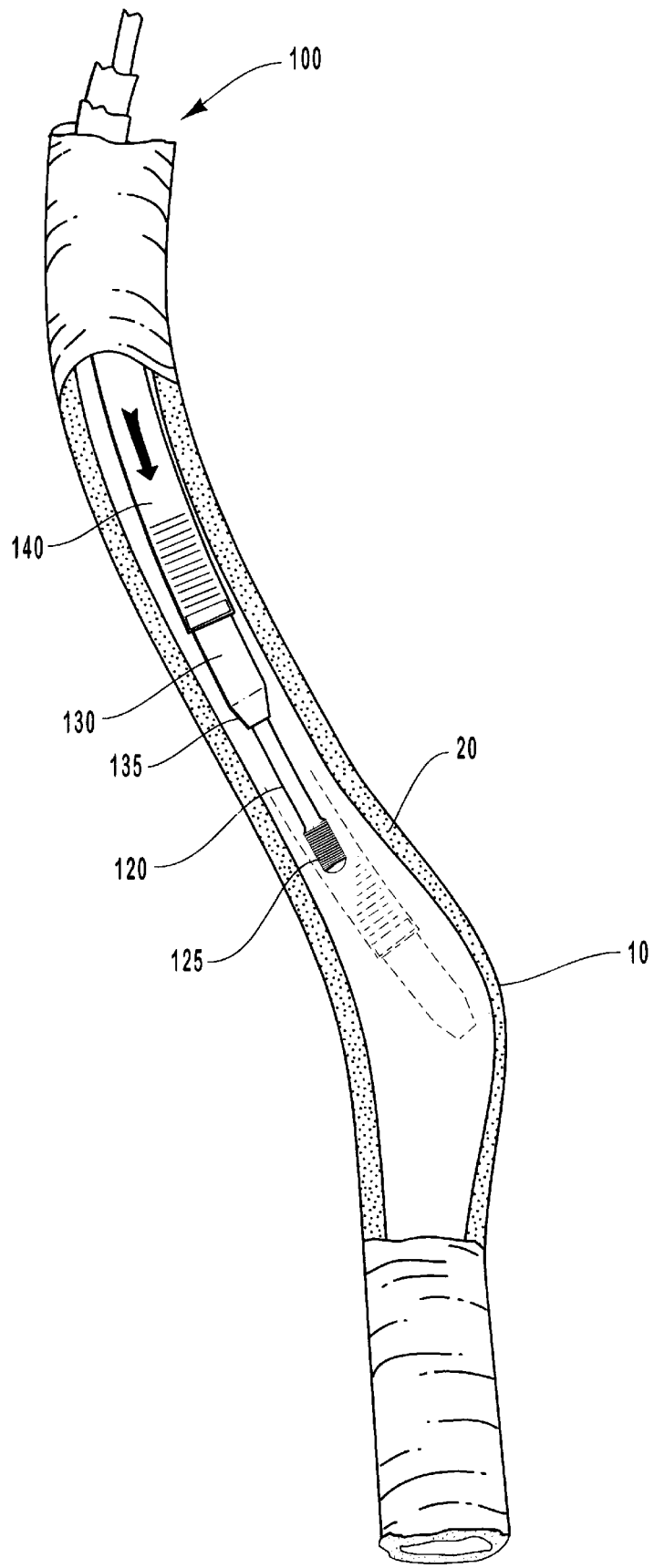
FIG. 2A is an enlarged partial cross-sectional view of a vessel with the coil of a guide wire positioned at the selected anastomosis site.

FIG. 2A is an enlarged partial cross-sectional view of vessel 20 with coil 125 of guide wire 120 positioned at the selected anastomosis site 10. Once guide wire 120 has been positioned at anastomosis site 10, then a positioning catheter 140 and a straightening catheter 130 are pushed along guide wire 120 until they reach the anastomosis site 10. Straightening catheter 130 has a tapered proximal end 135 that is adapted to minimize the impact of the positioning catheter 140 as they are advanced within a blood vessel. Once the straightening catheter 130 and positioning catheter 140 reach the anastomosis site 10, then guide wire 120 can be removed as shown by the phantom lines in FIG. 2A. Guide wire 120 is removed by pulling its distal end (not shown) that extends out of catheterization site 40 until guide wire coil 125 exits the catheterization site.

Figure 2B:
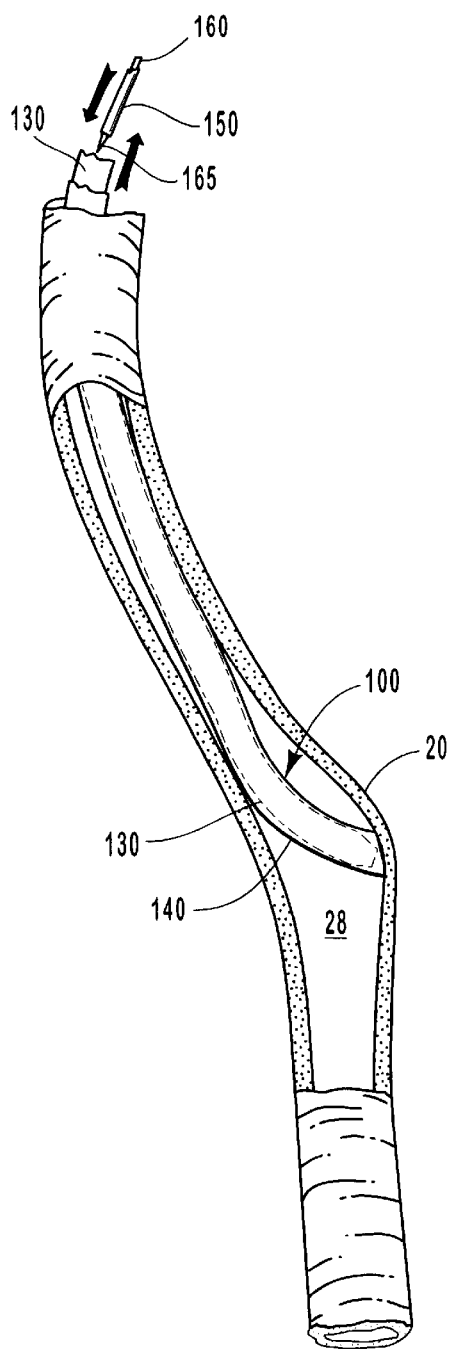
FIG. 2B is an enlarged partial cross-sectional view of the vessel shown in FIG. 2A depicting the next phase of utilizing the catheter system after a positioning catheter is positioned at the anastomosis site.

FIG. 2B depicts the next phase of utilizing catheter system 100. Positioning catheter 140 is designed to have an inherent curvature or curved memory at its distal end. In order to enable positioning catheter 140 to be moved as needed while moving through the patient's body to the anastomosis site, straightening catheter 130 extends within positioning catheter 130 in order to straighten positioning catheter 140. Guide wire 120 also assists in providing resistance to the inclination of the distal end of the positioning catheter 130 to curve. Once anastomosis site 10 has been reached and the guide wire 120 has been removed, then catheter system 100 appears as shown in FIG. 2A. The straightening catheter 130 is then withdrawn as shown in FIG. 2B, to permit the distal end of the positioning catheter 140 to curve against the wall of blood vessel. An arrow is shown in FIG. 2B to indicate that a penetration catheter 150 containing a penetration wire 160 is inserted into straightening catheter 140. The straightening catheter can be removed at this point as indicated by the arrow in FIG. 2b or it can remain.

Figure 2C:
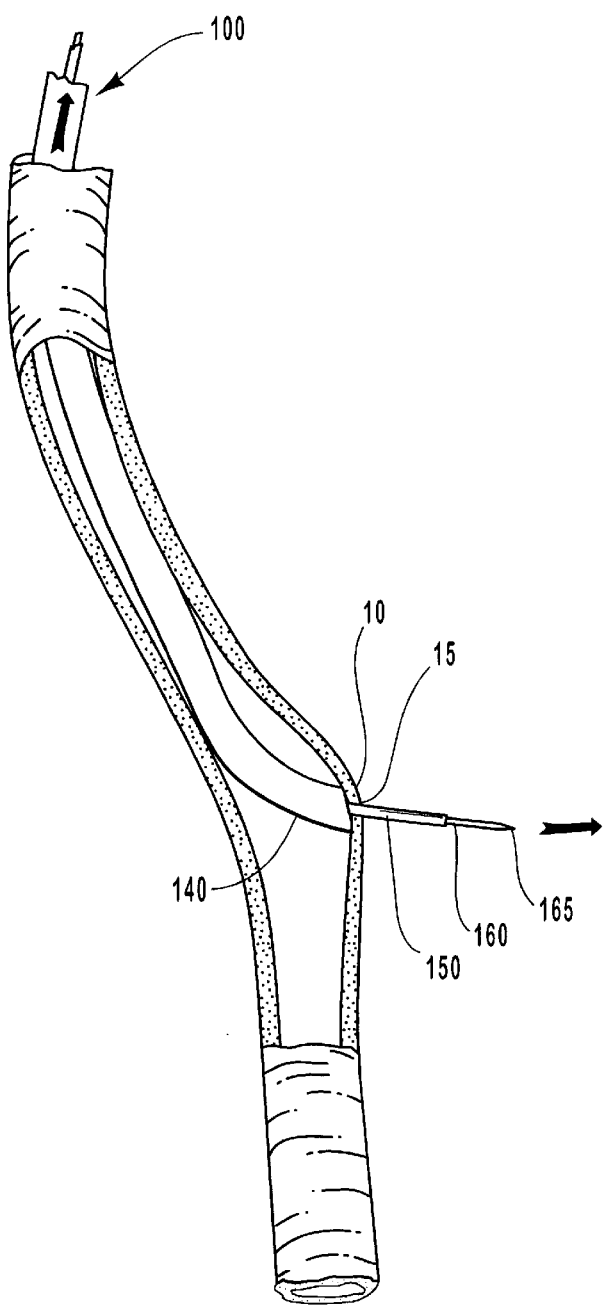
FIG. 2C is an enlarged partial cross-sectional view of the vessel shown in FIG. 2B depicting the next phase of utilizing the catheter system as the penetration catheter and the penetration wire extending through an initial piercing at the anastomosis site.

FIG. 2C depicts penetration catheter 150 and penetration wire 160 extending through an initial piercing 15 at anastomosis site 10 through the wall of blood vessel 20. Penetration wire 160 has a distal end 165 that is sharp and pointed to enable it to pierce through the blood vessel wall. Once the pointed distal end 165 of penetration wire 160 has pierced through the blood vessel wall then penetration catheter 150 can also be pushed or pulled through the blood vessel wall.

Figure 2D:
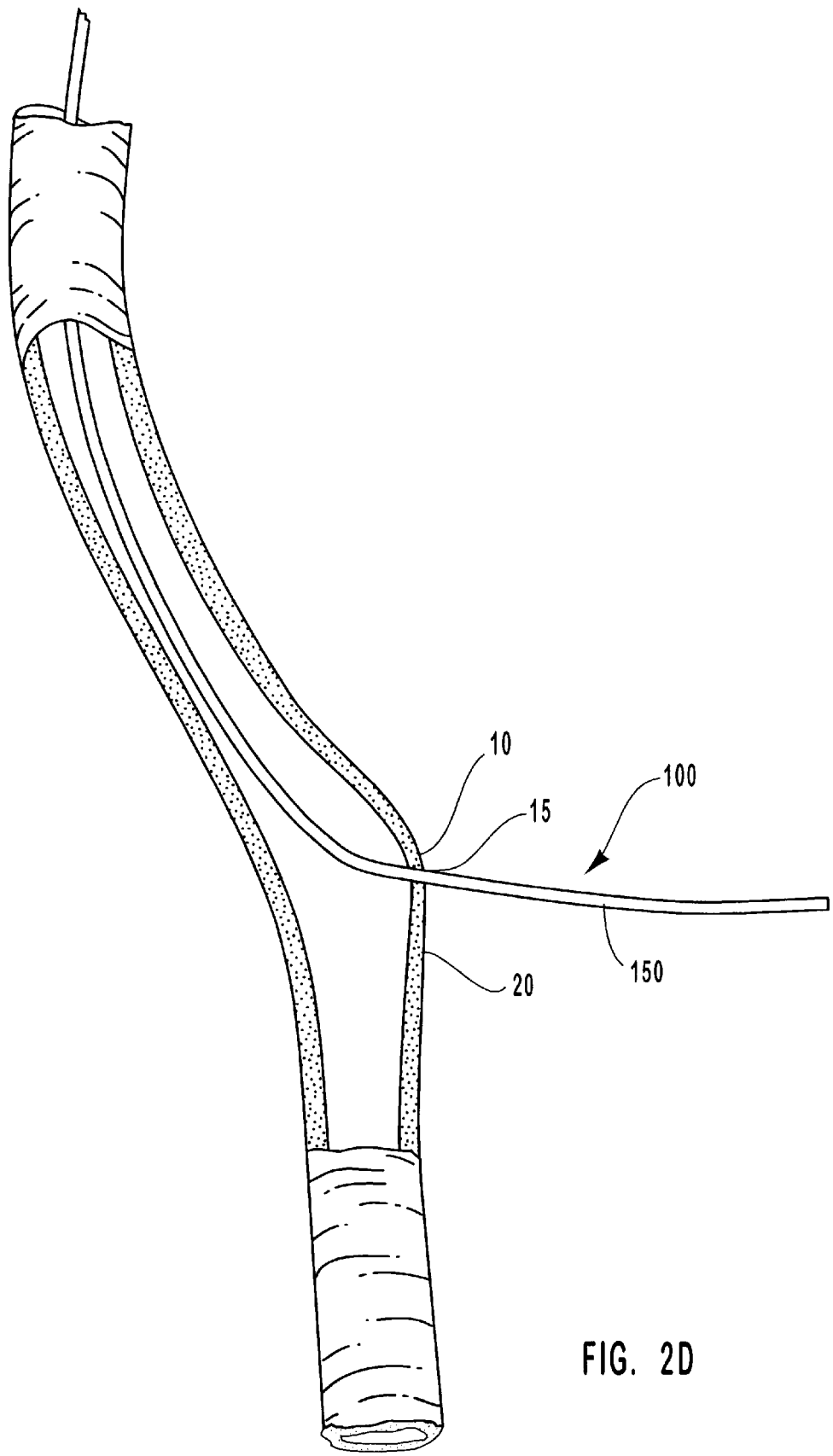
FIG. 2D is an enlarged partial cross-sectional view of the vessel shown in FIG. 2C depicting the next phase of utilizing the catheter system after the penetration wire has been removed so that only the penetration catheter remains.

FIG. 2D depicts catheter system 100 once positioning catheter 130 and straightening catheter 140 have been removed from around penetration catheter 150 and once penetration wire 160 has been removed from within penetration catheter 160. At this point, penetration catheter 150 extends from catheterization site 40 (not shown in FIG. 2D) to anastomosis site 10 through the wall of blood vessel 20 at initial piercing 15. Catheter system 100, more particularly, penetration catheter 150 of catheter system 100 can then be used in association with the intraluminally directed anvil anastomosis apparatus 200.

Figures 2E, 2F:
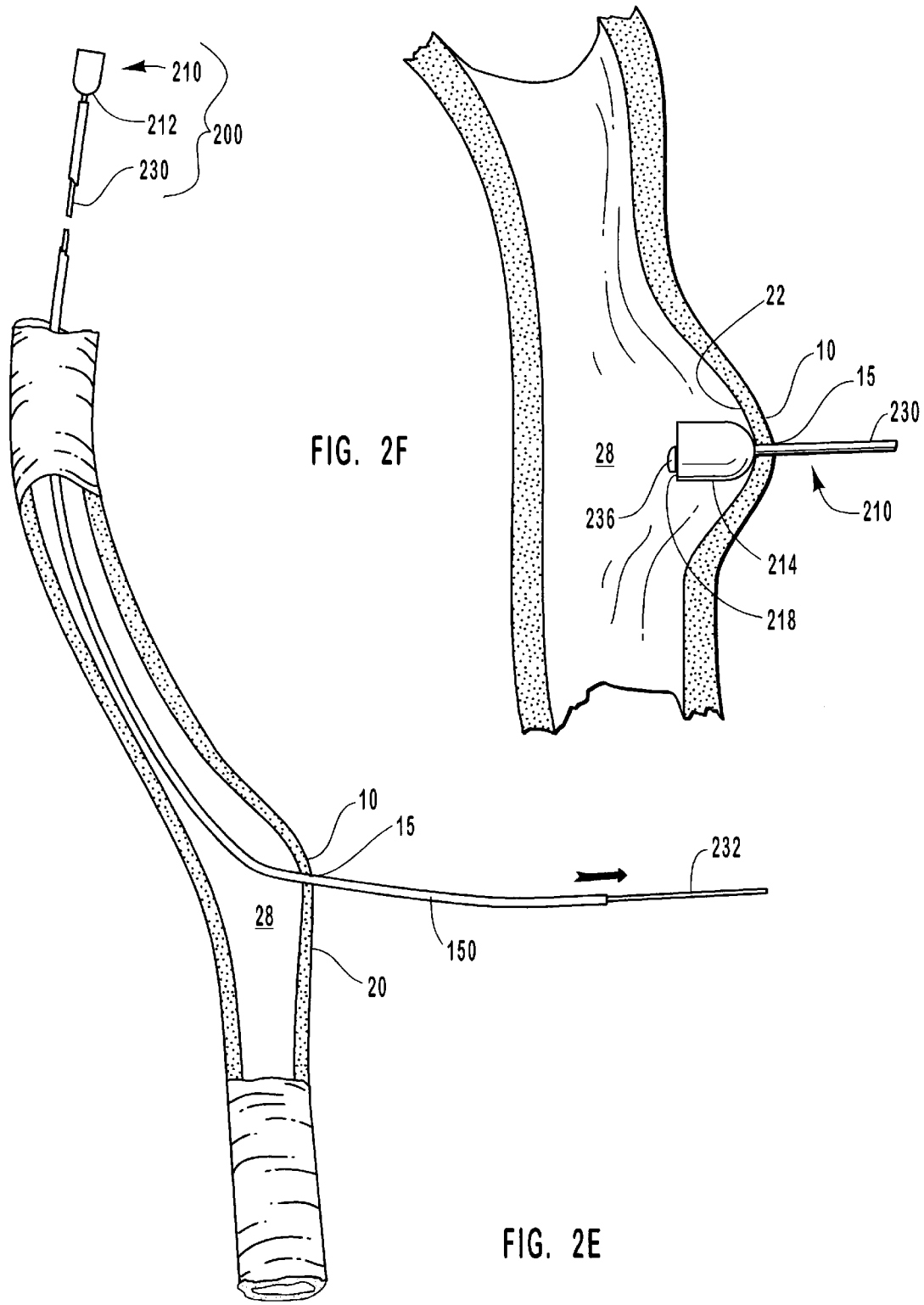
FIG. 2E is an enlarged partial cross-sectional view of the vessel shown in FIG. 2D depicting the next phase of utilizing the catheter system as an anvil pull of an intraluminally directed anvil apparatus is inserted through the penetration catheter.
FIG. 2F is an enlarged partial cross-sectional view of the vessel shown in FIG. 2E after the anvil pull of an intraluminally directed anvil apparatus has been pulled through the wall of the vessel 20 so that the anvil is brought into contact with the interior of the vessel.

FIG. 2E shows penetration catheter 150 with its proximal end in a partial broken view to indicate that the anvil pull 230 of the intraluminally directed anvil apparatus 200 has been inserted into penetration catheter 150 such that anvil pull 230 extends through penetration catheter 150 from the proximal end of penetration catheter 150 at the catheterization site 40. Intraluminally directed anvil apparatus 200, referred to in abbreviated form as an anvil apparatus, includes an anvil 210 having an engaging end 212 from which the anvil pull 230 extends. Once the distal end 232, referred to herein as a penetration end of anvil pull 230, extends beyond the distal end of penetration catheter 150, then penetration end 232 alone or in combination with the distal end of penetration catheter 150 can be grasped so that the engaging end 212 of anvil 210 is brought into contact with the interior, specifically the intima, of the vessel.

As shown in FIG. 2F, once the engaging end 212 of anvil 210 is brought into contact with the interior 22 of the wall of vessel 20 then penetration catheter 150 is removed. At this point, all components of catheter system 100 have been removed and only anvil 21 0 of anvil apparatus 200 remains in the lumen 28 of vessel 20.

The length of anvil pull 230 and the length of the various elements of catheter system 100 are suitably chosen depending on the distance from the catheterization site to the anastomosis site. For example, this length would be approximately 180 cm long, depending on the patient's height, if an anastomosis were to be performed in a blood vessel in the arm such as the brachial artery, and catheter apparatus 100 were inserted into the femoral artery.

In another embodiment of an anvil apparatus 200' described below in reference to FIG. 9, the anvil apparatus may be positioned through the use of a catheter system that comprises only a single catheter such as positioning catheter 140. Since anvil apparatus 200' is positioned at an anastomosis site by passing through a catheter such as positioning catheter 140, it is necessary for the catheter to have dimensions that accommodate the diameter or width of the anvil to be inserted. In some of the experiments performed in the context of this invention, a catheter characterized as a 13 French sheath, also known as a 4.3 mm catheter —1 French unit=⅓ mm—, has been found suitable for most anvil apparatus insertions. Catheterization techniques are described, for example, by Constantin Cope and Stanley Baum, *Catheters, Methods, and Injectors for Superselective Catheterization*, in Abrams' Angiography, edited by Stanley Baum, 4th ed., (this work will hereinafter be referred to as "*Catheters, Methods, and Injectors*") which is hereby incorporated by reference in its entirety. However, as described above, it is preferable to utilize an anvil apparatus such as anvil apparatus 200 and to position the anvil against the wall of the blood vessel by pulling the anvil pull 230 after it has been inserted into a penetration catheter 160. Penetration catheter need only be a 5 French sheath to receive the anvil pull 230 of most anvil apparatus.

FIG. 2F shows that once anvil apparatus 200 has been positioned at anastomosis site 10 such that anvil pull 230 extends out of blood vessel 20 through initial piercing 15 in the wall of the first vessel then anvil pull 230 can be maneuvered to hold engaging end 212 of anvil 210 against interior 22 of the wall of blood vessel 22. Note that since initial piercing 15 is so much smaller than engaging end 212 of anvil 210, anvil 210 cannot pass through initial piercing 15. This difference in size enables anvil 210 to be pulled against interior 22 in a manner such that the wall of vessel 20 can be distended. As discussed below, the ability to pull anvil pull 230 such that engaging end 212 of anvil 210 engages interior 22 and distends the wall of vessel 20 contributes significantly to the ability to evert the portions of the vessel wall around an opening or anastomosis fenestra used for attaching another vessel. Anvil 210 also has a cylindrical landing 214 which are its sidewall surfaces that assist in the eversion process as described below in reference to FIGS. 4A–4D.

Anvil 210 and anvil pull 230 are preferably fixedly attached together. As shown, anvil pull 230 extends through anvil 210 via an anvil aperture 216 (not shown) and terminates at a stopping element 236. Since the anvil pull is typically metal and the anvil is typically molded plastic, stopping element 236 may be just the proximal end of anvil pull 230 embedded in anvil 210 such that it is still visible. Of course, the proximal end may be embedded in a way such that it is not visible as shown in FIG. 9B. In the embodiment shown in FIG. 2F, the stopping element 236 is the proximal end of anvil pull 230 that has been bent so that it is partially embedded in terminal end 218 of anvil 210. As described below, anvil 210 and anvil pull 230 may also be integral. Additionally, anvil 210 may be movably positioned on anvil pull 230 in which case, stopping element 23 can be used to brace against terminal end 218 of anvil 210.

After the anvil 210 been positioned such that its engaging end 212 contacts the intima of vessel 20 with anvil pull 210 extending through the wall of vessel 20, then anvil apparatus is ready to be utilized in an anastomosis procedure for joining vessel 20 with another vessel such as graft vessel 50 which may be any synthetic graft vessel such as ePTFE tubular grafts. Numerous approaches are disclosed herein for joining a portion of a first vessel that define a first vessel opening to a portion of a second vessel that defines a second vessel opening such that the first vessel and the second vessel are anastomosed together and are in fluid communication. A preferred approach involves the use of compression plates that provide for a desired degree of eversion of the vessels without requiring penetration of the vessels. An example of such compression plates is the guided compression plate apparatus shown in FIG. 3A. Guided compression plate apparatus 300 is described in greater detail under the section titled Compression plate apparatus.

Figure 3A:
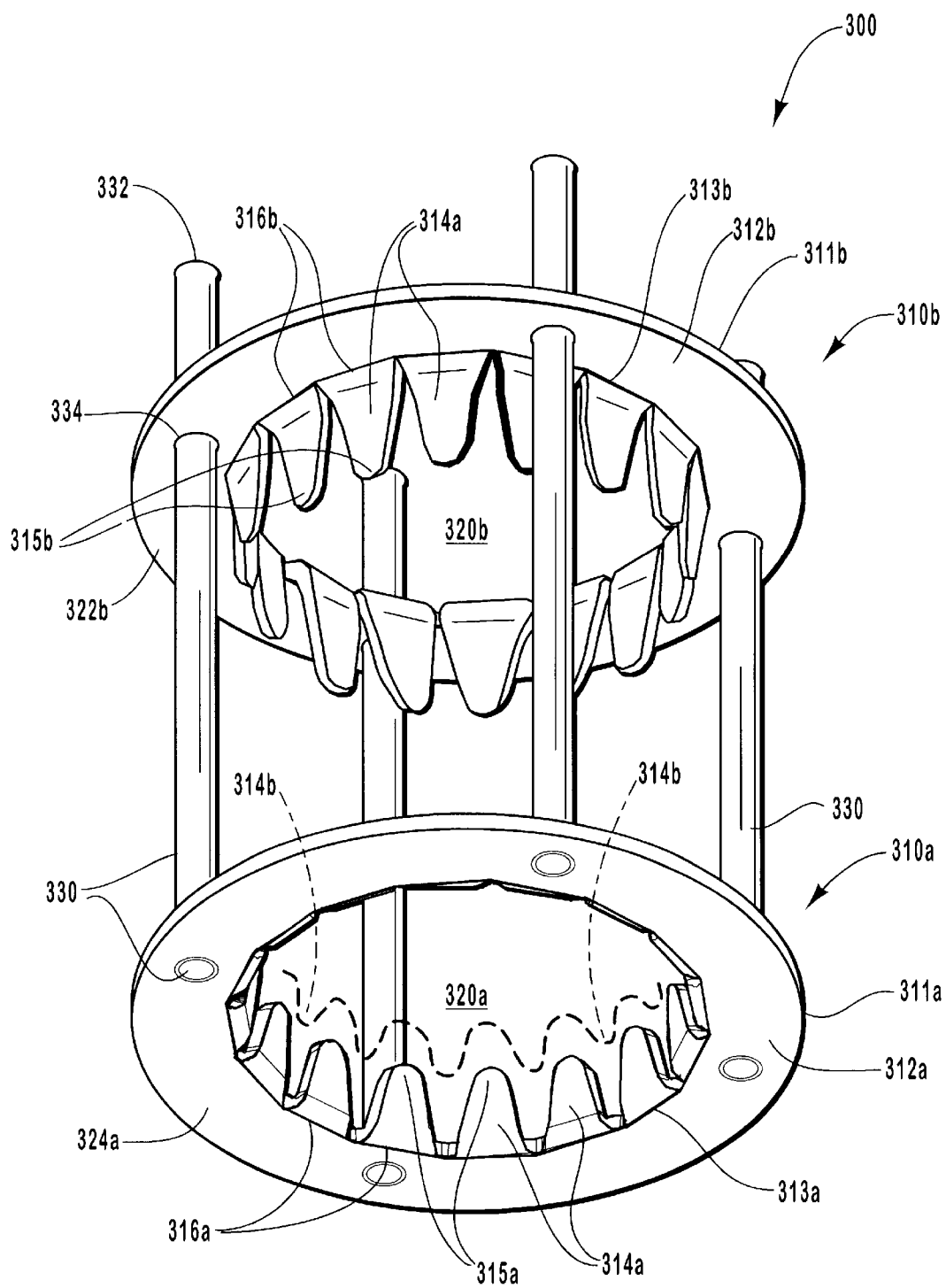
FIG. 3A is a perspective view of a guided compression plate apparatus with phantom lines to show the compressed position.
Figure 3B:
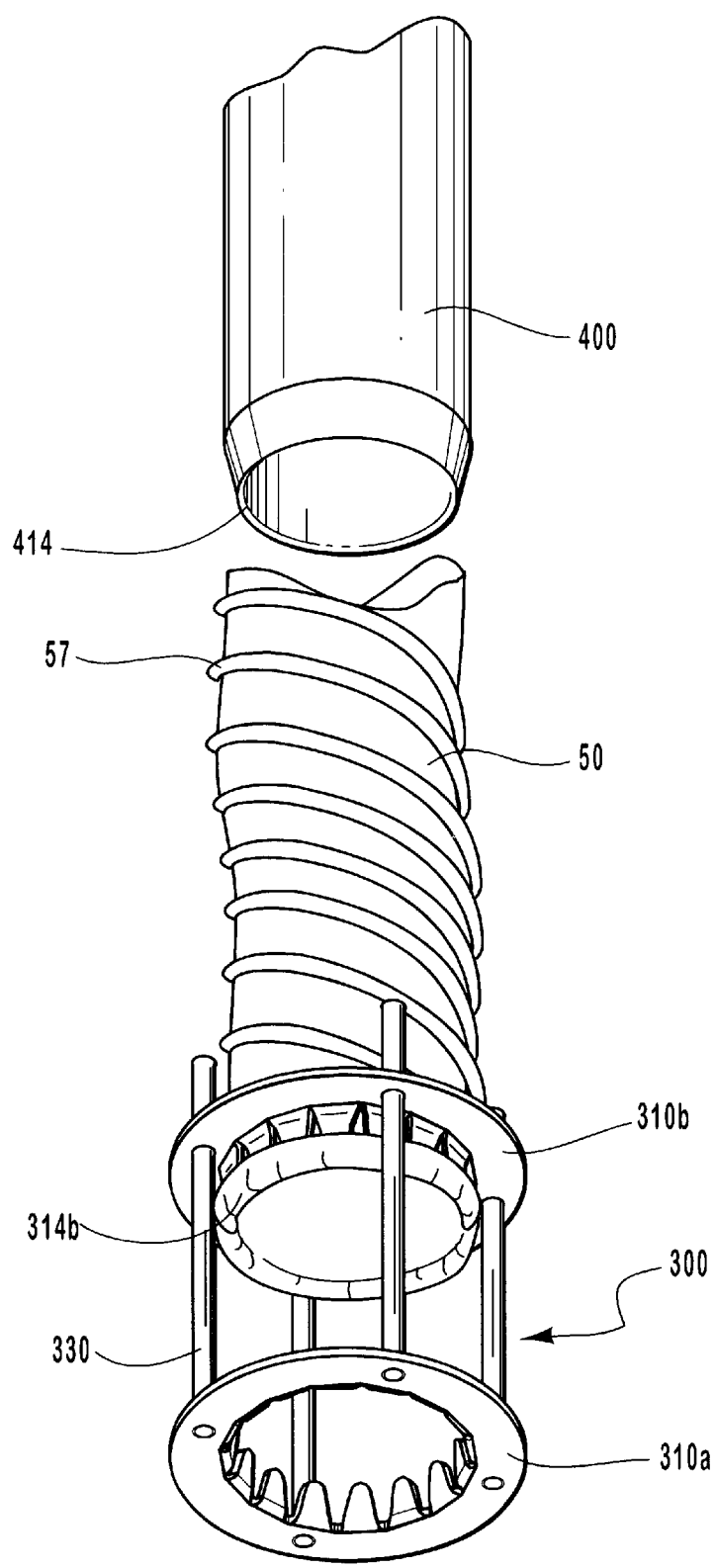
FIG. 3B is a perspective view of the guided compression plate apparatus shown in FIG. 3A with a graft vessel loaded onto the holding tabs of the second compression plate and a cutter positioned to be loaded into the lumen of the graft vessel.

As can be seen from FIG. 3B, a graft vessel 50 is loaded onto holding tabs 314b of compression plate 314 while a cutter 400 is positioned to be loaded into the lumen 58 of graft vessel 50. Cutter 400 includes a cutting tube 410 that terminates at a cutting knife 412 with a cutting edge 414. Note that a variety of cutters are disclosed herein as discussed in the section entitled Cutting Devices. Once cutter 400 is positioned within graft vessel 50 as shown in FIG. 3C, then the combination of compression plate apparatus 300, graft vessel 50 and cutter 400 are ready for use with anvil apparatus 200 to form an anastomosis. This combination is referred to herein as compression plate and cutter assembly 390 and is used much like a cartridge in the external anastomosis operator 700.

Figure 4A:
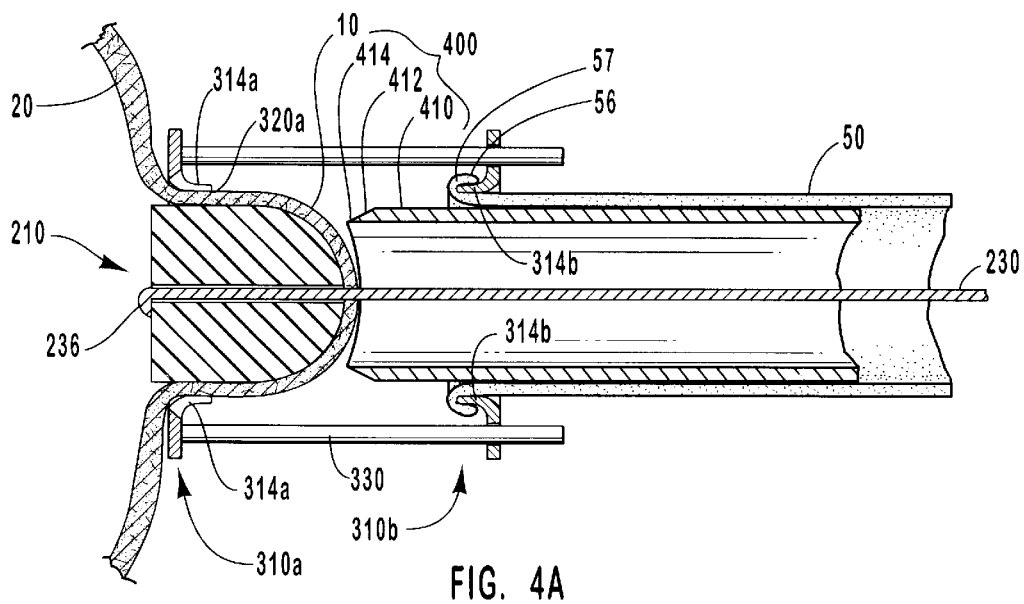
FIG. 4A is a cross-sectional view of the compression plate apparatus shown in FIG. 3A as anvil apparatus distends a blood vessel into the compression plate apparatus.

FIGS. 4A–4D depict the use of a compression plate apparatus 300 in combination with a cutter 400 and anvil 210 in the sequential order according to the preferred methodology. To optimally present this sequence, FIGS. 4A–4D are cross-sectional views. FIG. 4A depicts anvil 210 being pulled against the intima or interior of the vessel wall such that vessel 20 is sufficiently distended to permit the vessel 20 at anastomosis site 10 to be pulled into compression plate apparatus 300 through first compression plate opening 320a. More particularly, anvil 210 is pulled by anvil pull 230 such that all of spherical engaging end 212 is pulled into the compression plate apparatus 300 and most of cylindrical landing 214. Cutter 400 also is shown in FIG. 4A extending through second compression plate opening 320b about half way through compression plate apparatus 300 as cutter 400 is approximated with the portion of the blood vessel 20 distended by anvil 210.

Figure 4B:
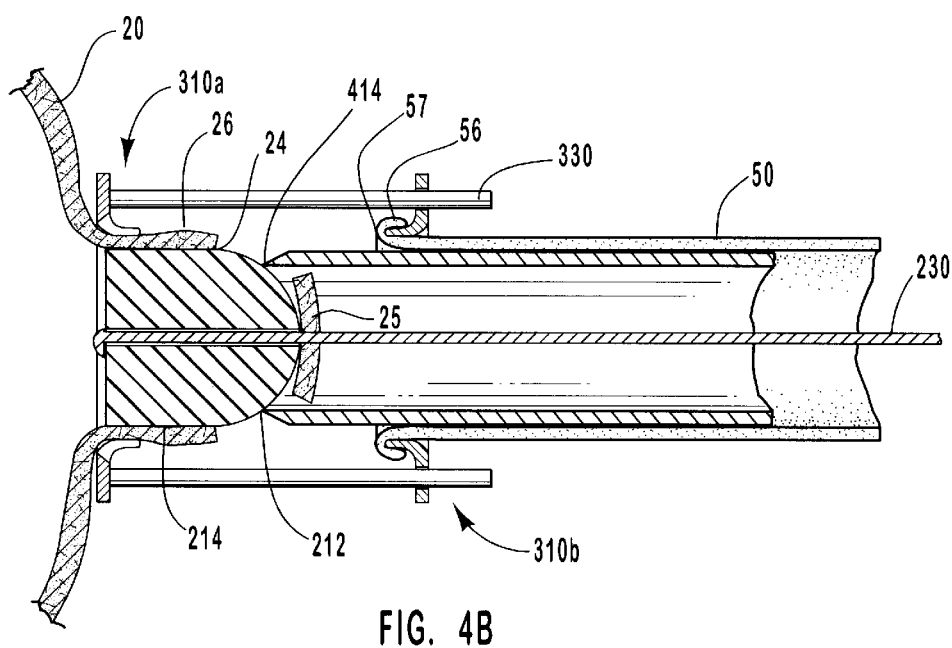
FIG. 4B is a cross-sectional view of the compression plate apparatus shown in FIG. 4A in the next phase as a cutter and an anvil are engaged to form an opening in the vessel.

FIG. 4B depicts the formation of a first vessel opening 24 in the wall of the first vessel. First vessel opening 24 is formed by pulling anvil pull 230 through cutter 400 sufficiently to enable anvil 210 to advance blood vessel 20 against cutting edge 414. After the cut has been made then a cut portion 25 of the wall of blood vessel 20 remains on spherical engaging end 212 of anvil 210 while the portion 26 of the blood vessel that now define first vessel opening 24 rest on anvil landing 214. As will be discussed in the Cutting Devices section and the External Anastomosis Operator section, cutter 400 is preferably spring biased.

Figure 4C:
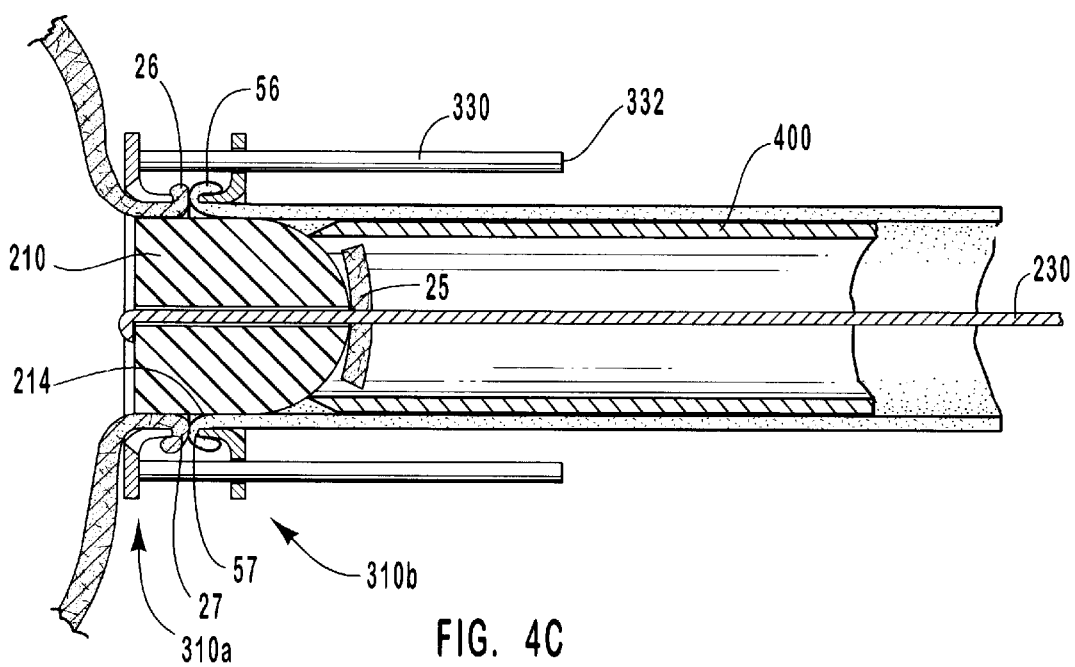
FIG. 4C is a cross-sectional view of the compression plate apparatus shown in FIG. 4B in the next phase after the second compression plate has been compressed towards the first compression plate such that the everted graft vessel contacts the everted blood vessel.

FIG. 4C depicts compression plate apparatus 300 after compression. More particularly, compression plate 310b has been moved toward compression plate 310a by sliding on guides 330 that extend from compression plate 310a. Note that the everted portion 56 of graft vessel 50, more particularly the portion 57 opposite from the rounded tip 316b, is urged against portion 26 that defines first blood vessel opening 24 in a manner such that portion 26 has been everted The end result is that the portion 27 opposite from rounded tip 316a is held in contact with the portion 57 of vessel 50 opposite from distal rounded tip 316b.

Figure 4D:
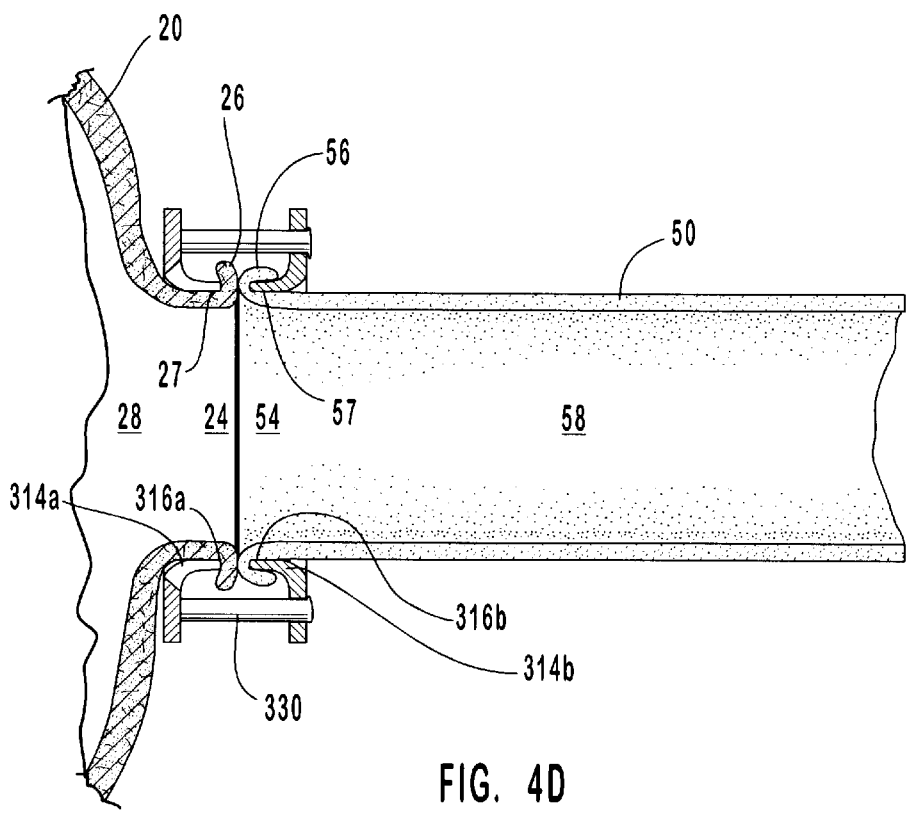
FIG. 4D is a cross-sectional view of the compression plate apparatus shown in FIG. 4C with the anastomosed structure after the anvil apparatus and the cutter have been removed.

As shown in FIG. 4D, after compression plate apparatus 300 has been compressed to join portion 26 of blood vessel 20 that defines first vessel opening 24 to portion 56 of second vessel 50 that defines graft vessel opening 54 then first vessel 20 and second vessel 50 are anastomosed together and are in fluid communication. Anvil apparatus 200 and cutter 400 have been removed upon the completion of the procedure through lumen 58 of graft vessel 50. More particularly, once the anastomosis is completed then anvil pull 230 is pulled so that it draws anvil 210 through openings 320a and 320b of compression plate apparatus 300 such that anvil apparatus 200 is removed along with cutter 400 through lumen 58. Note that terminal ends 332 of guides 330 have been removed since they are no longer necessary.

Compression plate 310b does not slide on guides 330 after being compressed due to a frictional engagement. Several methods for achieving this frictional engagement are described below in the Compression Plate Apparatus section below. Compression plate apparatus 300 utilizes a simplistic and yet effective frictional engagement as the guide apertures 334 in guide plate 310b are sized such that significant force is required to move plate 310b on guides 330.

There are significant advantages to combining vessels in accordance with the methodology described above especially in a manner such that there is at least partial eversion, contact between the everted surfaces and no penetration of the portions of the vessels defining the vessel openings. Of course, the anastomosis is fluid tight to normal systolic pressure and remains intact under stress. Since the everted portions 26 and 56 respectively cover the holding tabs 314a–b, no intraluminal foreign material is exposed and no subintimal connective tissue is intraluminally exposed. As a result, the thrombogenicity of the anastomoses is no greater than that of hand sutured anastomosis. Additionally, the configuration also results in an anastomosis that is morphologically satisfactory, including complete eversion of the receiving blood vessel intima with apposition to graft vessel. Further, everted portions 26 and 56' are in intima-intima contact and no cut portion is significantly exposed to the blood flow that is to circulate through the anastomosed structures.

In addition to the results achieved, there are also significant procedural advantages. The method does not require temporary occlusion of blood flow to the target blood vessel. The anastomosis can be reliably created. Additionally, the anastomosis is rapidly achieved and eliminates the need for high skilled suturing. For example, once the anvil pull extends through the wall of the vessel, the anastomosis procedure can be accomplished in as little as 60 seconds when compression plates are used to join the vessels.

Manual manipulation may be utilized to achieve the steps shown in FIGS. 4A–4D, however, mechanization is preferred. More particularly, anvil pull 230 may be manually pulled as cutter 400 is held or manually advanced. Additionally, compression plate apparatus may be manually compressed in some embodiments. Accordingly, components are not depicted in FIGS. 4A–4D for achieving these steps. However, as discussed in detail in the Compression Plate Apparatus section, Cutting Devices sections, and in the External Anastomosis Operator section, these steps are preferably achieved through the use of devices specifically adapted for these purposes.

Figure 5A:
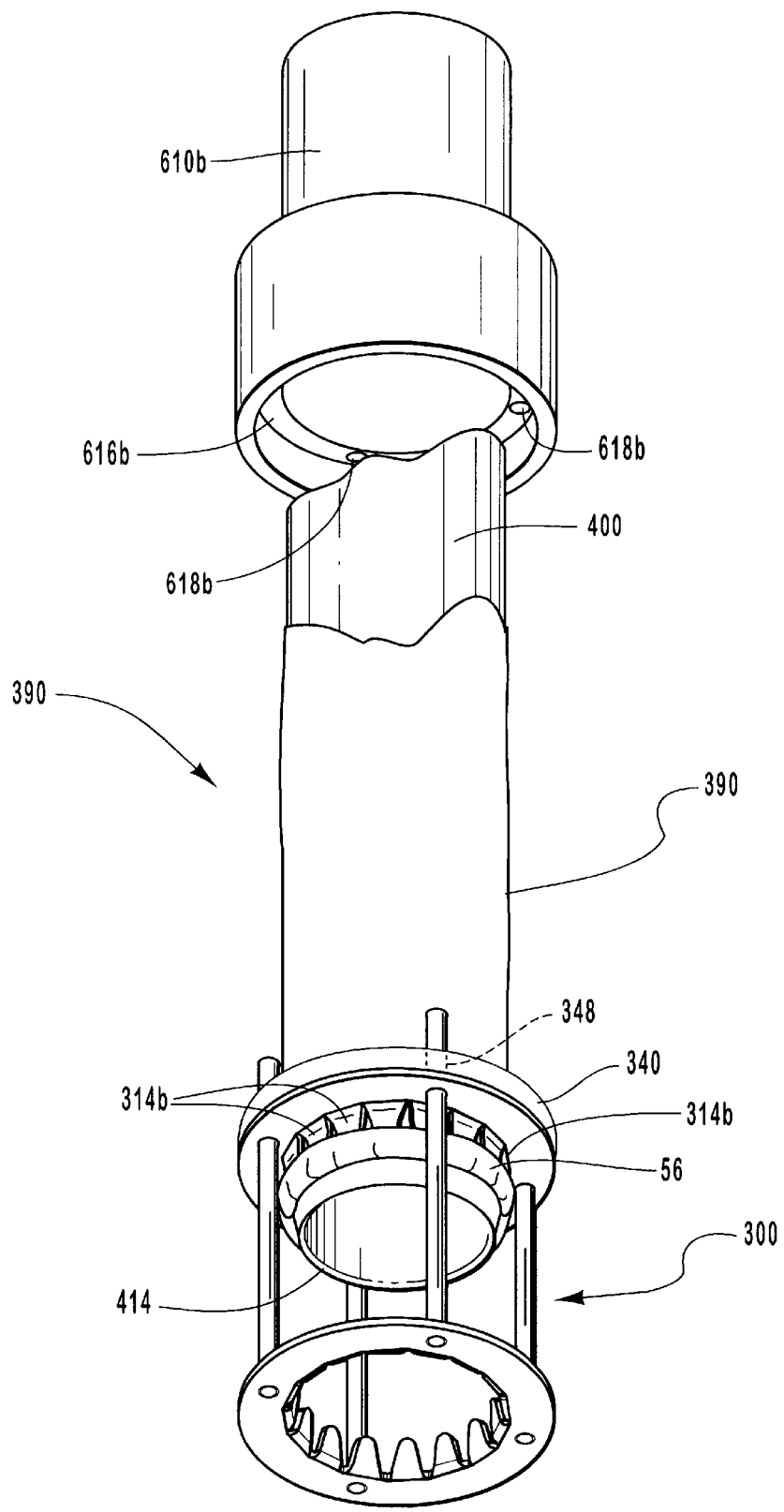
FIG. 5A is a perspective view of the guided compression plate apparatus shown in FIG. 3A with a graft vessel loaded onto the holding tabs of the second compression plate, a cutter positioned in the lumen of the graft vessel and an adapter ready to be positioned on the second compression plate.
Figure 5B:
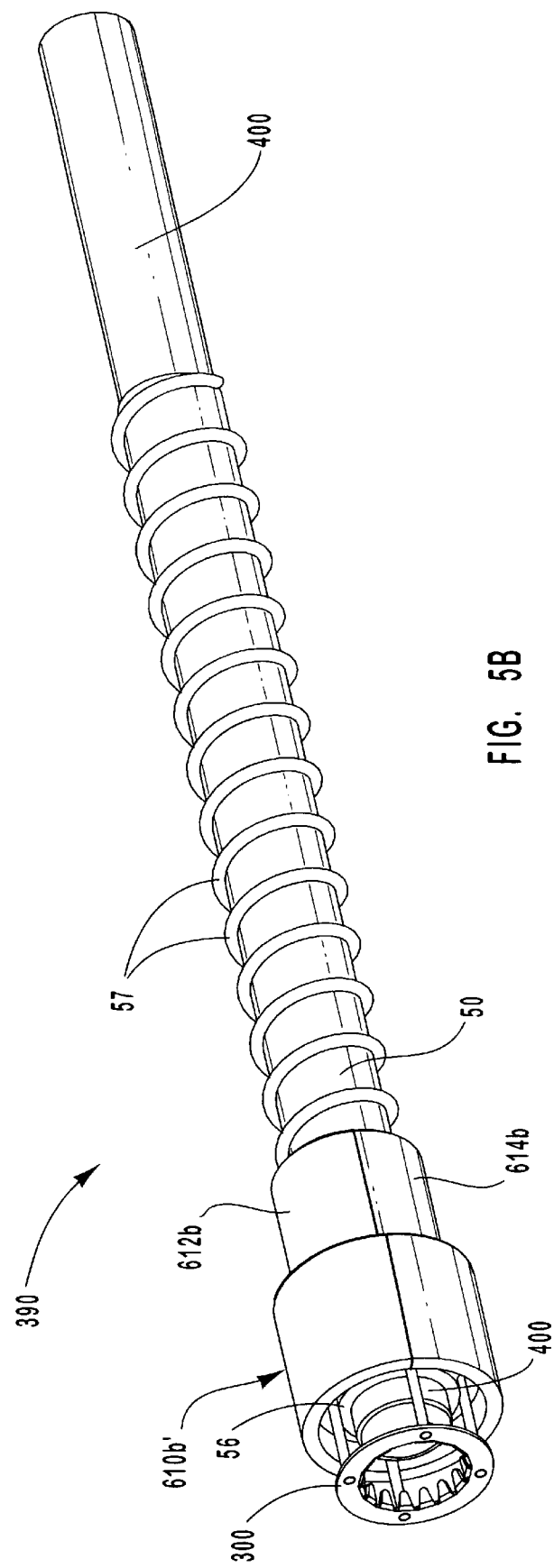
FIG. 5B is a perspective view of the guided compression plate apparatus shown in FIG. 3A with a graft vessel loaded onto the holding tabs of the second compression plate, a cutter positioned in the lumen of the graft vessel and an adapter positioned on the second compression plate.

FIGS. 5A–5B depict the use of an. optional second compression plate adaptor 610b in combination with compression plate and cutter assembly 390 as shown in FIG. 3B in preparation for use with the external anastomosis operator shown in FIGS. 6A–6E at 700. The purpose of optional second compression plate adaptor 610b is described below in relation to the attachment actuation device 600. Note that there is a cross-sectional view of compression plate and cutter assembly 390 and optional adaptor 610b in FIG. 6C.

Figure 6A:
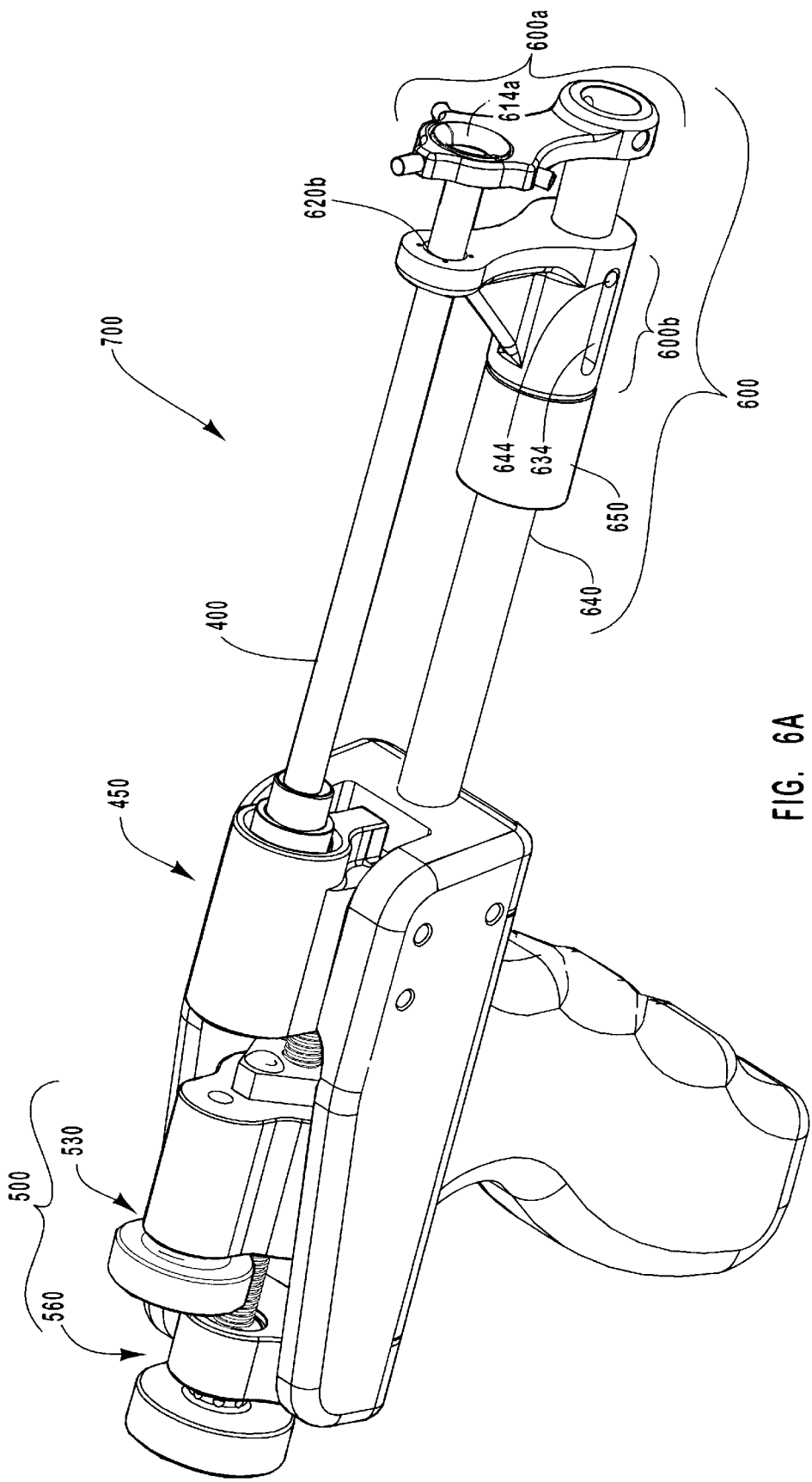
FIG. 6A is a perspective view of an external anastomosis operator.

FIG. 6A provides a perspective view of external anastomosis operator 700 with its main components identified including: cutter 400, spring biasing device 450, an anvil pull engager 500 which includes an anvil pull holder 530 and an anvil pull advancer 560, and an attachment actuation device 600. Spring biasing device 450 is used to apply pressure against the distal end 418 of cutter 400. The advantages of using a spring biased cutter are explained below in the Cutting Devices section. Anvil pull 230 is fed through cutter 400, through spring biasing device 450 and into an anvil pull holder 530. An anvil pull holder 530 is preferably a clamp assembly adapted to hold anvil pull 230 extending from anvil 210 such that holder 530 is locked into position on anvil pull 230. Anvil pull advancer 560 is adapted to pull anvil pull 230 once anvil pull 230 is held by holder 530. As anvil pull advancer 560 pulls on anvil pull 230, it causes anvil pull 230 to advance within compression plate assembly 300 and distend the wall of vessel 20 until cutter 400 is engaged. Anvil pull holder 530 and anvil pull advancer 560 are described in greater detail below in the External Anastomosis Operator section in reference to FIGS. 6A–6E.

Figure 6B:
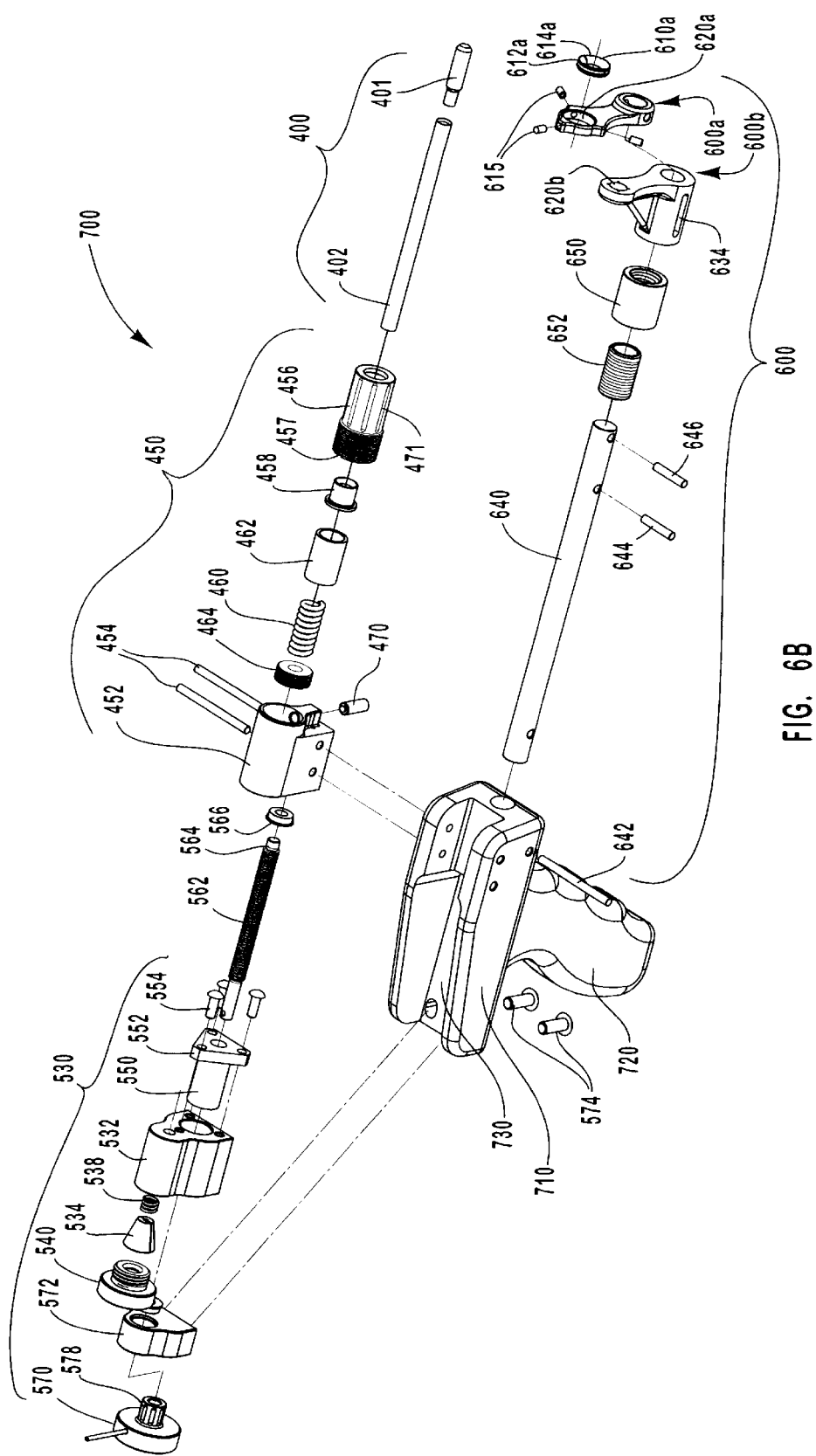
FIG. 6B is an exploded perspective view of the external anastomosis operator.
Figure 6C:
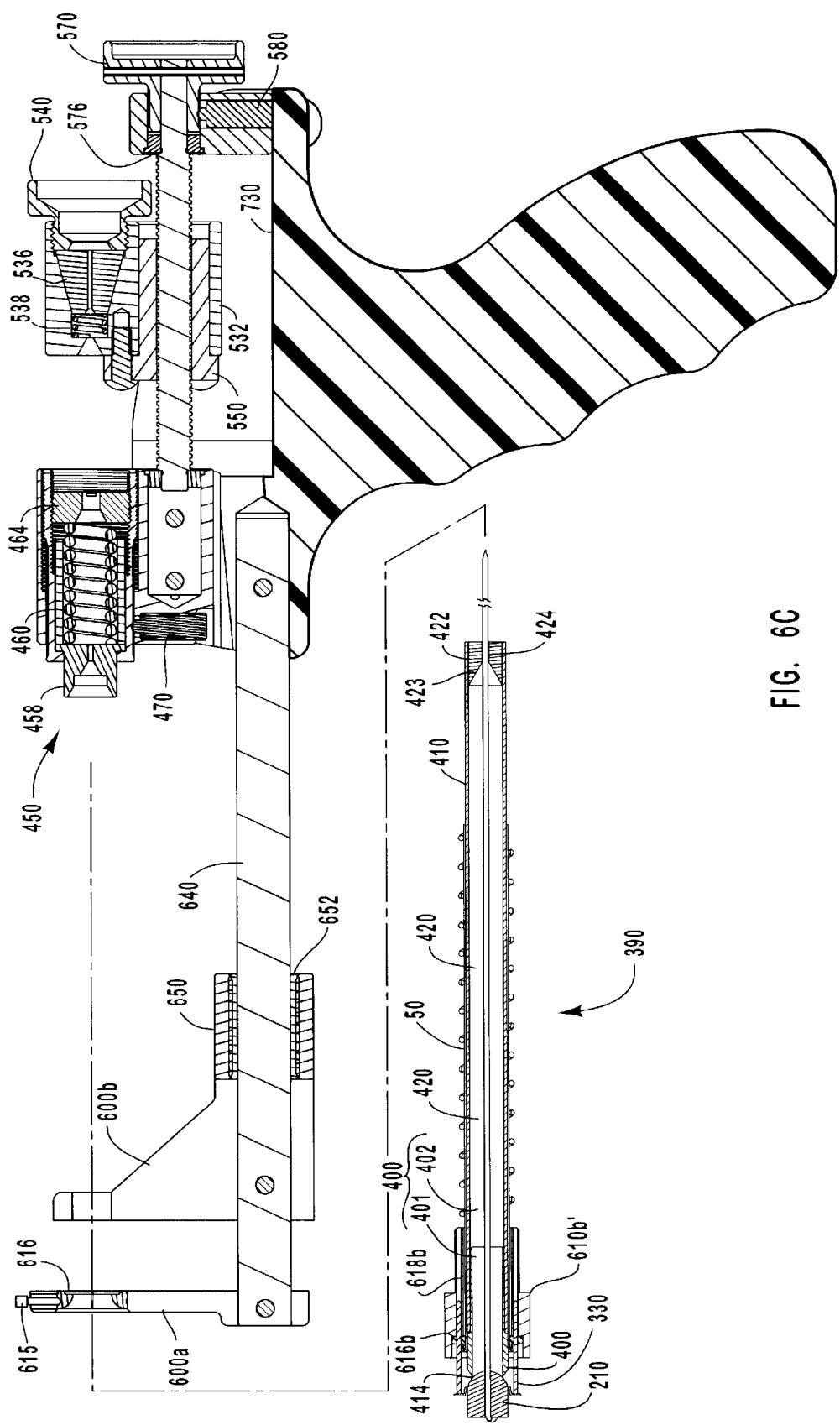
FIG. 6C is a cross-sectional view of the external anastomosis operator.

As shown in FIG. 6C, the assembly depicted in FIG. 5B is inserted such that the first compression plate 310a is held via adaptor 610a and the second compression plate 310b is held via adaptor 610b while distal end 418 of cutter 400 abuts spring biasing device 450. Anvil pull 230 is shown in FIG. 6C extending through cutter 400. Cutter 400 is hollow so it has a chamber 420 between the sidewalls of cutting tube 410. Cutter 400 may also have an optional centering core 422 that extends at least part way though chamber 420. Centering core 422 has a centering conduit 424 that assists in centering anvil pull 230 in cutter 400 such that anvil pull 230 is essentially parallel with the sidewalls of cutting tube. As discussed below in greater detail, it is not always necessary for cutter 400 to have a centering core or for other cutters to have a centering core or a centering conduit. When the engaging end of the anvil is spherical and the cutter is spherical and is configured such that it permits part of the spherical engaging end of the anvil to be positioned in cutter chamber then the cutter self centers on the spherical engaging end.

Figure 6D:
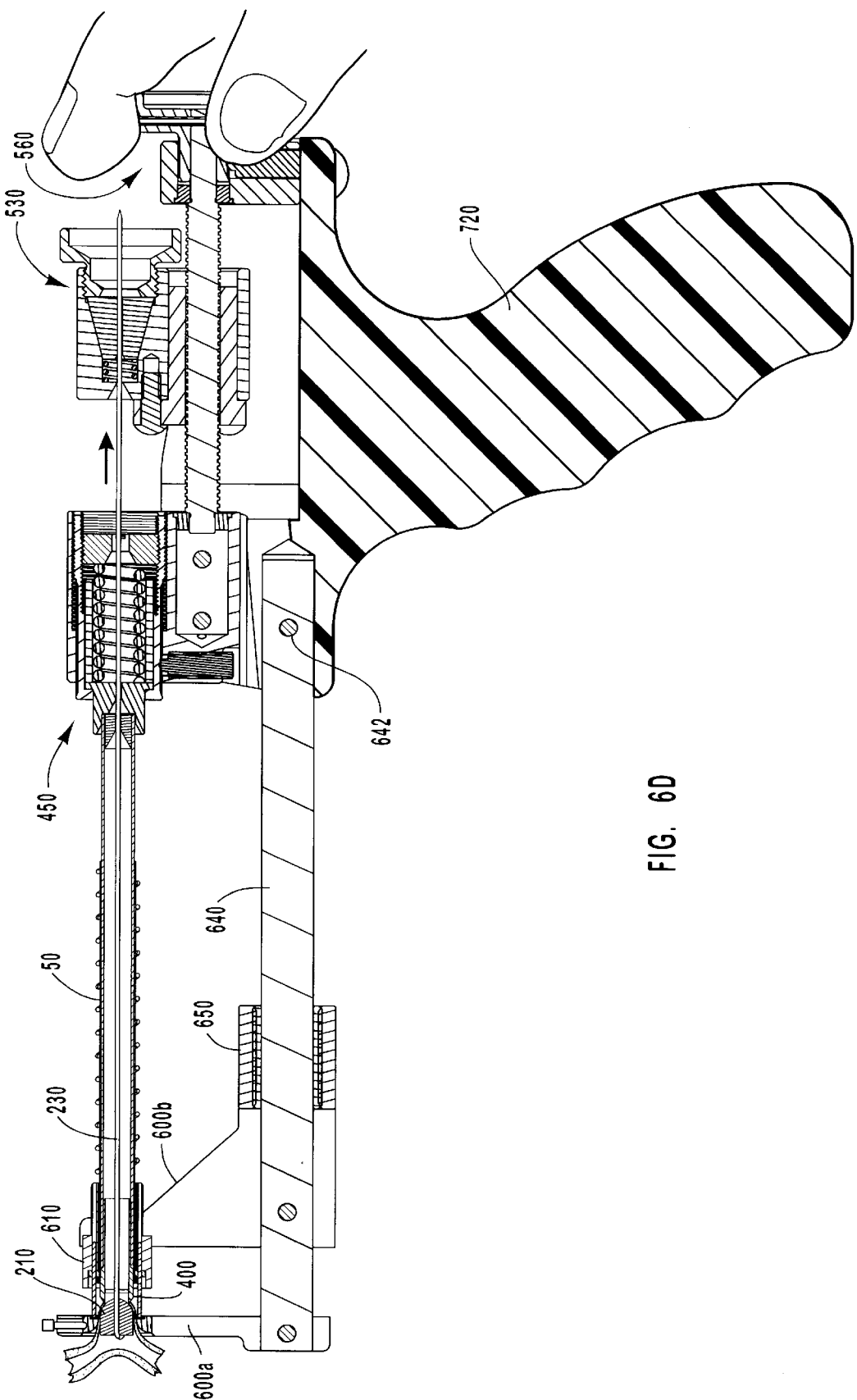
FIG. 6D is a cross-sectional view of the external anastomosis operator as the anvil pull advancer knob is rotated to pull the anvil pull so that the anvil causes distension of the blood vessel into the compression plate apparatus.

As shown in FIG. 6D, anvil pull 230 is inserted through cutter 400, through spring biasing device 450 and into an anvil pull holder 530. Holder knob 540 of anvil pull holder 530 is then rotated as described below to hold anvil pull 230. Once anvil pull holder 230 securely holds anvil pull, then advancer knob 570 is rotated as shown in FIG. 6D. Rotation of advancer knob 570 causes anvil pull holder 530 to pull on anvil pull 230, which causes anvil pull 230 to advance within compression plate assembly 300 and distend the wall of vessel 20 until cutter 400 is engaged as depicted. Note that FIG. 4B depicts anvil 210 engaging cutter 400 at the same point in the process as is shown in FIG. 6D except FIG. 4B does not show any of the components of external anastomosis operator being used.

Figure 6E:
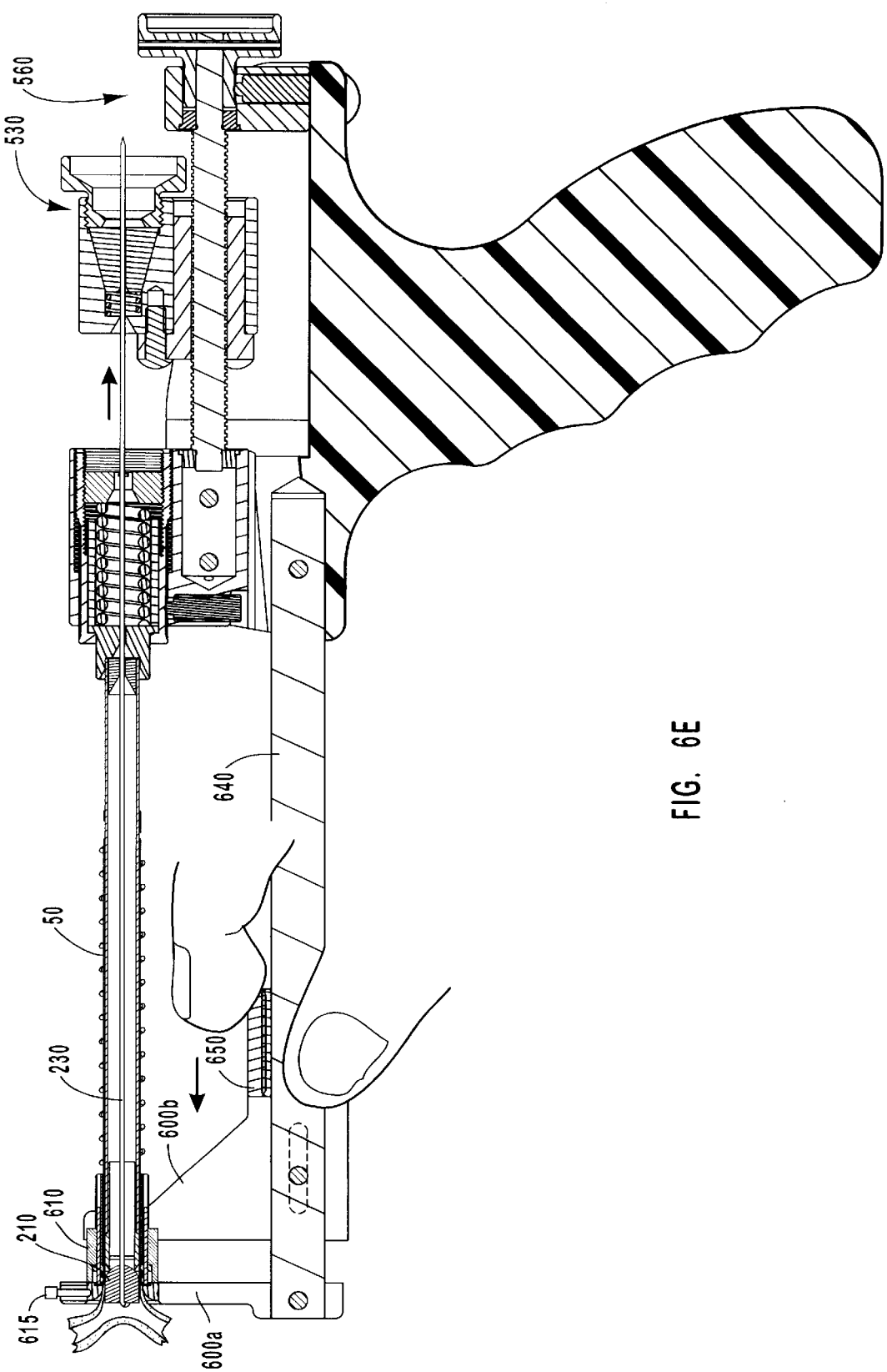
FIG. 6E is a cross-sectional view of the external anastomosis operator as the attachment actuator device is moved to compress the second compression plate against the first compression plate.

FIG. 6E depicts attachment actuation device 600 being engaged. As explained above in reference to FIGS. 4A–4D, once the anastomosis fenestra or vessel opening 24 has been made then compression plate assembly 300 can be compressed such that first and second compression plates 310a–b are brought together. As indicated above, compression plates 310a–b are preferably approximated through the use of appropriate devices. Attachment actuation device 600 achieves this purpose. Attachment actuation device 600 is also described in detail below in the External Anastomosis Operator section in reference to FIGS. 6A–6E. However, to appreciate the advantages of the preferred methodology it should be understood that attachment actuation device 600 is used to bring the compression plates together in the manner depicted in FIGS. 4A–4D. Attachment actuation device 600 has a first plate engager 600a and a second plate engager 600b. These plate holders 600a–b may directly hold first and second compression plates 310a–b or optional adapters 610a–b may be utilized. FIGS. 12C–12F depict another embodiment of an attachment actuation device 600' configured to hold compression plates without adapters. Note that compression plate apparatus 300' depicted in FIGS. 12C–12F is another embodiment of a compression plate apparatus with plates that snap-fit together. First plate engager 600a is fixedly mounted on a rail 640 while second plate engager 600b is movably mounted on rail 640. Second plate engager 600b is preferably glidably mounted on rail 640 with a fixed orientation such that it can be advanced toward first plate engager 600a to compress the compression plate apparatus 300. Second plate engager 600b is held in a fixed orientation due to the position of groove pin 644 extending through or from rail 640 which is positioned in groove 634 of first plate engager 600a. Note that as shown below in reference to FIG. 15A–15C, the attachment actuation device need not be part of the same apparatus with the anvil pull engager and the cutter.

Anvils

As discussed above in reference to anvil 210, the anvil provides a surface at its engaging end for engaging the cutter. The engaging end is also in direct contact with the blood vessel's intima at the anastomosis site when the anvil abuts the receiving blood vessel wall. The term "anvil" is meant to encompass objects with the characteristics described herein which present at least one surface that is adapted to engage a cutter.

The anvil is preferably sized at its engaging end to have a greater cross-sectional area than a cross-sectional area defined by the perimeter of the cutting edge of the cutting device such that portions of the engaging end of the anvil extend beyond the cutting edge when the cutting device engages the anvil and forms the first vessel opening. This size differential is particularly useful for cutting when the cutting device is a mechanical cutter or knife as it permits the anastomosis fenestra or vessel opening to be formed through the action of the cutting edge 414 be pressed against engaging end 212. This is a significant improvement over conventional cutting techniques that involve the external positioning of an anvil into the lumen of a vessel that is smaller than the cutter so that the vessel is cut as the cutter passes over the anvil. Such conventional cutting techniques operate much like a typical hand held paper punch used for forming holes by pushing a cutter over an anvil. Just like paper punches such vascular punches often fail to fully make the cut and leave a portion attached. The connective tissue in blood vessels in combination with the moist condition of the blood vessels further limit the effectiveness of such prior art cutting techniques. More particularly, cutting a moist highly interconnected material by squeezing it between the anvil and the cutter often results in part of the tissue merely slipping between the anvil and the cutter such that a portion is still attached.

In addition to cutters that are essentially tubular knives, additional cutting devices are described below in the section entitled Cutting Devices. These cutting devices include devices that utilize a radiation source, such as a surgical laser, that emit radiation of the appropriate characteristics to open the anastomosis fenestra in the receiving blood vessel wall. Such cutting devices that utilize radiation to ablate the vessel wall are also preferably used with an anvil having a cross-sectional area at its engaging end that is larger than the cross-sectional area defined by the perimeter of the cutting edge of the cutting device. While it is useful to have an anvil with an engaging end that extends beyond the cutting edge or the perimeter of the portion that cuts through the use of radiation to localize the impact of the cut, such as minimization of heat transfer, the engaging end need not necessarily be larger for use with such cutting devices.

Anvil 40 is preferably made of a puncture resistant material that can withstand the abrasive action of a cutting element. For example, anvil 210 may be formed from a hard plastic material such as Delrin® acetal resins or a high density polyurethane or from a metal such as stainless steel in order to withstand the abrasive action of a cutting device or of a sharp pointed end. When cutting the anastomosis fenestra with radiant energy, the anvil of this invention is preferably coated with radiation absorbing material that prevents radiation scattering. Such coated anvil embodiments are hereinafter referred to as "laser shielded anvils".

FIGS. 7A–7D provides examples for several embodiments of the anvil of this invention. A line 248 is a visual aid drawn through anvils 210a–d to clearly indicate that the portion of the anvil extending from line 248 to the anvil pull is the engaging end 212a–d. Engaging ends 210a–c are all spherical engaging ends like spherical engaging end 212 of anvil 210. Note that these spherical engaging ends are essentially a hemisphere at the side of the anvil proximal to the anvil pull 230. When the cutting device is cylindrical and is configured such that it permits part of the spherical engaging end of the anvil to be positioned in the chamber 420 then the cutter self centers on a spherical engaging end.

Landing 214 of anvil 210 is also useful feature when the anvil is used in combination with a compression plate apparatus or some of the means for joining a portion of the first vessel that defines the first vessel opening to a portion of a second vessel that defines a second vessel opening such that the first vessel and the second vessel are anastomosed together and are in fluid communication. As noted above, landing 214 is essentially the surface of the cylindrical portion of anvil 210. When an anvil with a spherical engaging end and cylindrical landings such as anvil 210 is used with a compression plate apparatus such as apparatus 300 then the spherical engaging can extend through first compression plate opening 320a and into the apparatus while landing 214 abuts the wall of blood vessel 20 against holding tabs 314a The tolerance between landing 214 and holding tabs 314a is such that landing 214 initially rests against holding tabs 314a until sufficient force is applied to pull anvil 210 through compression plate apparatus 300. As shown in FIGS. 4B–4C and FIGS. 12D–12E, landing 214 assists in the eversion process before anvil 210 is pulled through the compression plate apparatus. More particularly, landing 214 enables the portion 26 defining the first vessel opening 24 to be everted as everted portion 56 of graft vessel 50 is pushed against portion 26. As everted portion 56 pushes against portion 26, portion 26 curls up and over holding tabs 314a. This process preferably fully everts portion 26, however, satisfactory results are obtained even if portion 26 is only partially everted.

Figure 7A:
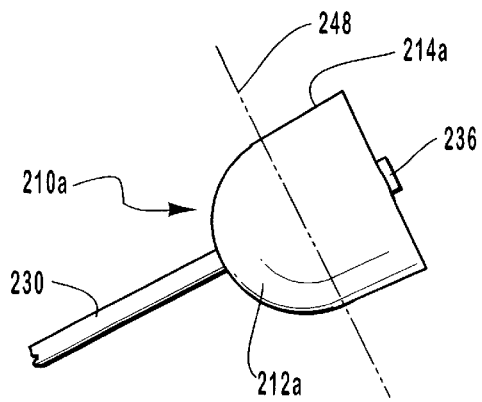
FIG. 7A is a perspective view of an alternative embodiment of an anvil having a slightly tapered landing.
Figure 7B:
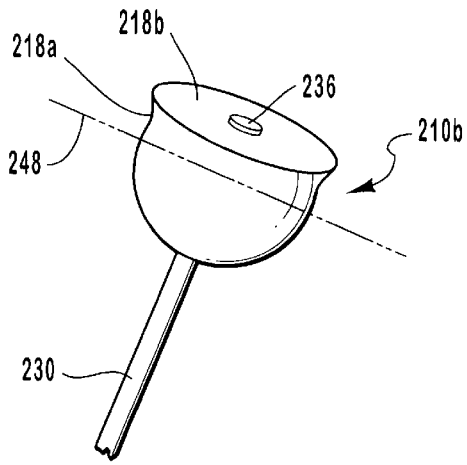
FIG. 7B is a perspective view of an alternative embodiment of an anvil having a flared flange.

FIG. 7A depicts an anvil 210a that has a landing 214a which is slightly flared so that it tapers toward the engaging end 212a. This may further assist in achieving a desired eversion. FIG. 7B shows an anvil 210b having a rounded flange at its terminal end 218 which may also assist in everting the portion of the vessel that defines the vessel opening.

Figure 7C:
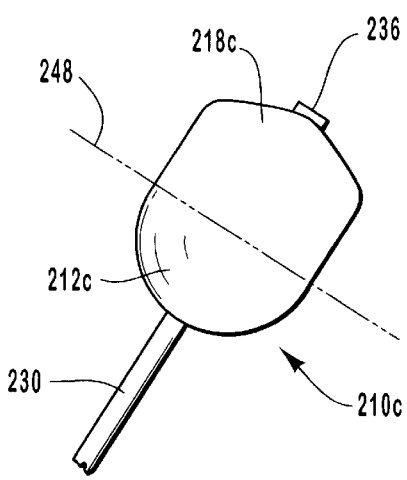
FIG. 7C is a perspective view of an alternative embodiment of an anvil having a tapered terminal end.

FIG. 7C depicts an anvil 210c that has a spherical engaging end 48 opposite from a tapered terminal end As explained below, many features described herein in reference to an intraluminally positioned anvil apparatus also relate to an externally directed anvil apparatus. As shown in FIGS. 16A–16E, FIGS. 17A–17C, FIGS. 18A–18B, FIGS. 19A–19B, an anvil 210 may be inserted though a wall of a blood vessel at an insertion opening that has been selected as an anastomosis site and positioned in a lumen of the first vessel with the anvil pull 230 extending through the insertion opening of the blood vessel. Note that such use may require some modifications. For example, use of an anvil with a tapered end such as tapered end 218c minimizes the size needed for the insertion opening since the vessel wall can stretch as the taper of the anvil increases.

Figure 7D:
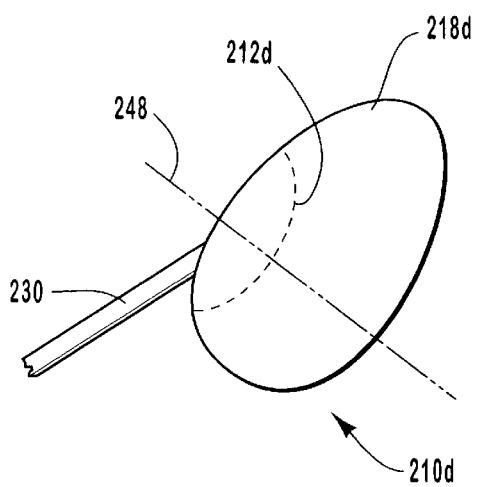
FIG. 7D is a perspective view of an alternative embodiment of an anvil having an elliptical engaging end and an eccentrically connected anvil pull.

FIG. 7D depicts an anvil 210d having an elliptical engaging ends that is adapted to receive a cutter with a corresponding elliptical configuration for the formation of elliptical openings in vessels. As described in greater detail in reference to FIGS. 14A–14C and FIGS. 16A–16B, it is often necessary to attach vessels in a nonperpendicular configuration such that it is Y-shaped instead of T-shaped. Like anvil 210c, anvil 210d has a tapered terminal end for ease in use as an externally positioned anvil apparatus. While reference is made to spherical engaging ends it should be noted that noncircular engaging ends that are convex such as the elliptical engaging end of anvil 210d may also be utilized to achieve the desired eversion, particularly when the anvil has an appropriately configured landing.

Figure 8:
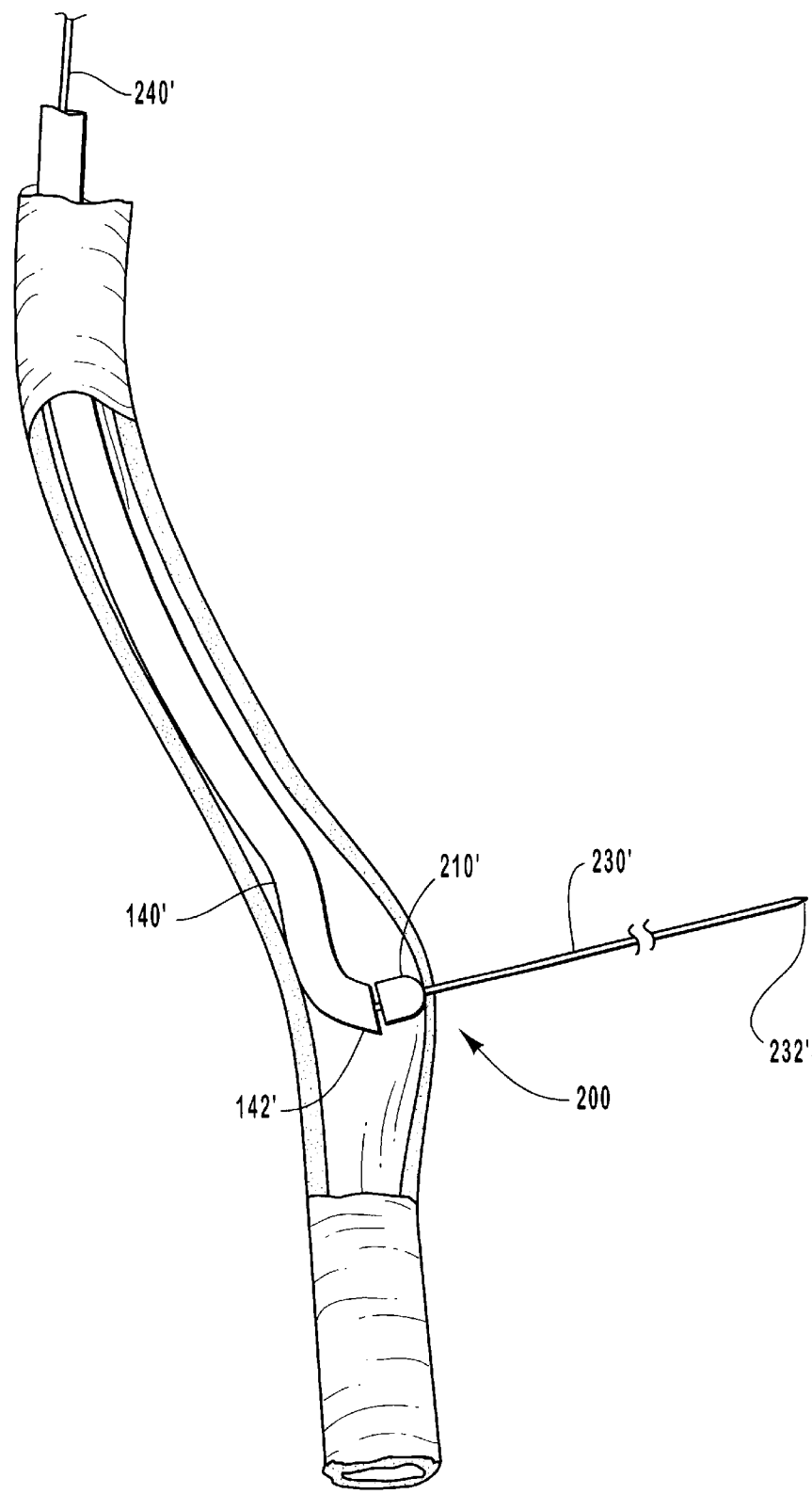
FIG. 8 is an enlarged partial cross-sectional view of the vessel shown in FIG. 2A–2F depicting an anvil pull of an intraluminally directed anvil apparatus pulled through the wall of the vessel 20 so that the anvil is brought into contact with the interior of the vessel after the apparatus has been positioned by a positioning stem extending from the anvil.

FIG. 8 depicts another embodiment of an anvil apparatus 200'. Anvil apparatus 200' has a positioning stem 240' used to push anvil 210 to the anastomosis site through a positioning catheter 140'. Accordingly, when using anvil apparatus 200' it is not necessary to utilize a piercing catheter or a piercing wire. Note also that anvil apparatus 200 has an anvil pull with a sharp piercing end 232' instead of a blunt or rounded penetration end 232 like anvil apparatus 200. The pointed configuration of piercing end 232' enables it to make initial piercing 15 in the wall of vessel 20 by puncturing the wall from its intima outward without causing undue tearing around the puncture. Piercing end 232' is then pulled from the outside of receiving blood vessel 20 just like penetration end 232 of anvil pull 230. Note that anvil pull 230 of anvil apparatus 200 may have either a distal end that is rounded or blunt like penetration end 232 or sharp such as piercing end 232'.

Anvil apparatus 200' is not shown with a stopping element such as stopping element 236 of anvil apparatus 200. Anvil apparatus 1000 in FIG. 17A also is not shown with a stopping element as its anvil pull and anvil are integral. However, anvil apparatus 200 may utilize a stopping element such as the stopping elements discussed in detail in the above section entitled Methodology Overview. For embodiments with an anvil that is nonintegral with the anvil pull, the stopping element holds anvil stationary relative to the anvil pull such while withstanding a pressure exerted at the engaging end of the anvil due to the resistance exerted by the receiving blood vessel wall being distended by the anvil and the pressure of the cutting device against the engaging end.

Anvil apparatus 200' is positioned through positioning catheter 140' by first introducing anvil pull 230' and then pushing positioning stem. When the anastomosis site is reached, then anvil pull 230' is pushed out of positioning catheter 140' and through initial piercing 15 until the engaging end 212' of anvil 210' abuts the interior of the wall of vessel 20. Catheter 140' may be positioned within lumen 28 of blood vessel in the same manner as catheter 140.

Distal end 142' may be adapted for providing a lateral exit for piercing end 232 of anvil pull 230. Distal end 142' may have a deflecting surface and a lateral aperture that guides piercing end 232 towards the intima of receiving blood vessel 20. Because piercing end 232 is very sharp, such deflecting surface is preferably a puncture and abrasion resistant surface. In addition, distal end 142' may have an appropriate marker for imaging the orientation of the aperture at distal end 142 and/or the position of distal end 142 itself Such radio-opaque markers can be any of the radio-opaque markers known in the practice of angiography. Similarly, all of the catheters used in the anastomosis procedure may have radio-opaque portions. Anvil pull 230' is typically radio-opaque itself, although very thin embodiments of this wire are preferably coated with a material such as gold or a bio-compatible barium-containing substance to make them more visible. Catheter distal end configurations for directing outwardly an elongated member have been disclosed in U.S. Pat. Nos. 4,578,061, 4,861,336, 5,167,645, 5,342,394, and 5,800,450, which are hereby incorporated by reference in their entirety.

The dimensions of any of the embodiments of the anvil of this invention are determined by the size of the lumen of the receiving vessel and by the dimension of the passage that will ensure the fluid communication between the graft vessel and the receiving vessel after they have been anastomosed. These dimensions are typically chosen or known in the art. For example, when a graft vessel of about 4 mm in diameter is to be anastomosed to a receiving blood vessel which has an approximate lumen diameter of about 8 mm, the diameter of anvil at its widest may range from about 3 mm to about 6 mm. So for anvil 210, the diameter at landing 214 may range from about 3 mm to about 6 mm for use in such a vessel. However, the anvil may have any suitable size that enables it to be positioned as needed. Note that the anvil is preferably designed so that the blood flow through the receiving blood vessel will preferably not be interrupted during the anastomosis. However, the design can be such that the blood flow is interrupted when this feature is desired.

FIGS. 9A–9B, FIGS. 10A–B and FIGS. 11A–B each depict an anvil apparatus with an anvil that is deployable after reaching the anastomosis site such that they have an expanded size when needed. FIGS. 9A–9B and FIGS. 10A–B depict mechanically deployable anvils while FIGS. 10A–10B depict a chemically deployable anvil.

The anvil apparatus depicted in FIGS. 9A–9B is identical to that of anvil apparatus 200 except anvil 210 is smaller and two flexible anvil sheaths 260a–b are positioned on anvil pull 230. Flexible anvil sheaths 260a–b are adapted to be nested as shown in FIG. 9B once the wall of vessel 20 is encountered to cause the flexible anvil sheaths 260a–b to be dislodged from their positions on anvil pull 230. Anvil sheaths 260a–b may be retained in their spaced positions on anvil pull through reliance on a tight frictional fit or stops may be utilized to ensure that the sheaths are not dislodged until desired at the anastomosis site through application of an appropriate amount of force. When nested on anvil 210, flexible sheaths 260a–b and anvil 230 act together as an anvil. The anvil sheaths may be relatively soft compared to anvil 230 so it may be necessary to treated the anvil sheaths with a puncture resistant material or an abrasion resistant material.

FIGS. 10A–10B depict a flexible anvil 210" that is narrow when collapsed and becomes wider when its engaging end 212" encounters the wall of blood vessel 20. The engaging end 212" of anvil 210" is not attached to anvil pull 230, only terminal end 218" is attached to anvil pull. Since anvil 210" is hollow, it can flex into an expanded or deployed position when engaging end 212" is pushed toward terminal end 218".

Figure 11A:
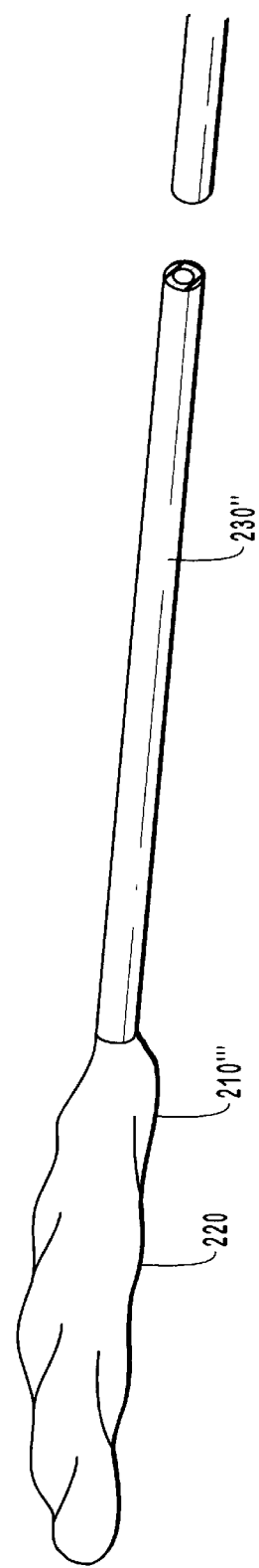
FIG. 11A is a perspective view of a chemically expandable anvil.
Figure 11B:
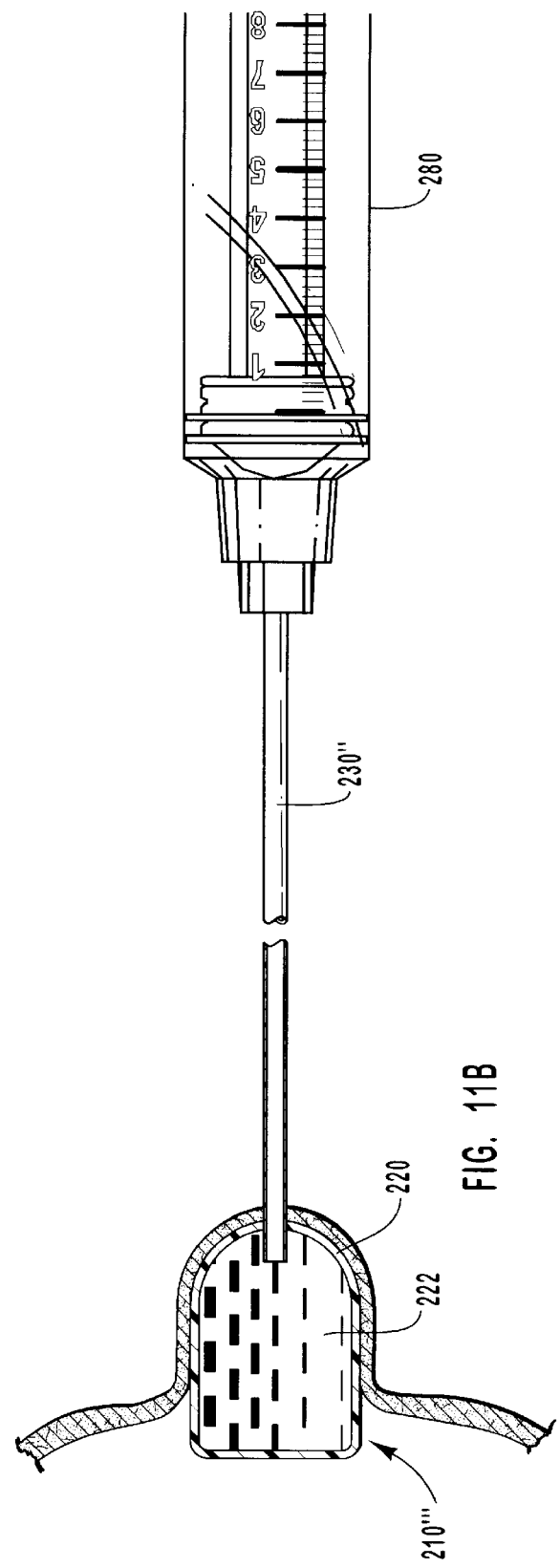
FIG. 11B is a cross-sectional view of the anvil shown in FIG. 11A.

FIG. 11A depicts a balloon anvil 210'" in a deflated condition extending from a hollow tubular anvil pull 230". FIG. 11B depicts balloon anvil 210'" deployed in an inflated condition ready for engagement against the interior of a vessel at an anastomosis site. Balloon anvil is preferably chemically deployed by being filled with a polymerizable material that hardens in situ. For example, syringe 280 may be coupled to tubular anvil pull 230 to enable a composition to be delivered that includes conventional monomers that rapidly polymerizes in the presence of appropriate chemical initiators.

For example, the monomers may be suitable acrylates such as urethane dimethacrylate, phydroxyphenyl methacrylamide, butane diol dimethacrylate, and bisphenol-A-diglycidyl dimethacrylate ("Bis-GMA"). Examples of appropriate chemical initiators include a wide range of peroxides, other per components, and other free radical generators. An appropriate two-part chemical curing system typically includes a peroxide constituent in one part and an amino compound in another. Exemplary peroxides include benzoyl peroxide, 2-butanone peroxide, lauroyl peroxide and tert-butyl peroxide. Examples of amino compounds include dimethylamino ethyl methacrylate, triethyl amine, 2-dimethylamino ethanol, diethylamino ethyl methacrylate, trihexyl amine, N,N-dimethyl-p-toluidine, N-methylethanolamine, and 2,2'(p-tolyinino) diethanol.

After the polymerizable material, the mixture of monomers and chemical initiators, has been delivered into balloon anvil 210'" then it is necessary to wait for the material to polymerize such that anvil 210'" is hard. As shown in FIG. 11B, once the polymerizable material has hardened then anvil pull 230" is anchored in polymerized material 222 and polymerized material 222 is surrounded by balloon 220. Since anvil pull 230" is anchored in polymerizable material 222, balloon anvil 210 can be used in a cutting process without regard to the softness of balloon 220. More particularly, if a cutter 400 presses through balloon 220 then it merely rests on the exposed polymerized material 222 with the cut portion of blood vessel 20 and is removed along with the entire anvil apparatus 200'".

Balloon anvil may also be merely inflated with gas or an appropriate fluid, however, such a balloon anvil is best utilized with embodiments that do not require the anvil to be puncture resistant such as a cutting device that uses radiation followed by steps such as gluing, welding or soldering to join the vessels together. Of course, it may be necessary to treat the engaging end of a balloon anvil such that it is laser shielded by placing a laser shield material at the engaging end of the balloon anvil. One example of a laser shield material is a shield consisting of a sandwich of polymethylmethacrylate and tinfoil that is known to provide corneal and retinal protection from inadvertent injury during argon, Nd-YAG or dye laser treatment at the tested laser power outputs. Similarly, the balloon anvil may be treated with an appropriate material such that it is puncture resistant or distortion resistant.

The balloon may also be a puncture resistant balloon. Puncture and scratch resistant balloons have been disclosed in U.S. Pat. Nos. *5,766,158, 5,662,580, 5,620,649, 5,616, 114, 5,613,979, 5,478,320, 5,290,306,* and *5,779,731,* which are hereby incorporated by reference in their entirety. In still another embodiment of this invention, the anvil of this invention can be embodied by the combination of a balloon and a puncture resistant balloon sheath. A balloon plus balloon sheath combination has been disclosed in U.S. Pat. No. 5,843,027 which is hereby incorporated by reference in its entirety.

In summary, the anvils are configured in a way such that it effectively cooperates with the cutting device to form the opening of the anastomosis fenestra. The anvils also cooperates in the eversion of the edge of the anastomosed fenestra. Furthermore, the anvil of the present invention is configured so that it can abut the receiving blood vessel wall at the anastomosis site from the intraluminal space of such blood vessel. In addition, the anvil of this invention is configured so that it effectively cooperates with the compression plate apparatus in the joining of the anastomosed structures. The anvils disclosed herein are all examples of anvil means for engaging the interior surface of a first vessel at an anastomosis site. The anvil means that are part of an intraluminally directed anvil apparatus are more specifically anvil means for engaging the interior surface of the wall of a first vessel at an anastomosis site wherein the anvil means is sized to pass within the lumen of the first vessel from an insertion site to a remotely located anastomosis site.

Compression Plate Apparatus

As indicated above, the plates are configured so that they provide support to the everted openings of the anastomosed structures and facilitate the eversion of the receiving blood vessel, the vessel to which another vessel is being attached that has been everted before initiating the procedure. The compression plate apparatus also eliminate the need for skilled suturing. Use of the compression plate apparatus makes anastomosis procedures more efficient in a reliable manner. Additionally, the compression plate apparatus holds the anastomosed structures in an effective leak proof contact engagement.

In each compression plate, the side which is in contact with the everted contour of the anastomosed structure is described as the anastomosis side. In the practice of an anastomosis according to this invention, compression plates are used in a way such that the anastomosis sides of the two compression plates are opposite to each other. Preferred embodiments of compression plates have a generally annular shape with interior openings which have a generally circumferential contour; the internal diameter of each one of these openings is such that the corresponding portion of the vessel to be anastomosed can fit therein. Typically, this internal diameter is approximately equal to, or slightly greater than, the external diameters of the corresponding portion of the vessel to be anastomosed. An internal diameter slightly greater than the external diameter of the corresponding portion of the vessel to be anastomosed is preferred. With this internal diameter, the compression plate does not pose a significant obstacle to the periodic dilation that the vessel is subject to as a consequence of the characteristics of the fluid flow that circulates through the anastomosed structures.

There are two primary embodiments disclosed herein including the guided compression plate apparatus 300 shown in FIGS. 3A–3B, FIGS. 4A–4E, FIGS. 5A–5B, FIGS. 6C–6E and the snap-fit compression plate apparatus 300' shown in FIGS. 12A–12G. A variation of compression plate apparatus 300 is also shown at 300" in FIG. 13 to show that a compression plate apparatus can also be used for joining vessel together in a nonperpendicular orientation. Each plate has an opening 320*a–b* that is generally round, however, as shown in FIG. 13, the openings may also be ellipsoidal, ovoid, or have other noncircular configurations. The compression plate apparatus can be used in combination with either an intraluminally directed anvil apparatus or an externally positioned anvil apparatus.

Compression plate apparatus 300 is best viewed in FIGS. 3A–3B. Compression plate apparatus 300 has a compression plate 310*a* is referred to as a first compression plate or a receiving vessel compression plate while compression plate 310*b* is referred to as a second compression plate or an attaching vessel compression plate. As discussed above, compression plate apparatus 300 is shown in FIG. 3A before graft vessel 50 has been loaded onto holding tabs 314*b* of second compression plate 310*b* while. FIG. 3B shows graft vessel 50.

Compression plates 310*a–b* are provided in the exemplary embodiment shown in FIG. 3A with a plurality of holding tabs 314*a–b* respectively protruding from opposing anastomosis sides 322*a* (not shown) and 322*b* of compression plates 310*a–b*. More particularly, holding tabs 314*a–b* extend respectively from rings 312*a–b* of compression plates 310*a–b*. Holding tabs 314*a–b* are intended to hold the everted contours of the structures being anastomosed. Each one of holding tabs 314*a–b* has a base that integrally extends from the anastomosis side of the ring 312*a–b* of the corresponding plate at 313*a–b* and that terminate at rounded tips 316*a–b*. Distal tips 316*a–b* are preferably rounded as shown to minimize the potential for penetration. However, in some embodiments, the distal tips may be pointed, for example, when holding a graft vessel. Holding tabs 314*a–b* are typically rather rigid, however, they may also be designed to elastically bend in such a way that the distal tips of such holding tabs slightly swing about their respective bases. Such a bending action may be caused by the displacement through any of openings 320*a–b* defined by holding tabs 314*a–b*, more particularly the distal tips 316*a–b* of holding tabs 314*a–b*.

The number of holding tabs and their spacing may be varied as need as long as the portions of the vessels defining the vessel openings can be maintained in an everted orientation. For example, the plurality of holding tabs may include sixteen holding tabs as shown in FIG. 3A. However, smaller amounts may also be utilized, for example there may be only six to ten holding tabs.

Holding tabs such as holding tabs 314*a–b* can have a plurality of shapes. The holding tabs preferably used in embodiments of this invention are wider at the base and so configured as to extend into a distal rounded tip at the end opposite to the base. Although holding tabs 314*a–b* can be distributed in a variety of arrays, a generally regular distribution on the anastomosis sides of the compression plates is preferred.

Each of the holding tabs shown in the embodiment schematically depicted in FIG. is attached at its base 316*a–b* at the inner peripheries 313*a–b* of rings 312*a–b*. However, the bases 316*a–b* may also extend from other locations of the rings. For example, the bases 316*a–b* may extend from rings 312*a–b* between the outer peripheries 31 l*a–b* and the inner peripheries 313*a–b* or perimeter on the anastomosis sides 322*a–b* of each annular compression plate.

Although, it is not necessary for the holding tabs in each compression plate to be oriented relative to the holding tabs in the other compression plate in a mating configuration, it is preferred. When referring to the relative configuration of the holding tabs in opposing compression plates, the terms "mating or mated configuration" describe a configuration in which each one of the holding tabs in a compression plate can generally fit in the space between two neighboring holding tabs in the opposing compression plate when such compression plates are close enough. As shown by the phantom lines in FIG. 3A, holding tabs 314*b* are offset from holding tabs 314*a* such that as the plates are brought towards each other each holding tab 314*b* is positioned opposite from the spaces between holding tabs 314*a* in a mated configuration. When the compression plates are brought together just close enough for the tips 316*a–b* to be in the same plane, then the everted tissue is held in place and the anastomosis is secure. Failure to bring the compression plates sufficiently close together such that the tips 316*a–b* are significantly close together risks the potential loss of the tissue that has been captured and everted onto holding tabs 314*a–b*. Note that each holding tab 314*b* is shown just barely entering into an opposing space between adjacent holding tabs 314*a*. Of course, the compression plates may be designed for further compression such that holding tabs 314*b* further enter the space between adjacent holding tabs 314a. However, the compression plates are preferably designed such that the plates are brought together without penetrating blood vessel 20 or graft vessel 50. Note that guides 330 maintain the orientation of the compression plates so that the respective teeth have the preferred mating configuration.

An example of a suitable compression is provided by a compression plate apparatus having holding tabs with lengths of 0.045 inches (0.1143 cm) that has a distance between the anastomosis sides 322a–b of rings 312a–b of 0.090 inches (0.2286 cm). Compression down to only 0.10 inches (0.254 cm) for such a compression plate apparatus is generally insufficient to hold the anastomosed tissues. The plates may be farther compressed such that the distance between the anastomosis sides 322a–b is 0.080 inches (0.2032 cm) or 0.070 inches (0.1778 cm) to bring vessel 20 and vessel 50 even closer together. However, as noted above, it is preferable to avoid pushing through the vessels. The compression plate are accordingly designed to permit compression down to the ideal spacing between the anastomosis sides while providing holding tabs that are long enough to capture the tissue in an everted configuration.

The holding tabs such as holding tabs 314a–b are preferably configured in a way such that they are not exposed to blood flowing through the anastomosed structures. Some embodiments of this invention are provided with holding tabs that are coated with a biocompatible non-thrombogenic material to prevent the formation of thrombi if such holding tabs or any portion thereof becomes exposed to blood flow. An example of such material is TEFLON.

Holding tabs of a variety of shapes which are distributed in varying numbers and arrays on the anastomosis sides of compression plates 310a–b and equivalents thereof are exemplary embodiments of means for holding a portion of a vessel that defines the vessel opening. As indicated above, the holding tabs preferably hold the portion of the vessel that defines the vessel opening in a manner such that the portion defining the first vessel opening is at least partially everted and is not penetrated. The holding tabs disclosed herein are all examples of holding means for holding a portion of a first vessel that defines a vessel opening in manner such that the portion defining the vessel opening is at least partially everted and is preferably not penetrated.

As indicated above, guides 330 permit the relative approach of these two plates as compression plate 310b slides along guides 330 towards compression plate 310a. More particularly, guides 330 enable compression plates 310a–b to be brought together in a manner such that second compression plate 310b is moved in a fixed parallel orientation relative to first compression plate 310a. Additionally, guides 330 are positioned relative to holding tabs 314a–b and have a length that permits graft vessel 50 to be loaded onto holding tabs 314b and then be brought into contact with blood vessel 20. Stated otherwise, the configuration of guides 330 enables first vessel opening 24 and second vessel opening 54 to be initially spaced apart and opposite from each other and then to be advanced toward each other as second compression plate 310b is moved with graft vessel 50 held on the holding tabs 314b while blood vessel 20 is held by holding tabs 314a of compression plate 310a. As best shown in FIGS. 4A–4D, movement of second compression plate 310b toward first compression plate 310a brings the portion 56 of graft vessel 50 that defines the second vessel opening 54 into contact with the portion 26 of blood vessel 20 that defines the first vessel opening 24 such that the blood vessel and the graft vessel are anastomosed together.

Compression plate 310b is slidably mounted on guides 330 at guide apertures 334. To slide compression plate 310b along guides 330, each one of ends 332 of guides 330 is introduced through one of guide apertures 334 of compression plate 310b. Ends of guides 330 opposite to ends 332 are attached to ring 312a of compression plate 31a, however, guides 330 may also integrally extend from ring 312a.

As shown, the compression plate apparatus preferably has a plurality of guides. While compression plate anastomosis 300 is shown with four guides 330, other embodiments may have other configurations such that the plurality of guides includes, for example, three to six guides. Further, other embodiments may have less than three or more than six guides. It is even possible to have only one guide. Although guides 330 can be distributed in a variety of arrays, a generally regular distribution is preferred in embodiments with more than one guide.

When compression plates 310a–b are in close proximity to each other at an anastomosis site providing support to the anastomosed structures, terminal ends 332 of guides 330 can extend away from compression plates 310a–b to an extent such that the protrusion results in the presence of an undesirable feature in the immediate neighborhood of the anastomosis site. To solve this problem, embodiments of the compression plate devices of this invention are provided with guides 330 which can be appropriately shortened by removing an appropriate length of terminal ends 332. In some embodiments, terminal ends 332 are manufactured with a material which dissolves after an appropriate time following the anastomosis. In other embodiments, guides 330 are made of a material that can easily be clipped to a desired length, thus eliminating terminal ends 332 as shown in FIG. 4D. In other embodiments, guides 330 can be provided with notches or some other localized weakened structural feature which facilitates the easy removal of terminal ends 332 at desired distances with respect to plate 310a. Still other embodiments can be provided with terminal ends 332 that can easily bend to an extent such that undesirable protrusions are eliminated.

The guides may have a variety of lengths and be distributed in varying numbers and arrays. The guides may also extend from one or both of the compression plates at any appropriate location. However, the guides are preferably situated such that the portion 26 defining the blood vessel opening 24 and the portion 56 defining the graft vessel opening 54 are joined without being penetrated as the first vessel and the second vessel are anastomosed together. The guides disclosed herein are exemplary embodiments of means for guiding the movement of one compression plate with respect to the other compression plate. More particularly, the guides disclosed herein are examples of means for guiding the movement of one compression plate relative to the other such that one compression plate moves in a fixed parallel orientation relative to the other compression plate.

Guide apertures 334 are sized to frictionally engage guides 330 in a manner such that compression plate 310b does not inadvertently slide on guides 330, particularly not after being compressed towards compression plate 310a. In the absence of a suitable frictional engagement, compression plate 310b may slide away from compression plate 310a to potentially jeopardize the leak-proof character of structures held together by the compression plates. An undesired separation could be caused, for example, by an expansion of the anastomosed structures at the anastomosis site, caused in turn by the pressure exerted by the fluid circulating therethrough.

When second compression plate is formed from plastic, the desired frictional engagement is generally achieved whether guides 330 are made from metal or plastic. However, when second compression plate is formed from metal and the guides are also metal, it is preferable to utilize an alternative frictional engagement. For example, FIG. 5A shows compression plate apparatus 300 with an optional holding ring 340 that has a friction coupling with guides 330 through its guide orifices 346. Holding ring 340 is provided with opening 348 whose internal diameter is preferably at least equal to that of the opening 220*b* of compression plate 310*b*. The frictional engagement of holding ring 340 with guides 330, like the frictional engagement described above for guide apertures 334 with guides 330, is such that expansion of the anastomosed structures can not separate compression plates 310*a–b* with respect to each other when holding ring 340 is in contact engagement with exterior side 324*b* (not shown) of compression plate 310*b* opposite to its anastomosis side 322*b*. The holding ring may, for example, be formed from nylon.

Other embodiments of this invention are provided with different frictional engagements that are designed to prevent compression plate 310*b* from significantly moving away from compression plate 310*a* For example, guides 330' of compression plate apparatus 300" in FIG. 13 have barbs 336. These frictional engagement configurations described above enable the compression plates to be approached to a desired relative separation and maintained at that separation. This feature also permits the control of the pressure applied to the everted tissue of the anastomosed structures and the compression of the plates in stages so that they are approximated in a controlled manner.

These frictional engagements are all examples of means for locking the compression plates together. More particularly, guides that engage appropriately sized apertures 334 of second compression plate 330*b* for frictional engagement, a holding ring 340 that has guide orifices 346 sized to fractionally engage a guide 330, and guide barbs 336 for irreversible advancement of second compression plate 310*b* as the guide extends through guide apertures 334 of second compression plate 310*b* are all examples of means for locking the compression plates together. Note that when the frictional engagement is achieved through reliance on guides that extend from a first compression plate and that pass though appropriately sized apertures in the second compression plate then it can be said that the first compression plate and the second compression plate have means for locking the compression plates together. An advantage of such locking means that are part of the first and second compression plates is that it is not necessary to separately attach the locking means to the compression plate apparatus after it has been used to anastomose the vessels.

The compression plate apparatus is preferably used for vascular anastomosis, however, the present invention is not limited to such use. Nor is the compression plate apparatus limited to use with any particularly sized vessel. For example, vessels may be joined with diameters ranging from about 2 mm to about 20 mm, but there is no fundamental limitation for using embodiments of this invention with graft vessels with diameters less than 2 mm.

A variety of techniques known in the art can be used to manufacture compression plates within the scope of this invention depending on the material used. Compression plate apparatus 300, 300' and 300" can be formed from a plastic material such as nylon or from metals such as titanium or nickel/titanium alloys. Stainless steel can be used but is not preferred. Additionally, one plate may be formed from a metal while the other is formed from plastic. In addition to molding the plates, when the plates are formed from metal, the plate may be cut from a disk in a flat configuration and then the holding tabs can be bent into position.

Although guides such as guides 330 provide a convenient structural element for appropriately orienting and approaching the compression plates of this invention relative to each other, the appropriate orientation and relative displacement of the compression plates can be achieved in other ways that accomplish the same effects as discussed for example in reference to compression plate apparatus 300'. These different ways of providing the appropriate relative orientation of the compression plates and the relative displacement are within the scope of this invention. For example, a device used to hold the compression plates as shown in FIG. 6D–6E, FIG. 12C–12G, and FIG. 16C can provide the appropriate support for orienting and displacing the compression plates relative to each other. Similarly, the cutting device may be configured to provide the appropriate orientation.

Figure 12A:
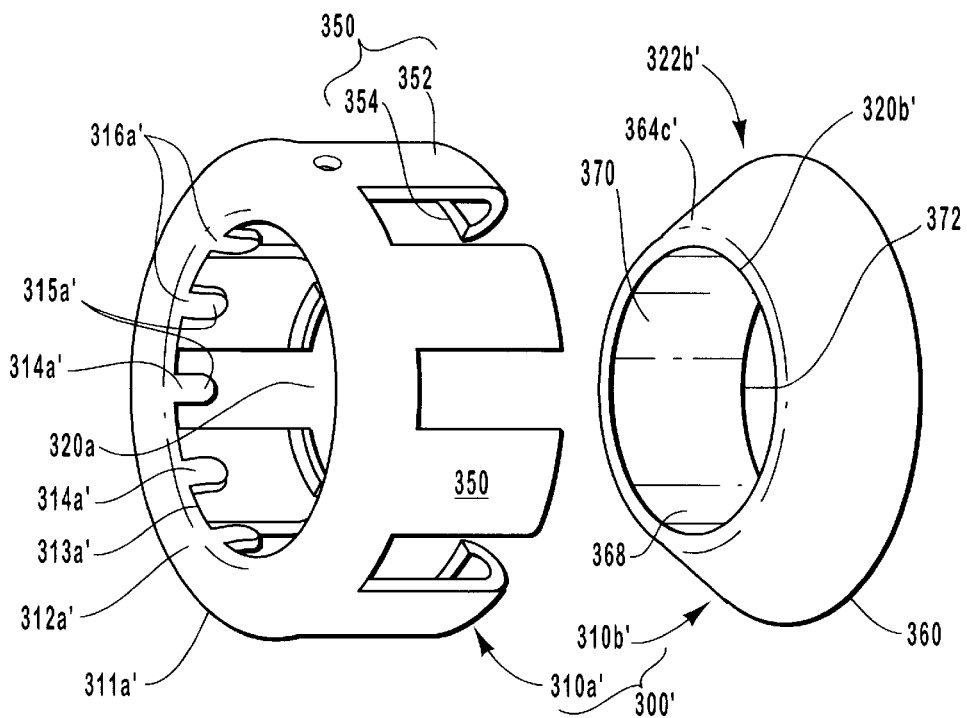
FIG. 12A is a perspective view of a snap-fit compression plate apparatus.
Figure 12B:
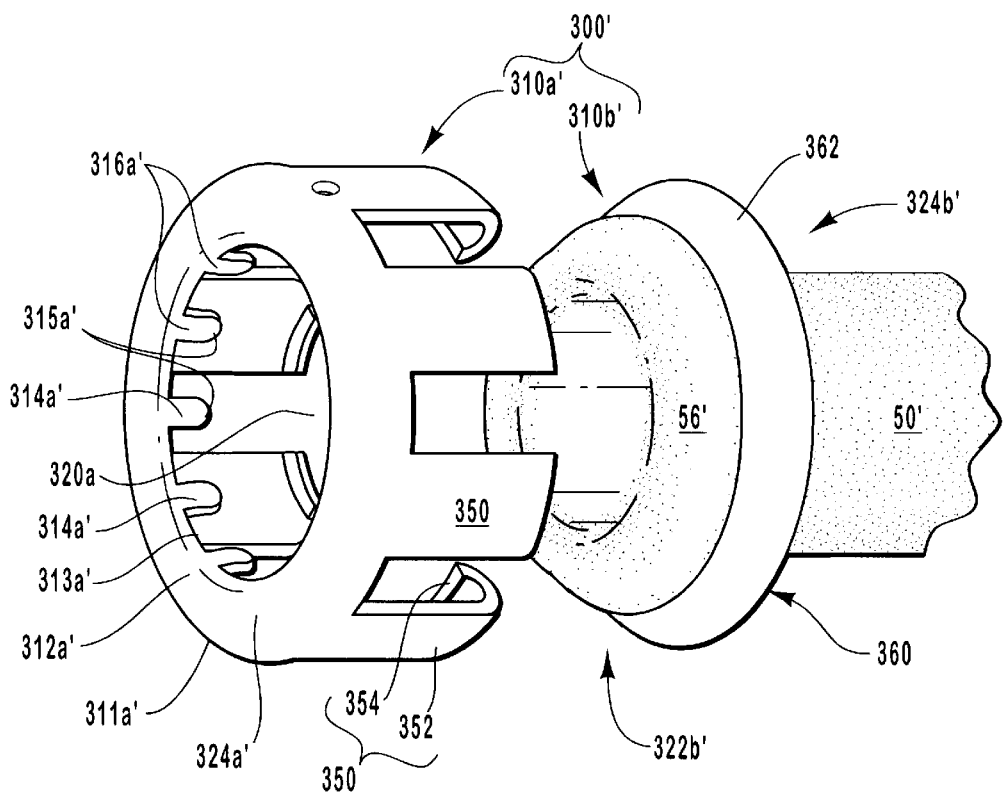
FIG. 12B is a perspective view of the snap-fit compression plate apparatus shown in FIG. 12A with a graft vessel loaded onto the holding surface of the second compression plate.

FIGS. 12A–12B provide a perspective view of snap-fit compression plate anastomosis apparatus 300'. Like guided compression plate apparatus 300, snap-fit compression plate apparatus 300' has two opposing compression plates including a first compression plate 310*a*' and a second compression plate 310*b*'.

First compression plate 310*a*' has a ring 312*a*' with an inner periphery 311' and an outer periphery 313'. A plurality of holding tabs 314*a*' extend from ring 312*a*'. Like holding tabs 314*a*, each holding tab 314*a*' has a base 316*a*' and terminate at a distal rounded tip 315*a*'. The base of each tab is preferably integral, as shown, with ring 312*a*'. Each holding tab 314*a*' extends at its base from ring 312. More particularly, each holding tab 314*a*' extends from inner periphery 311' from exterior side 324*a*' toward anastomosis side 322*a*' (not shown).

Holding tabs 314*a*' extend either perpendicularly from ring 312*a*' of first compression plate 310*a*' or curve inward from exterior side 324*a*' of ring 312*a*' of first compression plate 310*a*' such that distal rounded tips 316*a*' of holding tabs 314*a*' are perpendicularly oriented relative to exterior side 32*a*' of ring 312*a*' of first compression plate 310*a*'. Like holding tabs 314*a*, holding tabs 314*a*' may have varying configurations and various numbers of holding tabs may be utilized.

First compression plate 310*a* also has a plurality of locking arms 350 extending from outer periphery 311*a*'. Locking arms 350 are adapted to lock with a locking extension 360 projecting from second compression plate 310*b*'. Engagement of these locking components enables compression plates 310*a*'–310*b*' to lock together such that the portion 26 defining the first vessel opening 24 and the portion 56 defining the second vessel opening 54 are joined without being penetrated as the first vessel and the second vessel are anastomosed together.

Locking arms 350 have a length that enables them to lock around locking extension 360 in a manner such that the portion defining the first vessel opening and the portion defining the second vessel opening are held together without being damaged in a manner that causes the anastomosis to fail. Each locking arm 350 has a pivot portion 352 that terminates at a grasping portion 354. Grasping portion 354 is preferably a curved portion of locking arm 350 directed annularly inward.

Second compression plate 310*b*' has a second compression plate opening 320*b*', or more precisely, an anastomosis side opening 320b', defined by a holding surface 364. Second compression plate opening 320b' may also be described as being defined by rim 368 which is the point at which holding surface joins tubular portion 370. Holding surface 364 extends radially downward at an angle from anastomosis side opening 320b' and terminates at locking extension 360 such that second compression plate 310b' flares in diameter from second compression plate opening 320b' down to locking extension 360. Locking extension 360 has two surfaces, a flaring surface 362 that is continuous with holding surface 364 and a locking surface 366 shown in FIG. 12C–12G. While locking extension is shown having a flaring surface 362 that is a continuous extension of holding surface 364, these surfaces may also be distinct.

Holding surface 364 has a configuration that permits the portion of the second vessel 50' defining the second vessel opening 54' to be everted onto holding surface 364 as shown in FIG. 12B. The vessel shown in FIG. 12B everted on holding surface 364 is an autologous or heterologous blood vessel 50'. Of course, a graft vessel like vessel 50 can also be used, however, vessel 50' is identified as being autologous or heterologous in order to depict the use of vessels that are not artificial. Everted portion 56' of vessel 50' is preferably adhered onto holding surface 364 through the use of an appropriate adhesive such as those described above in the Background section or attached through the use of stay sutures or other means for holding vessel in an everted position. While holding surface is shown extending radially downward at an angle from the second compression plate opening, it may have any surface that is suitable for everting the portion of vessel 50' that defines opening 54' and for holding the everted portion 56'.

As shown in FIG. 12B, tubular portion 370 is adapted to receive vessel 50' through exterior side opening 372 such that graft vessel can pass though anastomosis side opening 320b' and be everted onto holding surface 364. As shown in FIG. 12G, exterior side opening 372 is defined by tubular portion 370 and locking surface 366. The farther that locking surface 366 extends from exterior side opening 372 the greater the distance between vessel 50' and grasping portion 354 once the anastomosis is complete. Tubular portion 370 may have an extension to provide further protection for vessel 50' against contact with grasping portion 354. Tubular portion 370 may have a slanted orientation corresponding to the angled orientation of holding surface 364. However, tubular portion is preferably configured such that it has parallel sides as such a configuration enables the barrier between grasping portion 354 of locking arms 350 and vessel 50' to be maximized.

Holding tabs 314a' are additional examples of holding means for holding a portion of a first vessel that defines a vessel opening in manner such that the portion defining the vessel opening is at least partially everted and is preferably not penetrated. Holding surface 364 is a also an example of holding means for holding a portion of a first vessel that defines a vessel opening preferably in manner such that the portion defining the vessel opening is at least partially everted and is preferably not penetrated.

FIGS. 12C–12G provide a sequential presentation of the steps involved in utilizing snap fit compression plate apparatus 300' as an anastomosis fenestra is formed in first vessel 20 and as the compression plates are brought together to approximate vessel 20 and vessel 50. The sequential steps depicted in FIGS. 12C–12G are similar to steps depicted in FIGS. 4A–4D for the use of guided compression plate apparatus 300. However, FIGS. 12C–12G also show the use of attachment actuation device 600' having a first plate engager 600a' and a second plate engager 600b'. Attachment actuation device 600' is slightly different from attachment actuation device 600, which is described in reference to FIGS. 6A–6E in detail in the section entitled External Anastomosis Operator. in that it is not necessary to utilize the optional adapters 610a–b since first and second compression plates 310a'–310b' are directly engaged Each plate engager 600a'–600b' has a component or a portion that directly contacts the plate in a configuration such that the plate is held in a locked manner or such that the plate can be moved. A plurality of screws 615a' lock first compression plate 310a' in place while extension 615b' of second plate engager 600b' pushes second compression plate 310b'. First compression plate 310a' may have recesses for receiving screws 615a'.

Figure 12C:
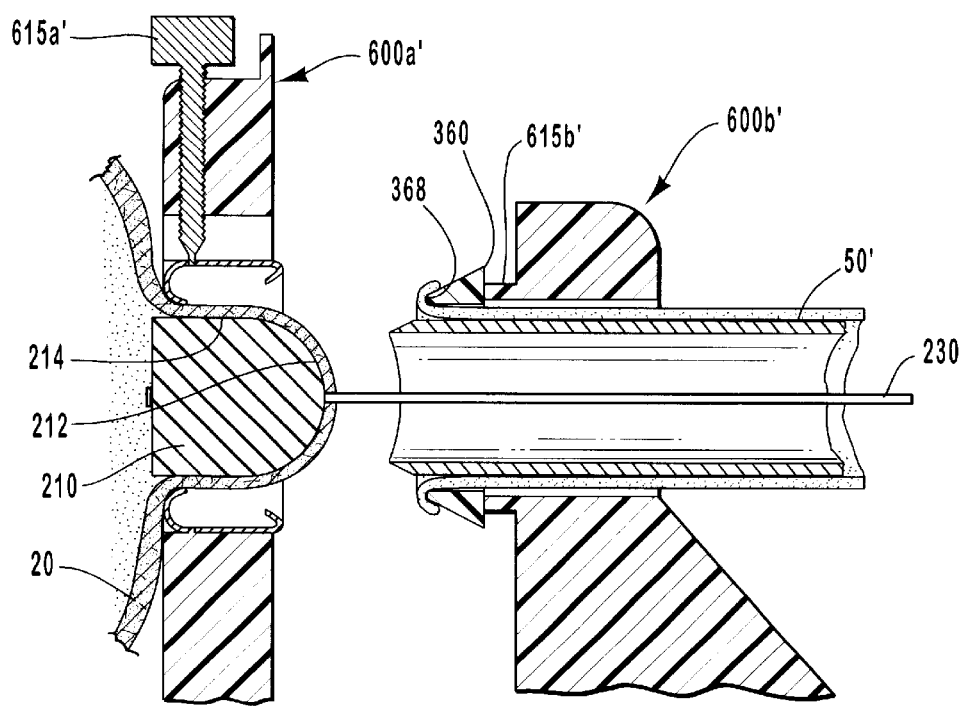
FIG. 12C is a cross-sectional view of the compression plate apparatus shown in FIG. 12B as anvil apparatus distends a blood vessel into the compression plate apparatus.
Figure 12D:
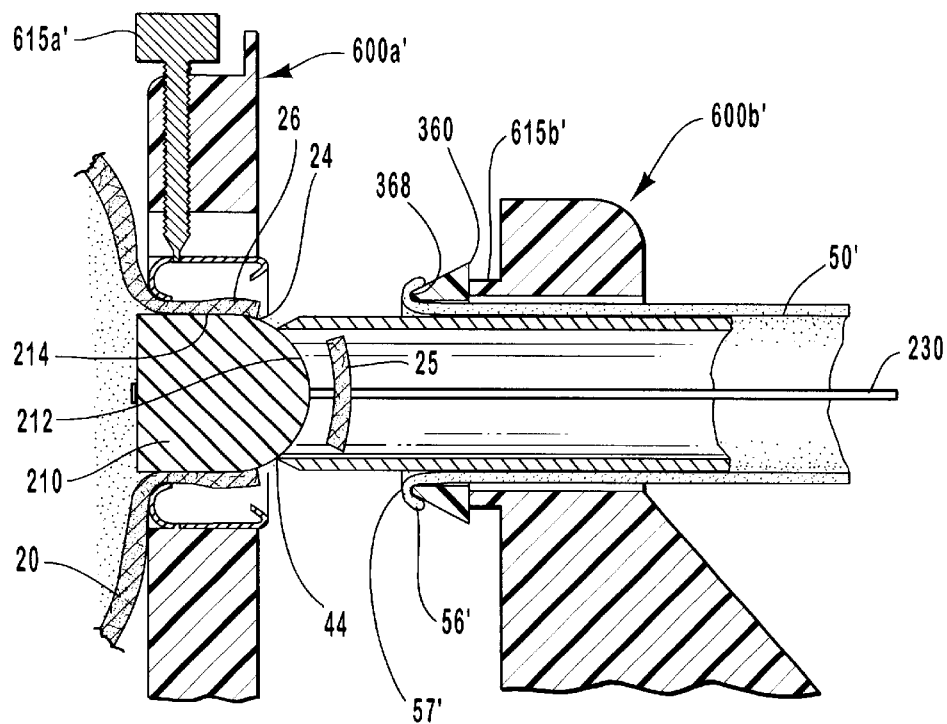
FIG. 12D is a cross-sectional view of the compression plate apparatus shown in FIG. 12A in the next phase as a cutter and an anvil are engaged to form an opening in the vessel.

FIG. 12C depicts anvil 210 extending through first compression opening 320a with its landing 214 abutting first holding tabs 314a while cutter 400 and second compression plate are opposite spherical engaging end 212 with anvil pull 230 extending through cutter 400. FIG. 12D depicts cutting edge 414 pressing against spherical engaging end 212 above the portion where spherical engaging end terminates at landing 214.

FIG. 12E depicts compression plate apparatus 300' as it is being compressed and as portion 26 defining vessel opening 24 is being everted. More particularly, compression plate 310b' has been moved toward compression plate 310a' as second plate engager 600b' is pushed toward first plate engager 600a'. Note that the everted portion 56' of graft vessel 50', more particularly the portion 57' opposite from the rim 368, is urged against portion 26 that defines first blood vessel opening 24 in a manner such that portion 26 is being everted. This eversion process is augment by landing 214 of anvil 210 which allows portion 26 to rest on landing 214 and be plowed upward by everted portion 56'. The length of portion 26 is sufficient for this eversion process since vessel 20 was distended and pulled into the snap-fit compression plate apparatus by the action of anvil 210. FIG. 12E also depicts grasping portion 354 sliding on flaring surface 362 as pivot portion 352 extends radially outward.

FIG. 12F depicts portion 26 fully everted on holding tab 314a' such that portion 27 opposite from rounded tip 316a' is held in contact with the portion 57' of vessel 50 opposite from rim 368. After compression plate apparatus 300' has been compressed to join portion 26 of blood vessel 20 that defines first vessel opening 24 to portion 56' of second vessel 50' that defines graft vessel opening 54' then first vessel 20 and second vessel 50 are anastomosed together and are in fluid communication. Anvil apparatus 200 and cutter 400 have been removed upon the completion of the procedure through lumen 58 of graft vessel 50. More particularly, once the anastomosis is completed then anvil pull 230 is pulled so that it draws anvil 210 through openings 320a, 320b' and 372 of compression plate apparatus 300' such that anvil apparatus 200 is removed along with cutter 400 through lumen 58'. FIG. 12G depicts vessel 20 anastomosed to vessel 50' after attachment actuation device 600' has been removed.

The mated locking components of first compression plate 300a' and second compression plate 300b', namely locking arms 350 and locking extension 366, are adapted to lock the compression plates together such that portion 26 defining first vessel opening 24 and portion 56' defining the second vessel opening 54' are joined without being penetrated. Such locking components are an additional example of means for locking the compression plates together. Note these locking means are integral parts of each compression plate so it is not necessary to separately attached the locking means to the compression plate apparatus after it has been used to anastomose the vessels.

Figure 14C:
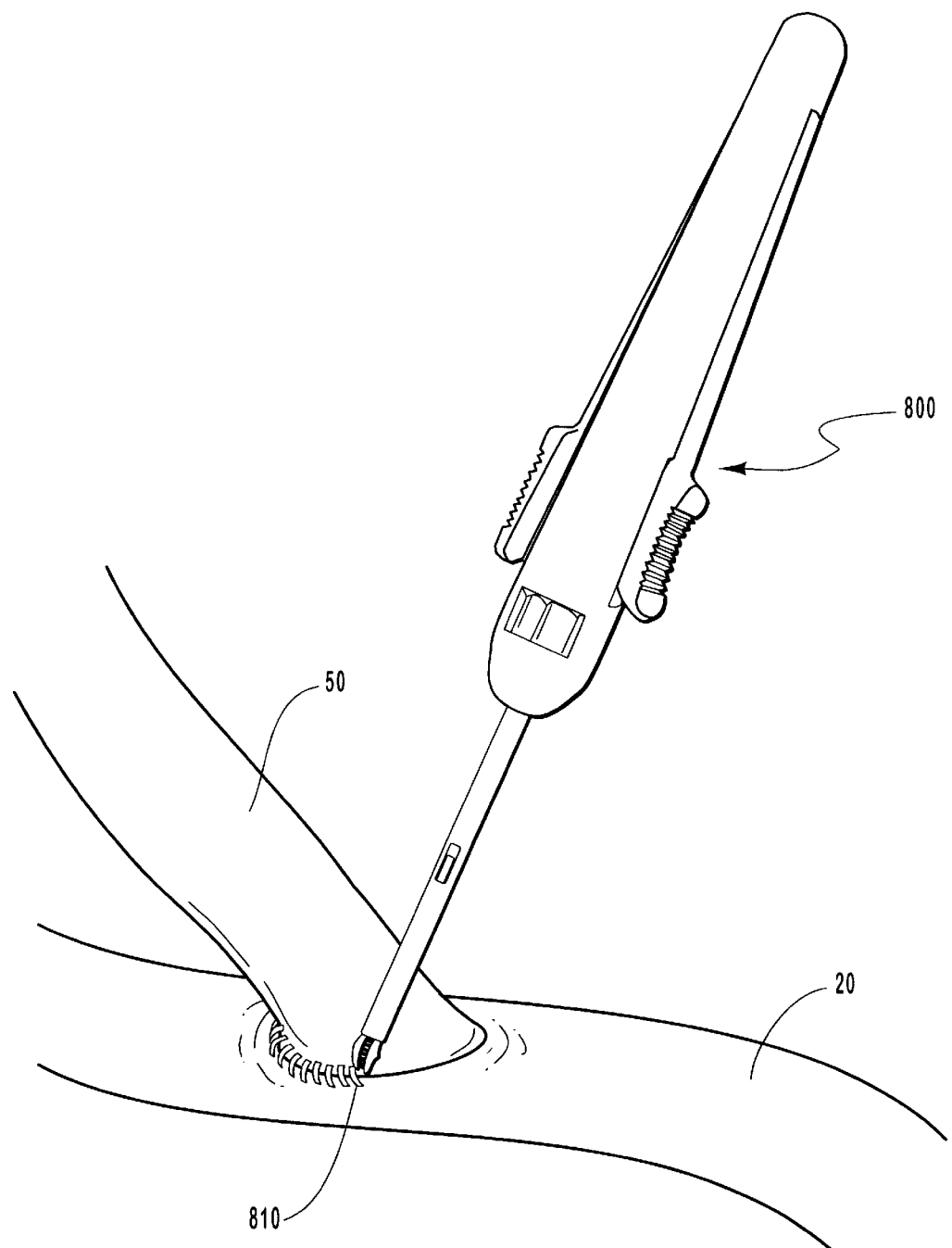
FIG. 14C is a perspective view of a clipping device applying clips to join two vessels in a nonperpendicular orientation.

FIG. 13 depicts another embodiment of a guided compression plate apparatus 300" which has components that are almost all identical with those of compression plate apparatus 300 except that the components of compression plate apparatus 300" are oriented for use with a non-perpendicular anastomosis. Note that the end of vessel 50 has been cut at an angle so that it can be attached to a vessel as shown in FIG. 14C at an angle. Cutter 400' is also angled so that it can make a cut in a vessel that is elliptical in configuration. Openings 320a"–320b are also elliptical so that the aligned openings of compression plate apparatus 300', the first vessel opening and the second vessel opening are all elliptical. Guides 330" do not extend perpendicularly from ring 312a" like guides 330. Guides 330 are all parallel to each other and extend nonperpendicuarly from ring 312a" so that guide compression plate apparatus 300" is shaped like a parallelogram Guide apertures 334 are also formed with the same angled configuration of guides 330". This configuration enables compression plates 310a"–310b to be brought together in a manner such that second compression plate 310b" is moved in a fixed parallel orientation relative to first compression plate 310a".

Holding tabs 314a–b" may also be configured differently than holding tabs 314a–b in order to hold angled noncircular vessel openings. Note that guides 330" extend integrally from ring 312" and are not attached. Another difference is the use of guide barbs 336 to provide for irreversible advancement of second compression plate 310b" towards first compression plate 310a" as discussed above with regard to frictional engagements to prevent movement of the plates relative to each other after anastomosis. Note that while snap-fit compression plate apparatus 300' is shown being used for joining vessels with openings that are generally circular, the same principles shown with regard to apparatus 300" can also be used to modify apparatus 300' for use with noncircular openings.

Compression plate apparatus 300, 300' and 300" are all examples of means for joining a portion of the first vessel that defines the first vessel opening to a portion of a second vessel that defines a second vessel opening. More specifically, they are examples of means for mechanically joining the portion of the first vessel that defines the first vessel opening to the portion of the second vessel that defines the second vessel opening. Other examples of means for mechanically joining the vessels include suture thread, staples, clips, and combinations thereof. An example of the use of staples or clips is shown in FIG. 14C.

Figure 14D:
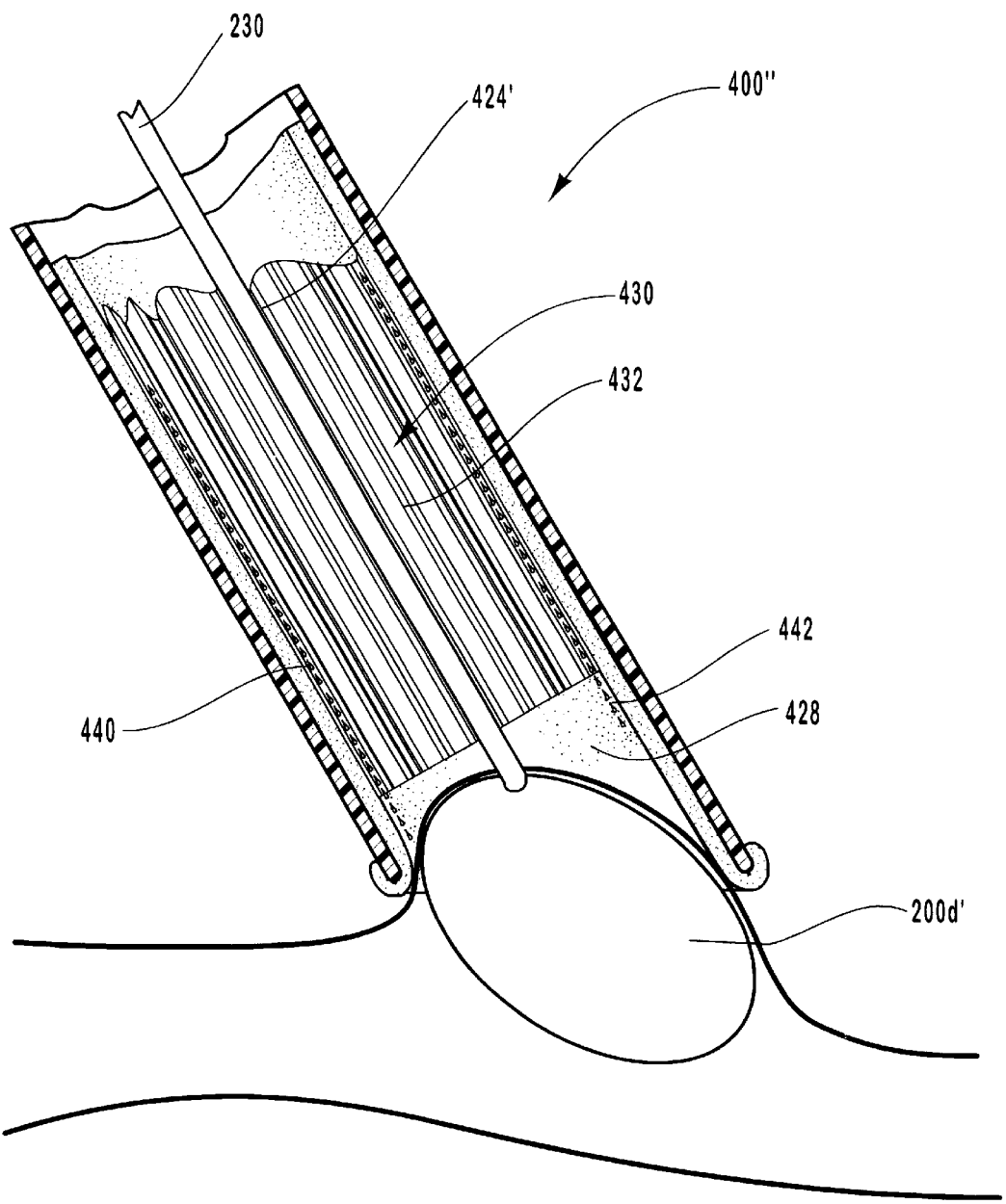
FIG. 14D is a cross-sectional view of the device capable cutting, delivering radiation for soldering, delivering adhesives and other fluids.

The joining means also includes means for chemically joining the vessels. Examples of means for chemically joining the vessels include biocompatible adhesives or glue; solder, biological procoagulant solution; a combination of a chromophore and solder, and combinations thereof. These materials are discussed in detail in the Background section. FIG. 14D depicts such materials being delivered in accordance with one embodiment.

The joining means also includes radiation-based means for joining the vessels. Examples of radiation-based means for joining the vessels include tissue welding radiation; the combination of substances and radiation for laser sealing, and combinations thereof. The use of radiation for joining vessels is discussed in detail in the Background section. FIG. 14D also depicts radiation being delivered to join vessels.

Cutting Devices

The term "cutter" is used to refer to a tubular knife such as cutter 400. Cutter 400 is an example of a "cutting device" which is a term used to refer to cutters and any other instrument used to form an anastomosis fenestra or opening that does not rely on the application of mechanical pressure, such as cutting device 400". While cutters that use a radiation source, such as a surgical laser, that emit radiation of the appropriate characteristics to open the anastomosis fenestra in the receiving blood vessel wall are useful, cutting devices such as cutter 400 are generally less expensive. Cutter 400 is preferably formed from stainless steel such that it is sufficiently inexpensive to be a disposable, single use item.

These cutting devices disclosed herein are all examples of cutting means for forming an opening in the wall of the first vessel at the anastomosis site through engagement with the anvil of an anvil apparatus as an engaging means holds the anvil pull of the anvil apparatus after receiving the anvil pull through the cutting means. The cutting devices engage an anvil to form the vessel opening in any suitable manner. For example, the cutting device may be pushed against the anvil, the anvil may be pulled against the cutter or both may simultaneously occur such that anvil is pulled as the cutter pushes against the anvil.

Cutter 400 is shown in numerous drawings, however, FIGS. 6C–6E, show its full length and its use in combination with external anastomosis operator 700. FIG. 6E provides the best view of cutter 400. Cutter 400 is shown in FIG. 6B–E as including a tip portion 401 and an extension portion 402, however, cutter 400 is shown elsewhere as being integral.

Anvil pull 230 is shown in FIG. 6C extending through cutter 400. Cutter 400 is hollow so it has a chamber 420 between the sidewalls of cutting tube 410. Cutter 400 may also have an optional centering core 422 that extends at least part way though chamber 420. Centering core 422 has a centering conduit 424 that assists in centering anvil pull 230 in cutter 400 such that anvil pull 230 is essentially parallel with the sidewalls of cutting tube. Centering core 422 preferably has a tapered access to guide anvil pull 230 into centering conduit 424. Another example of a centering conduit is provided by a centering conduit 424' of cutting device 400' shown in FIG. 14D, as discussed below in greater detail.

It is not always necessary for cutter 400 to have a centering core or for other cutting devices to have a centering core or a centering conduit. When the engaging end of the anvil is spherical and the cutter is spherical and is configured such that it permits part of the spherical engaging end of the anvil to be positioned in cutter chamber 420 then the cutter self centers on the spherical engaging end. The entire cutting device need not be hollow. For example, cutting device 400" has a recess 428 at its cutting end that is deep enough to permit the engaging end of anvil 200d' to extend into recess 428 so that anvil 200d' may be centered and seated. Accordingly, the cutting end is preferably adapted to receive a portion of the engaging end into the cutter to enable the engaging end to self center and be seated. Also, the engaging end is preferably convex and more preferably spherical.

As shown in FIG. 6C, cutter 400 is spring biased by a spring biasing device 450 that is described in detail below in the External Anastomosis Operator section. However, to appreciate the benefits of spring biased cutting it should be understood that distal end 418 of cutter 400 is received into a moveable cutter cup 458 which can push against spring 460. The pressure of spring 460 against cutter cup 458 enables cutter 400 to apply pressure against anvil 210 as anvil 210 is pulled against cutter 400. This makes it easier to cut the vessels as force is being applied in both directions.

More particularly, it reduces the amount of force that would otherwise be required if the only force being applied was through the advancement of anvil 210 by pulling anvil pull.

A spring biased cutter also enables the cutter to be pushed back by anvil 210 to allow anvil 210 to further distend the wall of vessel 20 as shown in FIGS. 4A–4B, FIGS. 6D–6E, FIGS. 12C–12E, FIGS. 15B–15C and FIGS. 16D–16E. As anvil 210 pushes cutter 400 through vessel 20, anvil 210 causes cutter 400 to retract, however, increasing resistance is encountered as spring 460 becomes further compressed. So cutter 400 applies increasing amounts of pressure to vessel 20 as anvil 210 continues to stretch the wall of vessel 20 into compression plate apparatus 300. By optimizing features such as the tension of the spring and the length of cutter, vessel 20 is distended far enough into compression plate apparatus 300 to leave sufficient lengths of the vessel in the compression plate apparatus for capturing in the subsequent eversion process onto holding tabs 314a. It has been found that about 17–18 lbs or about 20 lbs is generally required to form the anastomosis fenestra.

The gradual increase in pressure also serves to assist a spherical engaging end 212 of anvil 210 to self center on cutter 400. Since the pressure increases gradually, if anvil 210 is initially misaligned on cutter 400 then the gradual increase in pressure causes the anvil to be gradually drawn to center as the spherical engaging end 212 is pulled into chamber 420 or recess 428 of the cutting device. If pressure is applied too rapidly, the sharp cutting edge 414 of a cutter such as cutter 400 may dig into anvil 210 before anvil 210 can slide into a centered orientation. Accordingly, the use of a cutter with at least a recess at its cutting end and a spherical engaging end accommodates imperfections in the alignment of the cutter and the anvil.

FIGS. 14A–14B depict a simple combination of a cutter engaging an anvil as the anvil pull 230''' is advanced by an anvil pull engager 500' which holds and advances anvil pull 230'''. Note that distal end 232 of anvil pull 230 is threaded and anvil pull engager is essentially a wingnut that is correspondingly threaded. As anvil pull engager 500' tightens against the distal end 418 of cutter 400 then anvil pull 230 pulls anvil 200 until cutter 400 is engaged. Of course, an even simpler design is the manual application of pressure by pulling on anvil pull while pushing on cutter without an anvil pull engager.

FIG. 14C depicts an anastomosis fenestra formed through the use of a cutter such as cutter 400'. Cutter 400' works in the sane way as cutter 400 except that anvil 200b' has an elliptically shaped engaging end and cutter 400 has an elliptically shaped and angled cutting knife 412' and cutting edge 414'. Such a combination of an anvil with an elliptically shaped engaging end and a mated cutter with an elliptically shaped and angled cutting knife and cutting edge enable anastomosis to be formed as shown in FIG. 14C that involves the nonperpendicular attachment of a vessel to a side of another vessel. The configuration of the opening and the diameter of the opening to be formed depends on factors such as whether the opening is for a venotomy or an arteriotomy.

After the opening is formed by cutter 400' then the vessels may be joined in the same way that a vessel is joined perpendicularly to a side of another vessel. For example, the portions defining the openings may be clipped or staples together through the use of a clipping or stapling device 800 that delivers clips 800 or staples. If the vessels are mechanically joined through the use of sutures, staples or clips then it may be desirable to enhance the leak proof character of the anastomosis through the use of laser welding with a conventional laser welding device, such as an endoscopic laser welding devices. Similarly, the seal may be augmented through the appropriate use of biocompatible adhesives administered by conventional delivery devices, including endoscopic glue delivery devices. Additionally, a seal may be formed or strengthened by techniques such as laser soldering, including chromophore-enhanced laser soldering, and laser sealing.

FIG. 14D depicts a device identified as cutter 400'' which may be used to form the anastomosis fenestra to permit the angled attachment shown in FIG. 14C. Cutter 400'' has an element 430 that may be embodied by a surgical laser such as a cluster of optical fibers 432 that delivers appropriate radiation. Cutter 400'' also has an applicator 440 for delivering a fluid 442 such as biocompatible adhesives or glue; solder; biological procoagulant solution; a combination of a chromophore and solder, and combinations thereof. These materials may be delivered after the element 430 has been used or simultaneously depending on the objective. For example, if fluid 442 is an adhesive then applicator 440 can deliver the adhesive in a controlled manner after the radiation has been delivered to ablate the vessel wall to open the anastomosis fenestra. However, when utilizing element 430 for welding radiation or laser sealing then fluid 442 is preferably delivered before or is simultaneously delivered. Also, cutter 400'' may be used only to deliver glue after a mechanical cutter such as cutter 400' has been used. Adhesives and solder may be used alone, or as discussed above, adhesives and solder may be utilized to further seal an anastomosis that utilizes a mechanical devices such as clips as shown in FIG. 14C.

External Anastomosis Operators

The positioning of the compression plate apparatus and the operations of pulling or holding anvil pull 230, making an opening, and compressing the compression plates together as described in the foregoing sections can be accomplished by manually actuating these elements or with the aid of devices such as external anastomosis operator 700. One advantage derived form the use of a device such as external anastomosis operator 700 is that such devices have a series of actuators, and by manipulating these actuators the operator can effectuate the different operations at the anastomosis site without actually having to manually and directly operate each element itself As shown in FIG. 6A, external anastomosis operator 700 has a body 710 with an optional handle 720. Attached to body 710, are the main components of operator 700, as identified in FIG. 6A. These main components are cutter 400, spring biasing device 450, an anvil pull engager 500 which includes an anvil pull holder 530 and an anvil pull advancer 560, and an attachment actuation device 600.

FIG. 6B provides an exploded perspective view of all of the components of external anastomosis operator 700 so it is with reference primarily to this view that the details of operator 700 are understood. FIGS. 6C–6E provide cross-sectional views of operator 700 depicting the steps for using operator 700.

Cutter 400 is shown in FIG. 6B–E as including a tip portion 401 and an extension portion 402. Note that cutter 400 is shown elsewhere as being integral. The advantages of using a spring biasing device 450 to apply pressure against the distal end 418 of cutter 400 are explained above in the Cutting Devices section. However, the components of spring biasing device 450 are described in this section.

Spring biasing device 450 has a spring mount 452 that is mounted to body 710 via spring mount pins 454. A rotatable spring housing 456 is threadably engaged by spring mount 452. Loaded into rotatable spring housing 456 is a cutter cup 458 that is configured to hold distal end 418 of cutter. Cutter cup 458 has a flange that is pushed against a flange at the proximal end of rotatable spring housing 456 such that cutter cup 458 is held in the proximal end of spring housing 456. A spring 460 is positioned within a spring sleeve 462. Spring 460 and spring sleeve 462 have ends that abut cutter cup 458 and opposite ends that abut threaded jam screw 464. Threaded jam screw 464 is accessible via the distal end of spring mount 452 so that it may be rotated to increase or decrease the tension of spring 460 against cutter cup 458.

Cutter cup 458 moves within rotatable spring housing 456 against spring 460. As discussed generally above in the Cutting Devices section, the pressure of spring 460 against cutter cup 458 enables cutter 400 to apply pressure against anvil 210 as anvil 210 is pulled against cutter 400. This makes it easier to cut the vessels as force is being applied in both directions. It also enables cutter 400 to be pushed back by anvil 210 to allow anvil 210 to further distend the wall of vessel 20 as shown in FIGS. 4A–4B until sufficient pressure is applied by spring 460 to bias cutter 400 forward and by the advancement of anvil 210 by anvil pull 230 to cut the vessel. The gradual increase in pressure also serves to assist a spherical engaging end 212 of anvil 210 to self center on cutter 400. More particularly, anvil 210 may be initially misaligned such that the center of engaging end from which anvil pull extends is positioned on cutting edge 414. A rapid application of pressure would lock such a misalignment while a gradual increase enables the curvature of spherical engaging end to guide the anvil into a centered orientation.

Another function of spring biasing device is to set the position of cutter 400. Rotatable spring housing 456 has a notch 457 at its distal end that enables a screw driver to rotate rotatable spring housing 456 within spring mount 452 to advance or retract rotatable spring housing 456 within spring mount 452. Movement of rotatable spring housing 456 also moves cutter cup 458, thereby determining the location of distal end 418 of cutter 400 within operator 700. Of course advancement of cutter cup 458 towards the proximal end of operator 700 causes cutting knife 400 to be engage anvil 210 closer to first compression plate 310a while retraction of cutter cup 458 towards the distal end of operator 700 causes cutting knife and anvil to engage each other closer to second compression plate 310b. The position of cutter 400 is preferably set to enable vessel 20 to be distended in a manner that is optimal for then subsequently everting the portion defining the newly formed opening onto holding tabs 314a. To carefully identify the length that rotatable spring housing 456 is advanced or retracted, a detent 470 is threaded into spring mount such that it can contact rotatable spring housing and engage the grooves 471 of rotatable spring housing in a manner that enables detent 470 to click as each groove is rotated past detent 470.

Obviously spring biasing device 450 has many variables that impact the manner in which cutter 400 is used in combination with external anastomosis operator 700. Some of these variables include the inherent tension of spring 460, the tension of spring 460 as caused by the position of threaded jam screw 464 in spring mount 452 against spring 460, and the position of the surface which distal end 418 of cutter 400 abuts, namely cutter cup 660 as determined by the position of rotatable spring housing 456 within spring mount 452.

Spring biasing device 450 is an example of spring biasing means for providing tension against the cutting means as the cutting means engages the anvil means of the intraluminally directed anvil apparatus. The spring biasing means provides an amount of tension that enables the cutting means to form the first vessel opening after the wall of the first vessel has been distended by the action of the anvil means being pulled into the openings of the compression plate assembly such that forming the first vessel opening results in at least partial eversion of the portion of the first vessel defining the first vessel opening.

As indicated above, anvil pull engager 500 has two primary components including an anvil pull holder 530 and anvil pull advancer. Anvil pull holder 530 receives anvil pull 230 via spring biasing device 450. More particularly, anvil pull 230 extends through cutter cup 458, rotatable spring housing 456, spring 460 and sleeve 462 around spring 460, and out of threaded jam screw 464.

Anvil pull holder 530 includes a holder mount 532 positioned in track 730 of body 710. In this embodiment, holder mount is moveable so that the anvil pull can be advanced after it is held However, in other embodiments, the anvil pull holder may just lock the anvil pull into position such that the cutter is moved against a stationary anvil. Similarly, the spring biasing device 450 may be eliminated so that the vessel is cut only by pressure exerted by the anvil pull against the cutter. As discussed above, while the cutter and the anvil may engage each other in these arrangements, it is preferable for the cutter to apply some pressure as the anvil pull is advanced against the cutter.

Holder mount 532 may be utilized in different ways to hold anvil pull 230. Holder 530 has a split cone 534 inserted into a tapered chamber 536 against a spring 538. Anvil pull 230 extends through apertures in holder mount 532, spring 538, split cone 534 and out of an aperture centered in holder knob 540. Holder knob 540 is threadably engaged by holder mount 532 such that rotation of holder knob 540 advances split cone 534 in tapered chamber 536 causing split cone to lock onto anvil pull 230. As shown in FIG. 6B, holder mount is slotted at its distal end as is holder knob. By aligning slot 542 of holder knob 540 with the insert slot 544 of holder mount, anvil pull 230 can be bent so that it extends through both holder knob slot 542 and insert slot 544. Then holder knob 540 can then be rotated so that the bent portion of anvil pull 230 is rotated into one of the locking slots 546a–b' that extend perpendicularly from insert slot 544. This securely locks anvil pull into position. Anvil pull 230 can be locked through the use of slots instead of or in addition to the use of split cone 534 in tapered chamber 536.

The anvil pull holders described herein are examples of holding means for holding the anvil pull extending from an anvil. The anvil pull advancers described herein are examples of advancement means for pulling the anvil pull once the anvil pull is held by the holding means. As indicated above, the anvil pull holder may have a fixed position such that it is not moveable. As also indicated above, however, the anvil pull holder is preferably moved via an anvil pull advancer. A fixed anvil pull holder and an anvil pull holder that is moveable via an anvil pull advancer are both examples of an anvil pull engagers. The anvil pull bolder and the anvil pull advancer may be separate components such as anvil pull holder 530 and anvil pull advancer 560 or be embodied by a component capable of both holding and advancing the anvil pull such as anvil pull engager 500' shown in FIGS. 14A–14B. These anvil pull engagers are all examples of engaging means for holding an anvil pull extending from an anvil. Once such engaging means holds the anvil pull then the engaging means can control the position of the anvil at the anastomosis site via the anvil pull.

Since anvil pull holder 530 is moveable it threadably engages rotatable lead screw 562 of anvil pull advancer.

More particularly, lead screw 562 is threadably engaged by anti-backlash nut 550 which is fixedly attached to holder mount 532. Anti-backlash nut 550 has an attachment face 552 through which a plurality of attachment face screws 554 extend to hold holder mount 532 and anti-backlash nut 550 together.

Lead screw 562 has a proximal pivot end 564 that rotates within a bushing 566 positioned within a recess in spring mount 452. Lead screw also has a distal pivot end 568 that is attached to advancer knob 570 to rotate lead screw 562. Advancer knob 570 rotates within an advancer knob mount 572 which is attached to body 710 in groove 730 via advancer knob mount bolts 574. As shown in FIG. 6C, distal pivot end 568 rotates in a bushing 576 positioned within an aperture of advancer knob mount 572.

Advancer knob 570 has a stem with a plurality of grooves 578 that engage a detent 580 to click so that the incremental rotation of advancer knob 570 can be carefully counted to determine the length that the anvil is moved in the compression plate apparatus as the anvil pull is advanced. As shown in FIG. 6C, detent 580 is threaded into advancer knob mount 572 such that it can contact grooves 578 in the stem of advancer knob 570 to click as each groove is rotated past detent 580.

FIG. 6D depicts advancer knob 570 being rotated to move anvil pull advancer 560 so that it can urge anvil pull 230 in a manner such that anvil 210 is advanced within compression plate apparatus 300. As advancer knob 570 is rotated, lead screw 562 is thereby rotated. Since anvil pull holder 530 is threadably engaged on rotatable lead screw 562 and is locked in track 730, anvil pull holder 530 can only move forward and backward as lead screw 562 is rotated.

FIG. 6E depicts attachment actuation device 600 being engaged. Attachment actuation device 600 has a first plate engager 600a and a second plate engager 600b. First plate engager 600a and a second plate engager 600b each respectively utilize an optional adaptor 610a–b to engage first and second compression plates 310a–b. Note that attachment actuation device 600' described in reference to FIGS. 12CA–12G does not utilize these optional adapters since its first and second plate engagers 600a'–600b' are adapted to directly engage first and second compression plates 310a'–310b'.

First plate engager 600a and second plate engager 600b each have a cutter aperture 620a and 620b. Cutter 400 extends through these aligned apertures 620a–b. First plate engager 600a is positioned on rail 640 such that it extends slightly beyond cutting edge 414 of cutter 400. This difference in length enables first compression plate 300a to be held slightly beyond cutter in a manner that permits the wall of vessel 20 to be pulled into compression plate apparatus as shown in FIG. 6D–6E and distended as needed.

Rail 640 is attached to body 710 via rail pin 642. A groove pin 644 extends through rail 640 as described in greater detail below. A first plate engager pin 646 holds first plate holder 600a on the proximal end of rail 640.

First plate engager 600a is fixedly mounted on rail 640 via pin 646 while second plate engager 600b is movably mounted on rail 640. Second plate engager 600b has a groove 634 through which groove pin 644 extends. The configuration of groove pin 644 in groove 634 enables second plate engager 600b to be held in a fixed orientation such that it can be moved back and forth as needed with respect to first plate engager 600a.

Second plate engager is moved on rail 640 by rotating threaded compressor sleeve 650 which engages a threaded rail sleeve 648. Threaded rail sleeve 648 may be adhered onto rail 640 or be an integral component. Rail 640 and its threaded rail sleeve 648 or threaded rail portion combined with compressor sleeve 650 are means for advancing one plate engager towards the other plate engager.

First plate engager 600a has an adaptor 610a that preferably has two halves 612a and 614a. As best seen in FIG. 6C, when these halves are joined together, adaptor 610a has a proximal side configured such that there is a curvature from the perimeter inward to direct the engaging end 212 of anvil 210 into the aperture defined by the inner perimeter of adaptor 610a The distal side of adaptor 610a has a recess 616 adapted to the size of outer periphery 311a of first compression plate 310a. Sets screws 615 lock first compression plate 310a in place by pushing against adaptor 610a. Note that there are many other ways for locking first compression plate with first plate engager 600a such as the use of conventional quick release configurations.

Second plate engager 600b has an adaptor 610b or 610b' as respectively shown in FIGS. 5A–5B. Adapter 610b is integral while adapter 610b' has halves 612b and 614b. Either may be utilized, but when positioned on a graft vessel as shown in FIG. 5B that has reinforcements 57, which may be any conventional reinforcements such as fluorinated ethylene-propylene (FEP) strands bonded onto a PTFE graft vessel, the reinforcements make it difficult to remove the adapter that it integral like adaptor 610b. As best seen in FIG. 5A, adaptor 610b is tubular to receive the vessel and has a flange 616b that extends around the tube and is sized to push against exterior side 324b of second compression plate 310b. Apertures 618b are located in flange 616b that are oriented and sized to slidably receive guides 330 of compression plate apparatus 300. Adapter 610b also has a flange with apertures so that it can fit over second compression plate 310b as shown in FIG. 5B. These features are more clearly shown in FIG. 6C which provides a cross-sectional view of assembly 390 shown in FIG. in FIG. 5B. Note that adaptor 610b is also shown in FIG. 16C, which is a close-up view of the proximal portion of applicator 700, however, adaptor 610b is pushed back from its position of engagement with second compression plate 310b in order to more clearly see other features of operator 700.

Figure 15A:
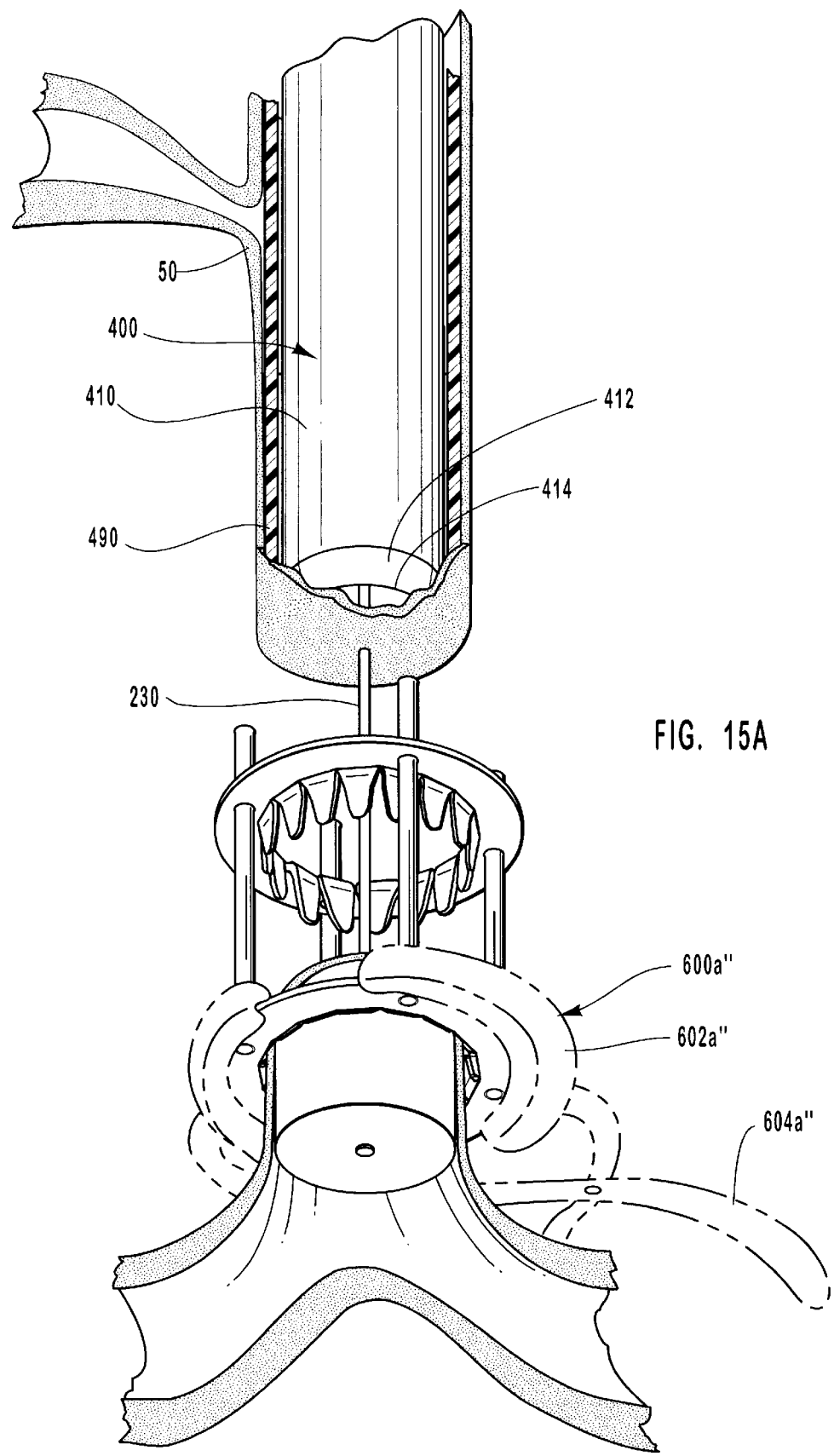
FIG. 15A is a perspective and partial cross-sectional view of the compression plate apparatus shown in FIG. 3A being used in a side-to-side anastomosis while the first compression plate is held.
Figure 15B:
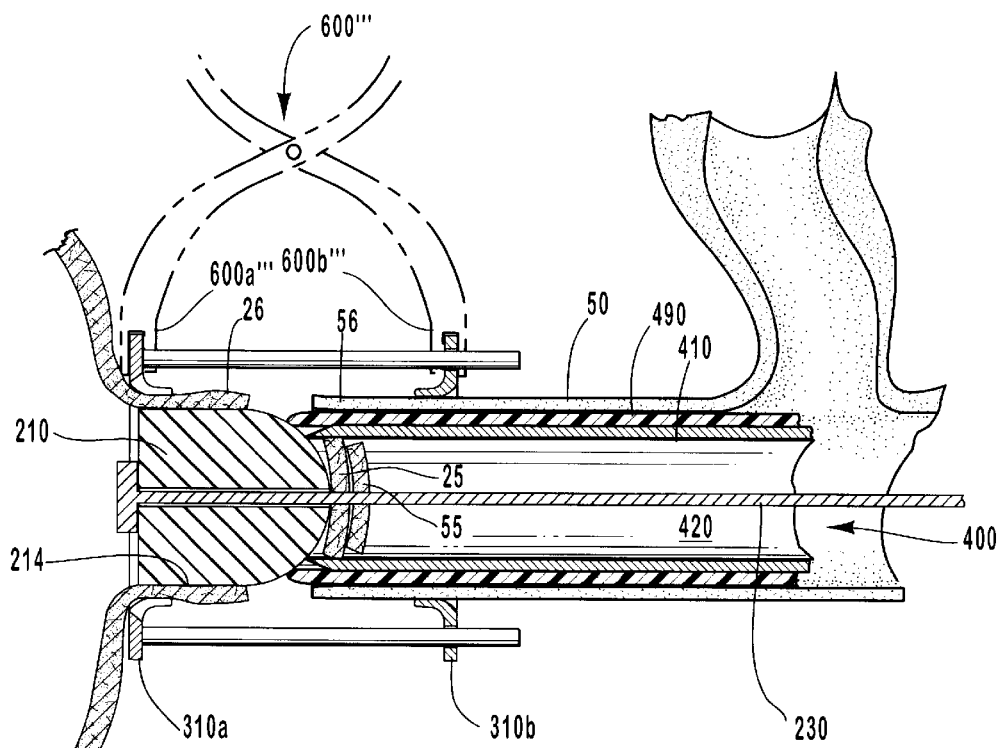
FIG. 15B is a cross-sectional view of the compression plate apparatus shown in FIG. 15A in the next phase as a cutter and an anvil are engaged to form an opening in the vessel.
Figure 15C:
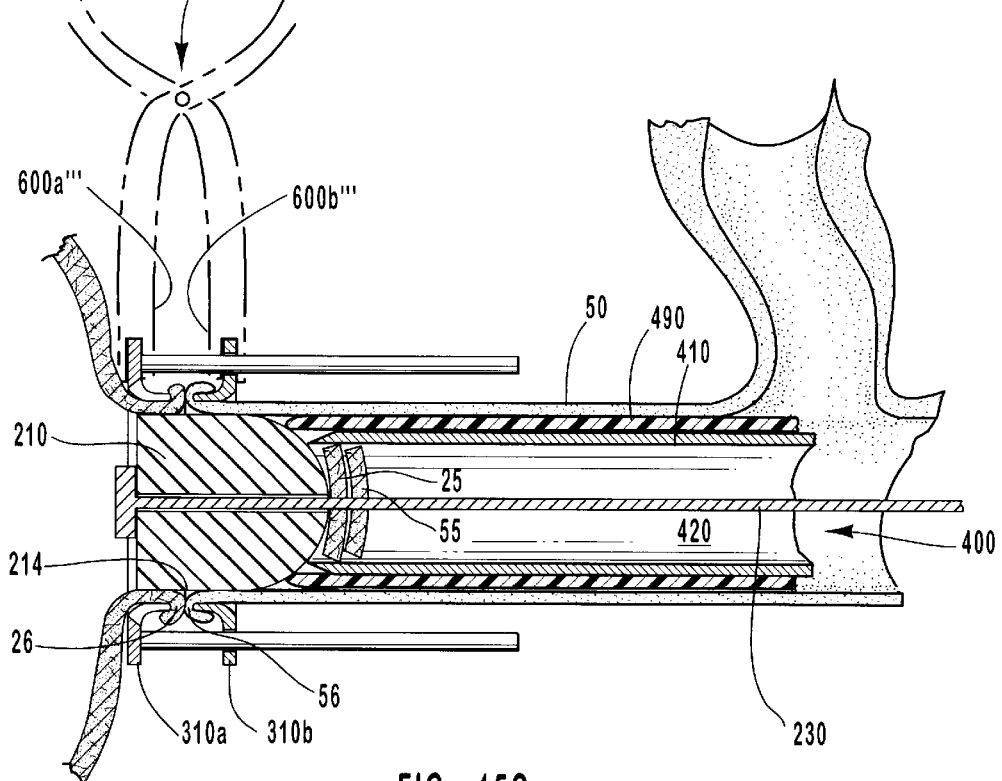
FIG. 15C is a cross-sectional view of the compression plate apparatus shown in FIG. 15B in the next phase after the second compression plate has been compressed towards the first compression plate by an attachment actuation device such that the everted graft vessel contacts the everted blood vessel.

As discussed below in the Side-to-Side Anastomosis section in reference to FIG. 15A–5C, the attachment actuation device need not be part of the same apparatus with the anvil pull engager and the cutter. FIGS. 15A–15C show a device at 600a that is adapted to hold the first compression plate stationary as the anvil and the cutter are engaged. Device 600'" is also discussed below in reference to FIG. 15A–15C which is used to approximate compression plates 310a–b by pushing second compression plate 310b on guides 330. Attachment actuation device 600, 600' and 600'" are examples of attachment actuation means for actuating a compression plate assembly. In addition to device 600, 600', and 600'", device 600a" is also an example of an attachment actuation device adapted to hold the first compression plate stationary as the anvil and cutting device are engaged to form an opening.

As noted above, compression plate apparatus 300, 300', 300" are examples of means for joining a portion of the first vessel that defines the first vessel opening to a portion of a second vessel that defines a second vessel opening. Accordingly, attachment actuation device 600 is more broadly an example of attachment actuation means for actuating means for joining a portion of the first vessel that defines the first vessel opening to a portion of a second vessel that defines a second vessel opening.

Other examples of attachment actuation means include mechanical, chemical or radiation-based attachment actuation means for actuating the anastomosis of the portion of the first vessel that defines the first vessel opening to the portion of the second vessel that defines the second vessel opening. Examples of mechanical attachment actuation means include a suturing device such as a needle and thread; and a stapling or clipping device such as device 800. Examples of chemical attachment actuation means include a device such as device 400" for delivering biocompatible adhesives or glue; solder; biological procoagulant solution; a combination of a chromophore and solder, and combinations thereof Examples of radiation-based attachment actuation means include a device such as device 400" for radiation welding, a device for laser sealing, and combinations thereof As shown by device 400 and 800, combinations of these attachment actuation means are also possible.

As mentioned, the attachment actuation device need not be part of the same apparatus with the anvil pull engager and the cutter. This reduces the size of the instruments utilized. The size of the instruments utilized may also be decreased through the elimination of some of the features of operator 700. Operator 700 has the ability to modify its configuration in ways that enable it to be highly fine tuned to the parameters of a particular anastomosis procedure. Accordingly, it is highly useful in a research setting. However, applicators utilized in a commercial setting may have more standardized features that do not permit the same degree of modifications. For example, the spring biasing device may be preset to a standard setting. Use of such standard settings may assist in reducing the overall size of the operator. Note that the knobs and other features of external anastomosis operator that provide adjustments may also be achieved through other configurations that achieve these adjustments more rapidly. For example, instead of rotating compressor sleeve 650, compression plate apparatus 300 may be compressed through a configuration that is trigger activated.

As indicated above, anvil 210 may be positioned under direct image guidance from a distant percutaneous puncture to the anastomosis site based upon a diagnostic angiographic roadmap. A skin incision and limited vessel dissection is then performed at the anastomosis site to expose the vessel wall. Alternatively, the anvil may be externally positioned. In either event, once the anvil has been positioned such that it is against the interior of the vessel wall and the anvil pull extends from the vessel, then the anvil pull can be positioned in the operator 700 as shown in FIGS. 6C–6D for completion of the anastomosis procedure.

Side-to-Side Anastomosis

FIGS. 15A–15C depict the primary steps involved in achieving a side-to-side anastomosis. Cutter 400 is positioned in a vessel 50 by inserting the cutter into an end of vessel 50 and then twisting cutter 400 in vessel 50 such that cutting knife 412 is oriented towards the wall of vessel 50 as shown in FIG. 15A. Cutting knife 412 is prevented from cutting through the wall of vessel 50 by a sheath 490. Sheath 490 is positioned relative to cutter 400 such that the distal end 492 of sheath 490 extends beyond cutting edge 414. This configuration prevent cutting edge 414 from contacting vessel 50 until sheath 490 is pulled upward away from the anastomosis site.

Two separate instruments perform the task of attachment actuation device 600. First plate engager 600a" comprises tongs or pliers that have opposing grasping portion 602a" that extend integrally from pivotally attached handle portions 604a". Grasping portions 602a" are adapted to lock onto first compression plate 310a so that anvil 210 can be pulled through first compression plate opening 320a and distend the wall of vessel 20 into compression plate apparatus 300.

While first plate engager 600a", holds first compression plate 310a cutter 400, sheath 490 and vessel 50 are pushed through second compression plate opening 320b. Note that anvil pull 230 extends through the wall of vessel 50 and through chamber 420 of cutter 400. As cutter 400 is pushed through compression plate apparatus 300 and contacts anvil 230, sheath 490 is retracted.

FIG. 15B shows sheath 490 retracted so that cutter 400 and anvil 210 can engage each other such that openings 24 and 54 are simultaneously made respectively in vessel 20 and in vessel 50. After opening 54 is made, the portion 56 defining second vessel opening 54 rests on either sheath 490, cutting tube 410 or anvil 210. As the compression plates are brought together, portion 56 is advanced onto landing 214 against portion 26 of vessel 20 that defines first vessel opening 24.

FIG. 15B shows first and second compression plate apparatus being grasped by attachment actuation device 600'". More particularly, attachment actuation device 600'" has a first plate engager 600a'" that engages first compression plate 310a and a second plate engager 600b'" that engages first compression plate 310b such that the compression plates 310a–b can be approximated by pushing second compression plate 310b on guides 330.

FIG. 15C depicts attachment actuation device 600'" after it has pushed second compression plate 310b to first compression plate 310a. As second compression plate 310b is pushed toward first compression plate 310a, portion 56 of vessel 50 pushes against portion 26 of vessel 20 as these portions rest on landing 214 which causes the portions to respectively curl onto holding tabs 314a–b. When the second compression plate 310b is fully pushed into position by attachment actuation device 600'" then portions 26 and 56 are everted as shown on holding tabs 314a–b. Cut portions 25 and 55 remain on spherical engaging end 212 of anvil 210 and are removed with anvil apparatus 200, cutter 400 and sheath 490 through vessel 50.

It follows from the illustrations and the foregoing discussion that the compression plates of this invention can effectively be used for anastomoses at the end of tubular structures. This implementation of the teachings described above to end-to-end anastomosis simply requires ordinary skills in the art.

Externally Directed Anastomosis

Intraluminal access to the anastomosis site in the receiving blood vessel can be impeded by an occlusion or by blood vessel damage. In this case, a catheter cannot be used to intraluminally access the anastomosis site. Instead, other embodiments of this invention rely on the intraluminal access to the anastomosis site through a small incision, such as an arteriotomy, made at the anastomosis site. The anvil apparatus is then inserted through such incision and the abutting of the receiving blood vessel from its intraluminal space is then performed in the same way as when the anvil and wire are inserted with the aid of a catheter.

Figure 16A:
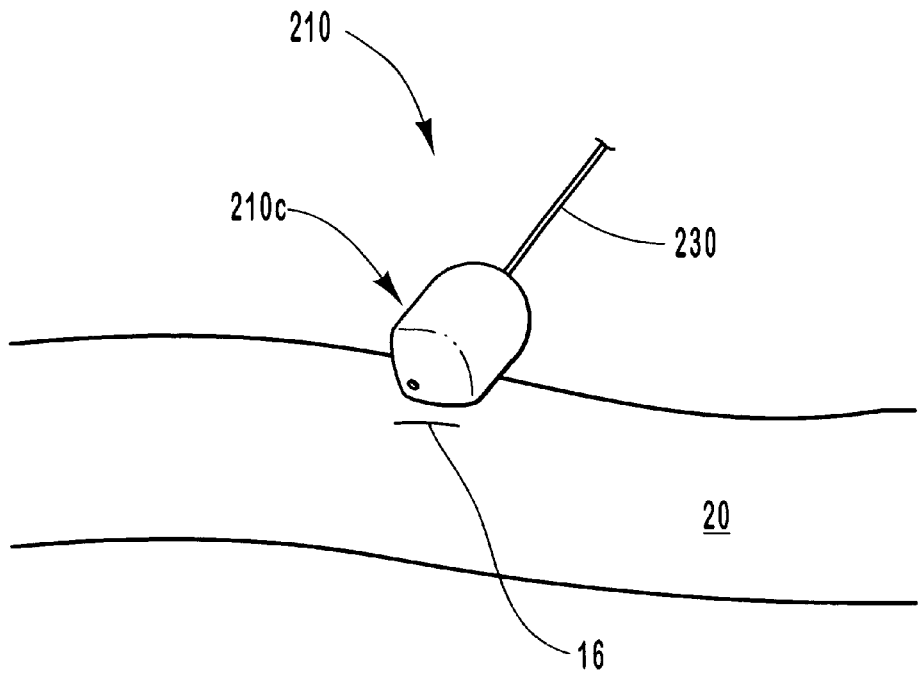
FIG. 16A is a perspective view of the anvil from FIG. 7C being inserted from the exterior of a blood vessel into the blood vessel lumen.
Figure 16B:
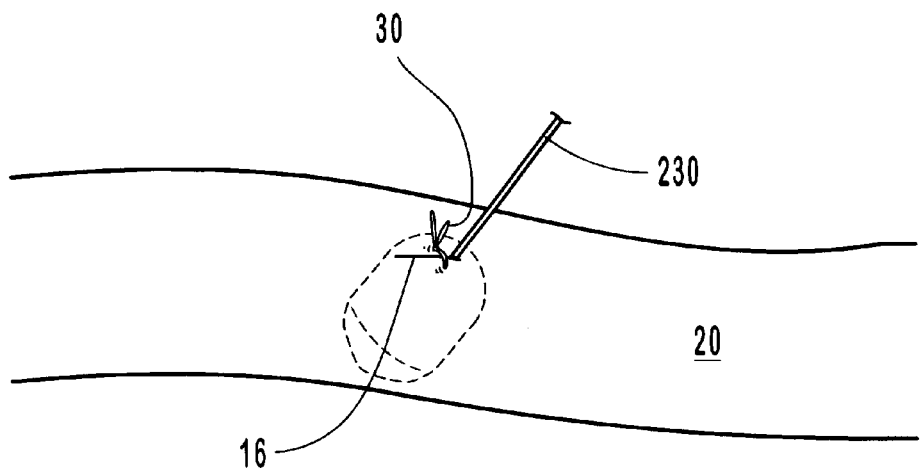
FIG. 16B is a perspective view of the blood vessel shown in FIG. 16A with the anvil depicted in phantom lines and a stay suture around the insertion opening.
Figure 16C:
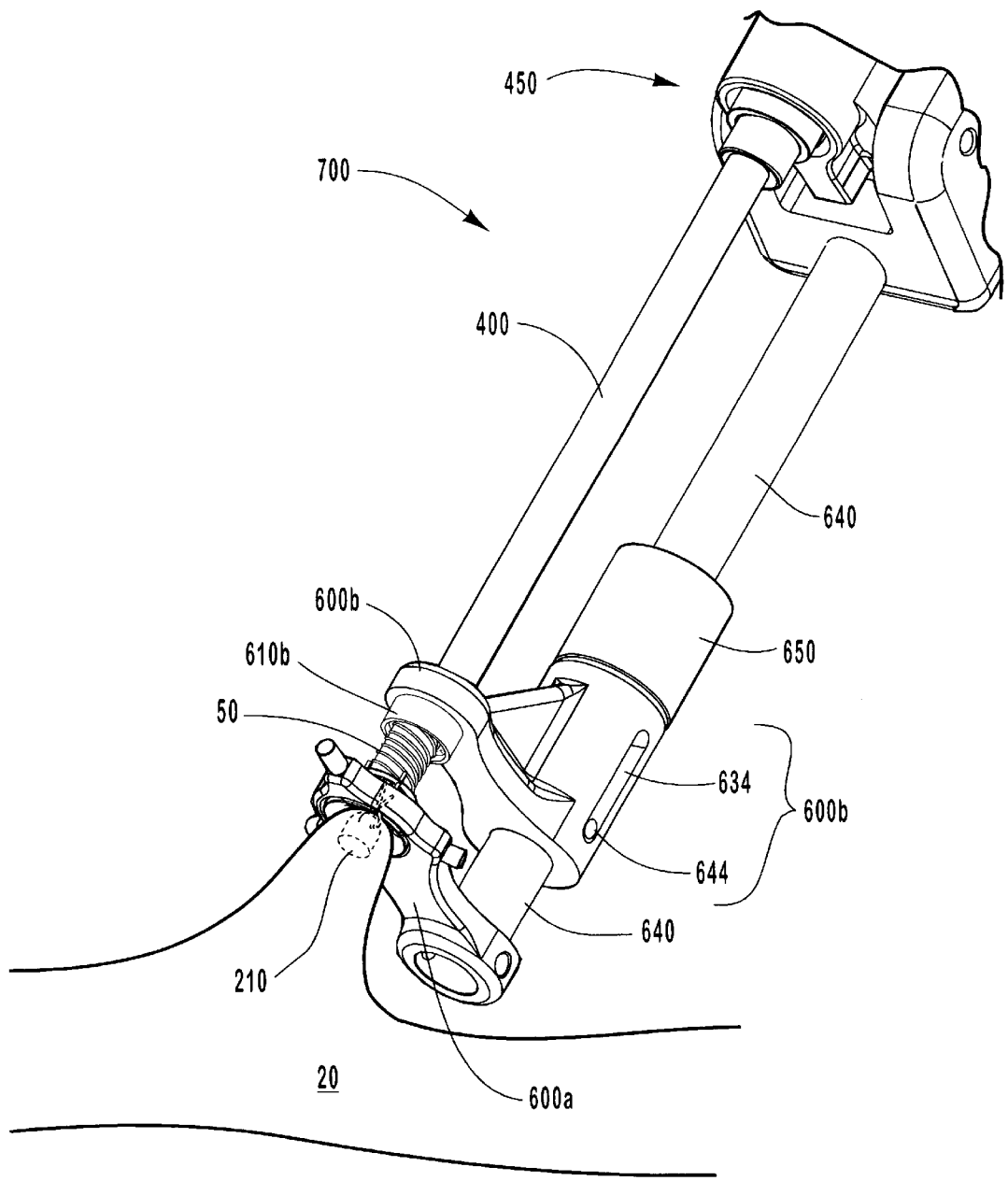
FIG. 16C is a perspective view of the external anastomosis operator cooperating with the anvil depicted in phantom lines to form an anastomosis.

FIGS. 16A–16E depict the primary steps involved in creating an anastomosis through the use of an externally positioned anvil apparatus in combination with an external anastomosis operator. FIG. 16A depicts an insertion opening 16 that has been made in vessel 20. Insertion opening 16 is preferably just large enough to permit an anvil such as anvil 210c as shown in FIG. 7C or any of the other anvils disclosed herein to be externally positioned into lumen 28. After anvil 210c has been inserted though a wall of first vessel 20 at insertion opening 16 that has been selected as an anastomosis site such that anvil pull 230 extends through insertion opening 16, then a stay suture 30 or several stay sutures may alternatively be used to partially close insertion opening 16.

As discussed above, in relation to FIG. 7D, it may be easier to insert an anvil extraluminally that has a tapered terminal end 218 such as terminal end 218c of anvil 210c or terminal end 219c of anvil 210d. Note that FIGS. 16C–16E, however, show an anvil 210 that has been inserted from outside of vessel 20 that has a nontapered terminal end 218.

As shown in FIG. 16C, anvil pull 230 can then be loaded into external anastomosis operator 700 for the anastomosis procedure. Note that once anvil pull 230 is loaded into external anastomosis operator 700 then the remainder of the procedure is the same as the anastomosis procedure outlined above in reference to an intraluminally positioned anvil apparatus.

Figure 16D:
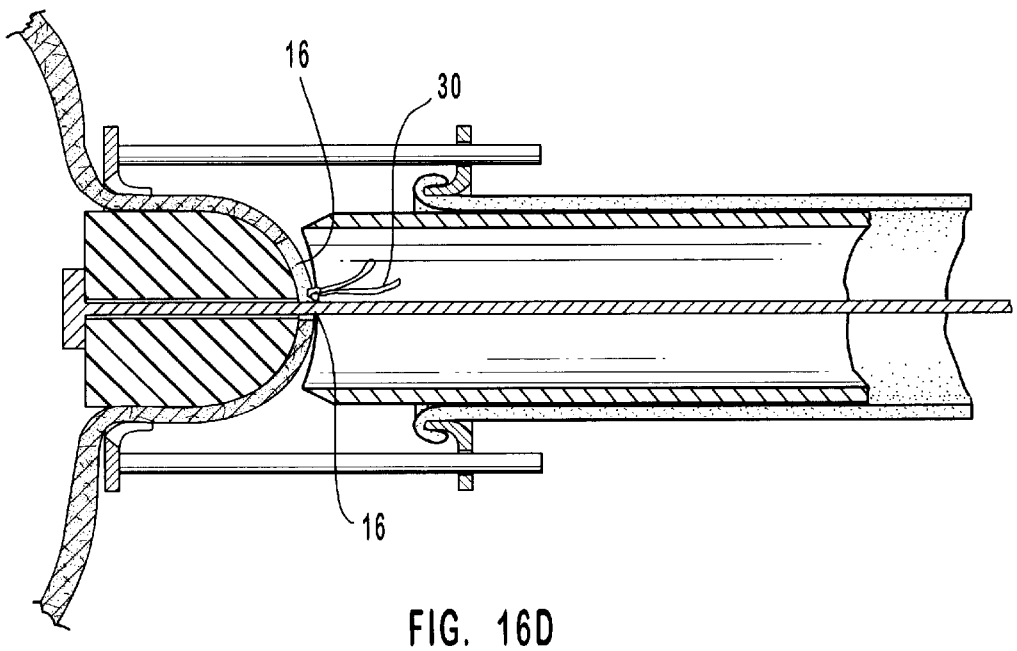
FIG. 16D is a cross-sectional view of the compression plate apparatus shown in FIG. 3A as the anvil apparatus distends a blood vessel having a stay suture around the insertion opening.

FIG. 16D depicts anvil pull 230 extending through compression plate apparatus 300 and into chamber 420 of cutter 400 such that cutting edge 414 self centers and seats on spherical engaging end 212 of anvil 210 just as is shown in FIG. 4A which depicts the use of an intraluminally positioned anvil apparatus. The only difference between the FIG. 4A and FIG. 16D is that initial piercing 15 is significantly smaller than insertion opening 16. Stay suture 30, however, enables anvil 210 to distend the wall of vessel 20 since stay suture 30 reduces the size of insertion opening 16.

Figure 16E:
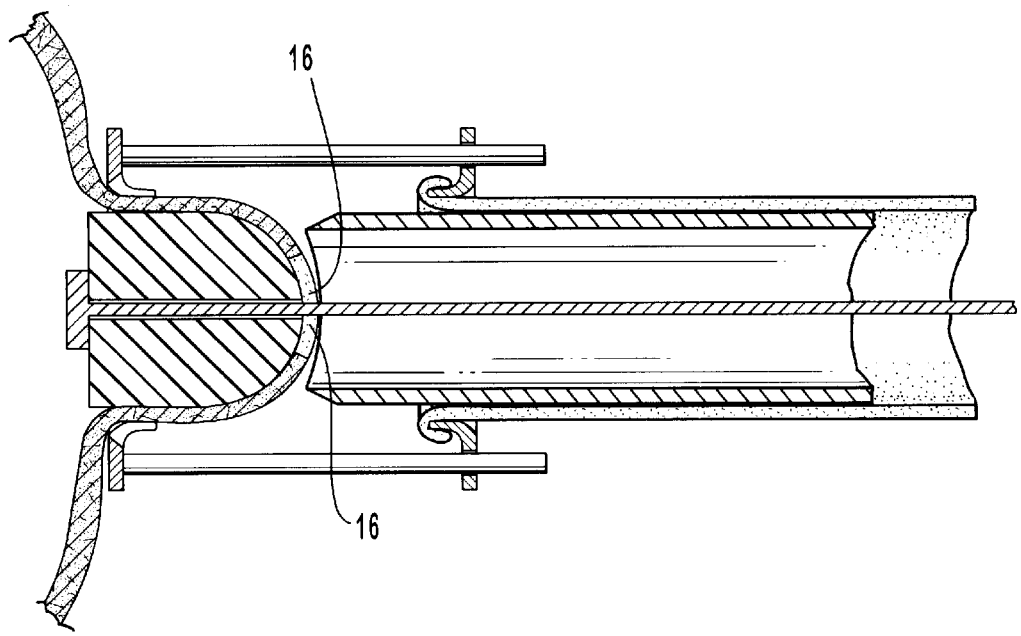
FIG. 16E is a cross-sectional view of the compression plate apparatus shown in FIG. 3A as the anvil apparatus distends a blood vessel after being inserted into the lumen of the blood vessel through an insertion opening.

FIG. 16E shows that it is possible to complete the same step shown in FIG. 16D without a stay suture 30 as long as the distension of the wall of vessel 20 does not cause insertion opening 16 to increase in size such that it becomes so large that a part of it is beyond the reach of cutting edge 414 of cutter 400. Accordingly, when distending a vessel that has an insertion opening 16 from an extraluminally positioned anvil instead of a relatively small initial piercing 15 from an anvil pull of an intraluminally directed anvil apparatus, it may not be possible to distend the vessel to the extent that is possible with an intraluminally directed anvil apparatus. For this reason landing 214 of anvil 210 shown in FIG. 16E is shorter than landing 214 of anvil 210 shown in FIG. 4A and in FIG. 16E.

Another method for enabling the wall of the vessel to be distended for the subsequent eversion process to occur in the desired manner involves the minimization of the size of insertion opening 16 through the use of expandable anvils. As discussed above in the Anvil section, anvils may be utilized that are expanded or deployed at the anastomosis site. For example FIGS. 9A–9B and FIGS. 10A–10B depict mechanically deployable anvils while FIGS. 11A–11B depict chemically deployable anvils. These same expandable anvils may be inserted through a small insertion opening from the exterior of the vessel into the lumen and then be deployed Accordingly, such expandable anvils have an initial collapsed position for insertion into the insertion opening and an expanded position. Once the anvil has been deployed then it can be used like solid or rigid anvils.

Just like the anvils that are intraluminally directed, anvils that are externally positioned into the lumen of a vessel preferably have an engaging end that is larger than cutter 400 such that portions of the engaging end 212 of the anvil extend beyond the cutting edge 414 when the cutter 400 or other cutting device engages the anvil and forms the first vessel opening. Stated otherwise, the cross-sectional area defined by the perimeter of cutting edge 414 of the cutting knife 412 is smaller than a cross-sectional area of the engaging end 212 at which cutting edge 414 engages engaging end 212. So for an expandable anvil, its engaging end preferably has a greater cross-sectional area than the cross-sectional area defined by cutting perimeter of the cutting device when in the expanded position. Also, the engaging end is also spherical such that cutter self seats and self centers on spherical engaging end 212. The advantages of these configurations are discussed in detail above in the Anvils section.

Figure 18A:
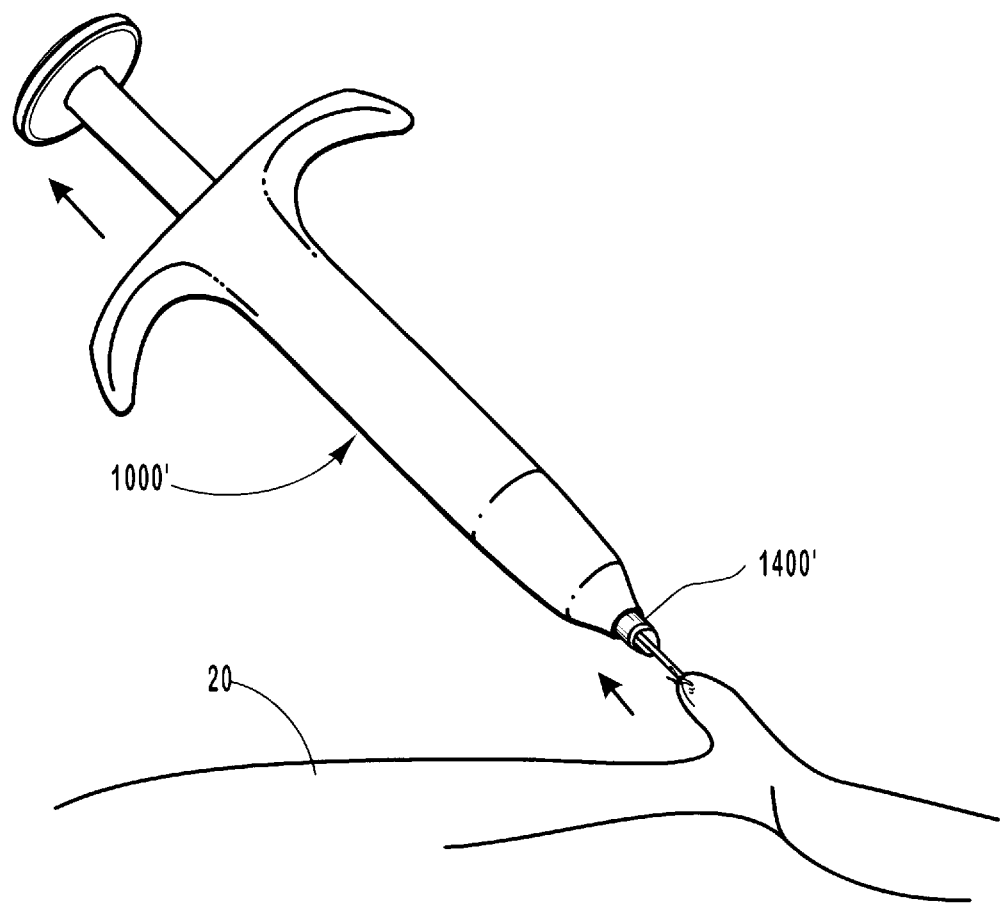
FIG. 18A is a perspective view of an externally positioned anastomosis fenestra cutting apparatus cooperating with an elliptical anvil
Figure 18B:
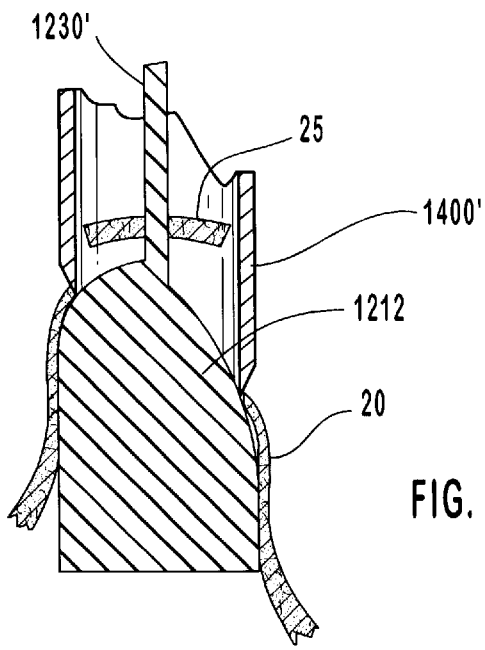
FIG. 18B is a cross-sectional view and the anvil pull of the externally positioned anastomosis fenestra cutting apparatus shown in FIGS. 18A pulling the anvil so that the engaging end of the anvil engages the cutter and forms an elliptical opening.

Note that as shown by FIGS. 18A–18B, externally positioned anvils may be used to form noncircular openings. These anvils have an engaging end with a shape corresponding to that of the cutting edge of a cutter such that the first vessel opening is formed as the noncircular cutting edge presses against the engaging end.

Externally Positioned Anastomosis Fenestra Cutting Apparatus.

As indicated above, the anvil is preferably sized at its engaging end to have a greater cross-sectional area than a cross-sectional area defined by the perimeter of the cutting edge of the cutting device such that portions of the engaging end of the anvil extend beyond the cutting edge when the cutting device engages the anvil and forms the first vessel opening. This size differential can be utilized in an apparatus adapted only to make vessel openings.

FIG. 17A is a perspective view of an externally positioned anastomosis fenestra cutting apparatus 1000 having an anvil 1210 ready for insertion through an insertion opening 16 into the lumen of a blood vessel. FIG. 17B is a perspective view of cutting apparatus 1000 distending vessel 20 and being readied for cutting. FIG. 17C shows the formation of an opening 25 as cylindrical cutting edge 1414 engages spherical engaging end 1212.

Cutting apparatus 1000' is shown in FIGS. 18A–18B with an elliptical anvil 1210' adapted to form elliptical openings in vessel 20 with elliptical cutting device 1400'. Note that FIG. 18A shows cutting apparatus 1000' distending the wall of vessel at angle so that the elliptical opening formed by a cutting apparatus 1000' is properly oriented for a Y-type end-to-side anastomosis. Cutting apparatus 1000' is a simple device that has a stationary cutter that cuts the blood vessel when the anvil is pulled against the cutter. Note that while anvil and anvil pull are shown as being integral, the anvil of the cutting apparatus may also be an expandable anvil such as those discussed in the section entitled Anvils.

Figures 19A, 19B:
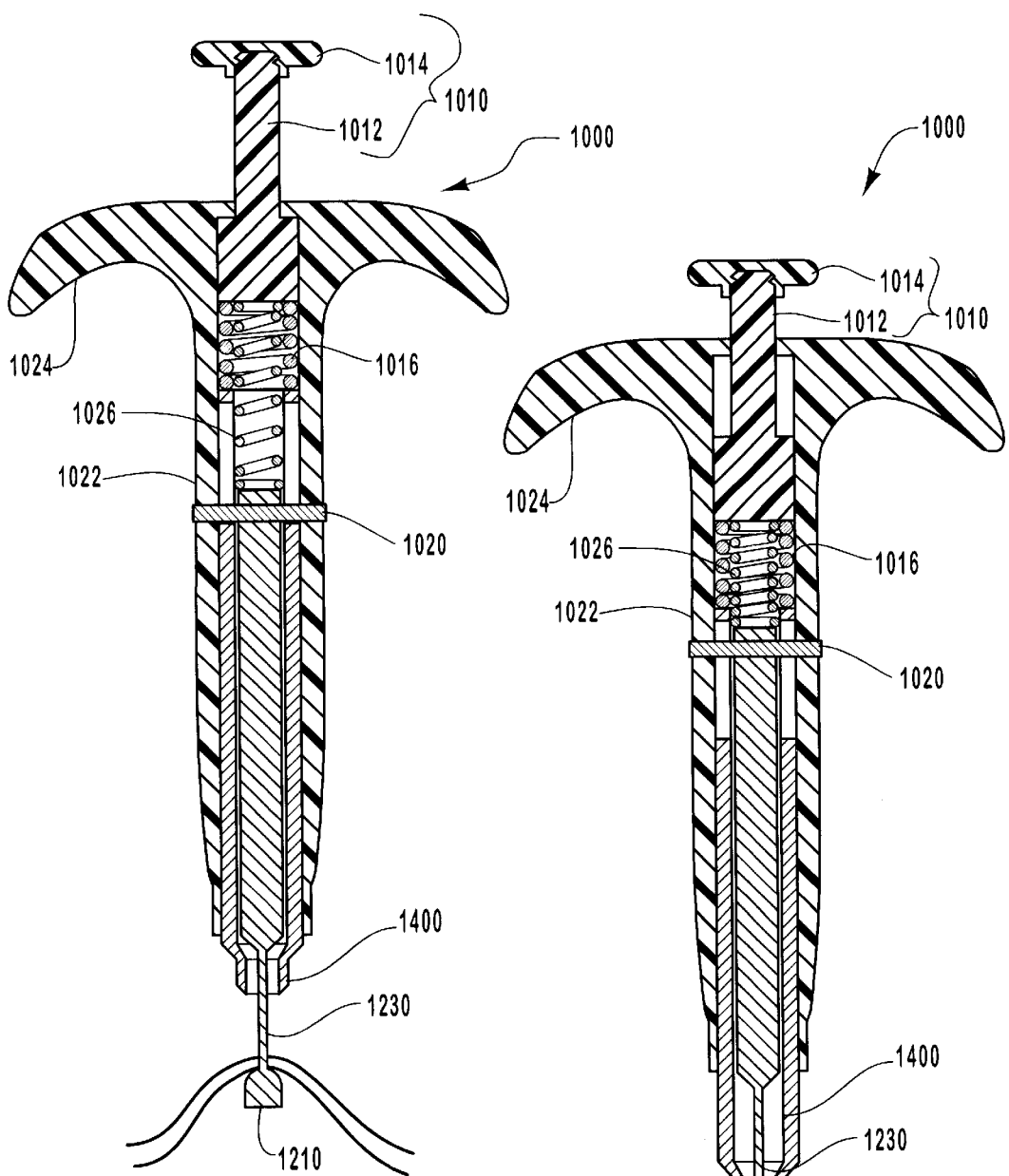
FIG. 19A is a cross-sectional view of a spring biased externally positioned anastomosis fenestra cutting apparatus after the anvil has been inserted through an insertion opening.
FIG. 19B is a cross-sectional view of the spring biased externally positioned anastomosis fenestra cutting apparatus shown in FIG. 19A as the anvil pull is pulled against the cutter.

FIGS. 19A–19B provide a cross-sectional views of cutting apparatus 1000 which reveal that it is spring biased. Spring biased cutting apparatus 1000 has a handle 1010 that includes a stem 1012 and a handle cap 1014. Stem 1012 travels within a chamber as shown by comparing FIGS.19A–19B to push against a high tension spring 1016 that pushes against a cutter 1400. While cutter 1400 is movable, anvil pull 1230 moves a greater distance in order to contact cutter 1400.

A pin 1020 extends through anvil pull 1230 and casing 1022 such that movement of grasping handle 1024, which is an integral component of casing 1022, also moves anvil pull 1230. Pin 1020 travels within a groove 1018 as shown in phantom lines in FIGS. 17A–17B. The distal end of anvil pull 1230 abuts a low tension spring 1026 concentrically positioned within high tension spring 1016. This configuration enables anvil pull 1230 and cutter 1400 to both be spring biased.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for forming an opening in a vessel comprising the steps of identifying an anastomosis site in a first vessel, forming an insertion opening in a wall of the first vessel at the anastomosis site, inserting an anvil means for engaging an interior surface of a wall of a first vessel at the anastomosis site, wherein the anvil means is inserted through the insertion opening into a lumen of the first vessel, wherein the anvil means has an engaging end, and wherein the engaging end is convex, positioning the engaging end of the anvil means against an interior surface of the wall of the first vessel, wherein the positioning is achieved through the insertion opening, and creating a first vessel opening in the wall of the fist vessel at the anastomosis site through the interaction of the engaging end of the anvil means with the cutting means for forming a first vessel opening in the wall of the first vessel at the anastomosis site, wherein the cutting means has a cutting perimeter that defines the shape of the first vessel opening, and wherein the cross-sectional area defined by the cutting perimeter is smaller than a cross-sectional area of the engaging end of the anvil means such that portions of the engaging end of the anvil means extend beyond the cutting perimeter when the cutting means engages the anvil means and creates the first vessel opening.

2. A method as recited in claim 1, wherein the anvil means is inserted into the lumen of the first vessel simultaneously as the engaging end of the anvil means is positioned against the interior surface of the wall of the first vessel.

3. A method as recited in claim 1, wherein the engaging end of the anvil means is positioned against the interior surface of the wall of the first vessel by manipulating an anvil pull extending from the engaging end of the anvil means through the insertion opening of the first vessel.

4. A method as recited in claim 3, wherein the anvil pull is manipulated via an anvil pull engager holding the anvil pull.

5. A method as recited in claim 1, wherein the cutting means includes a cutting tube that terminates at a cutting knife with a cutting edge and wherein the first vessel opening is created by bringing the cutting edge and the engaging end of the anvil means together with sufficient force to cut through the first vessel.

6. A method as recited in claim 5, wherein the cutting edge and the anvil means are brought together with sufficient force to cut through the first vessel and create a first vessel opening at the anastomosis site by puffing an anvil pull extending from the engaging end of the anvil means through the insertion opening of the first vessel as the cutting edge is pushed against the engaging end of the anvil means.

7. A method as recited in claim 5, wherein the engaging end of the anvil means is spherical, and wherein the cutting edge is circular such that the first vessel opening is formed as the circular cutting edge and the spherical engaging end are brought together.

8. A method as recited in claim 5, wherein the cutting edge is noncircular, and wherein the engaging end of the anvil means has a shape corresponding to that of the cutting; edge such that the fist vessel opening is formed as the noncircular cutting edge and the engaging end are brought together.

9. A method as recited in claim 1, wherein the anvil means is an expandable anvil such that the anvil has an initial collapsed position for insertion into the insertion opening and an expanded position, wherein the engaging end has a greater cross-sectional area than the cross-sectional area defined by cutting perimeter of the cutting means when in the expanded position.

10. A method as recited in claim 1, wherein the anvil means is rigid.

11. A method as recited in claim 1, wherein the anvil means is solid.

12. A method as recited in claim 1, further comprising the step of providing spring tension against the cutting means as the cutting means engages the anvil.

13. A method as recited in claim 1, wherein the engaging end of the anvil mean is adapted to engage an area of the interior surface of the wall of the first vessel which is greater than the cross-sectional area defined by the cutting means.

14. A method as recited in claim 1, wherein the cross-sectional area of the engaging end of the anvil means combined with the shape of the engaging end enables the first vessel opening to be created at any position in which the cutting means is initially set against the engaging end.

15. A method for forming an opening in a vessel comprising the steps of identifying an anastomosis site in a first vessel, forming an insertion opening in a wall of the first vessel at the anastomosis site, inserting an anvil having an engaging end though the insertion opening into a lumen of the first vessel, wherein the engaging end is convex, positioning the engaging end of the anvil against an interior surface of the wall of the first vessel via an anvil pull extending from the engaging end of the anvil, wherein the positioning is achieved through the insertion opening, and creating a first vessel opening in the wall of the first vessel at the anastomosis site by bringing the engaging end of the anvil and a cutting edge of a cutting knife together with sufficient force to cut through the first vessel, wherein the cutting edge has a cutting perimeter that defines the shape of the first vessel opening, and wherein the cross-sectional area defined by the cutting perimeter is smaller than a cross-sectional area of the engaging end of the anvil such that portions of the engaging end of the anvil extend beyond the cutting perimeter when the cutting edge and the engaging end are brought together to create the first vessel opening.

16. A method as recited in claim 15, wherein the anvil is inserted into the lumen of the first vessel simultaneously as the engaging end of the anvil is positioned against the interior surface of the wall of the first vessel.

17. A method as recited in claim 15, wherein the anvil pull is manipulated via an anvil pull engager holding the anvil pull.

18. A method as recited in claim 15, wherein the cutting edge and the anvil are brought together with sufficient force to cut through the first vessel and create a first vessel opening at the anastomosis site by pulling the anvil pull extending from the engaging end of the anvil through the insertion opening of the first vessel as the cutting edge is pushed against the engaging end of tube anvil.

19. A method as recited in claim 15, wherein the cutting knife is at an end of a cutting tube.

20. A method as recited in claim 15, wherein the engaging end of the anvil is spherical, and wherein the cutting edge is circular such that the first vessel opening is formed as the circular cutting edge and the spherical engaging end are brought together.

21. A method as recited in claim 15, wherein the cutting edge is noncircular, and wherein the engaging end of the anvil has a shape corresponding to that of the cutting edge such that the first vessel opening is formed as the noncircular cutting edge and the engaging end are brought together.

22. A method as recited in claim 15, wherein the anvil is an expandable anvil such that the anvil has an initial collapsed position for insertion into the insertion opening and an expanded position, wherein the engaging end has a greater cross-sectional area than the cross-sectional area defined by cutting perimeter of the cutting edge when in the expanded position.

23. A method as recited in claim 15, wherein the anvil is rigid.

24. A method as recited in claim 15, wherein the anvil is solid.

25. A method as recited in claim 15, wherein the cutting knife is at an end of a cutting tube, and further comprising the step of providing spring tension against the cutting tube as the cutting edge and the engaging end of the anvil are brought together.

26. A method as recited in claim 15, wherein the engaging end of the anvil is adapted to engage an area of the interior surface of the wall of the first vessel which is greater than the cross-sectional area defined by the cutting edge.

27. A method as recited in claim 15, wherein the cross-sectional area of the engaging end of the anvil combined with the shape of the engaging end enables the first vessel opening to be created at any position in which the cutting edge is initially set against the engaging end.

28. A method for forming an opening in a vessel comprising the steps of
   identifying an anastomosis site in a first vessel,
   forming an insertion opening in a wall of the first vessel at the anastomosis site,
   inserting an anvil having an engaging end through the insertion opening into a lumen of the first vessel, wherein the engaging end is convex,
   positioning the engaging end of the anvil against an interior surface of the wall of the first vessel via an anvil pull extending form the engaging end of the anvil, wherein the positioning is achieved through the insertion opening, and
   creating a first vessel opening in the wall of the first vessel at the anastomosis site by bringing the engaging end of the anvil and a cutting edge of a cutting knife at an end of a cutting tube together with sufficient force to cut through the first vessel,
      wherein the cutting edge has a cutting perimeter that defines the shape of the first vessel opening,
      wherein the cross-sectional area defined by the cutting perimeter is smaller than a cross-sectional area of the engaging engaging of the anvil such that portions of the engaging end of the anvil extend beyond the cutting perimeter when the cutting edge and the engaging end are brought together to create the first vessel opening, and
      wherein the engaging end of the anvil is adapted to engage an area of the interior surface of the wall of the first vessel which is greater than the cross-sectional area defined by the cutting edge.

29. A method as recited in claim 28, wherein the anvil pull is manipulated via an anvil pull engager holding the anvil pull.

30. A method as recited in claim 28, wherein the engaging end of the anvil is spherical, and wherein the cutting edge is circular such that the first vessel opening is formed as the circular cutting edge and me spherical engaging end are brought together.

31. A method as recited in claim 28, wherein the cutting edge is noncircular, and wherein the engaging end of the anvil has a shape corresponding to that of the cutting edge such that the first vessel opening is formed as the noncircular cutting edge and the engaging end are brought together.

32. A method as recited in claim 28, wherein the anvil is an expandable anvil such that the anvil has an initial collapsed position for insertion into the insertion opening and an expanded position, wherein the engaging end has a greater cross-sectional area than the cross-sectional area defined by cutting perimeter of the cutting edge when in the expanded position.

33. A method as recited in claim 28, wherein the anvil is rigid.

34. A method as recited in claim 28, wherein the cross-sectional area of the engaging end of the anvil combined with the shape of the engaging end enables the first vessel opening to be created at any position in which the cutting edge is initially set against the engaging end.

35. A method for forming an opening in a vessel comprising the steps of
   identifying an anastomosis site in a first vessel;
   forming an insertion opening in a wall of the first vessel at the anastomosis site,
   inserting an anvil having an engaging end through the insertion opening into a lumen of the first vessel, wherein the engaging end is convex and spherical,
   positioning the engaging end of the anvil against an interior surface of the wall of the first vessel via an anvil pull extending from the engaging end of the anvil, wherein the positioning is achieved through the insertion opening, and
   creating a first vessel opening in the wall of the first vessel at the anastomosis site by bringing the engaging end of the anvil and a circular cutting edge of a cutting knife at an end of a cutting tube together with sufficient force to cut through the first vessel,
      wherein the cutting edge has a cutting perimeter that defines the shape of the first vessel opening, and
      wherein the cross-sectional area defined by the cutting perimeter is smaller than a cross-sectional area of the engaging end of the anvil such that portions of the engaging end of the anvil extend beyond the cutting perimeter when the cutting edge and the engaging end are brought together to create the fist vessel opening.

36. A method as recited in claim 35, wherein the anvil pull is manipulated via an anvil pull engager holding the anvil pull.

37. A method as recited in claim 35, wherein the anvil is an expandable anvil such that the anvil has an initial collapsed position for insertion into the insertion opening and an expanded position, wherein the engaging end has a greater cross-sectional area than the cross-sectional area defined by cutting perimeter of the cutting edge when in the expanded position.

38. A method as recited in claim 35, wherein the anvil is rigid.

39. A method as recited in claim 35, wherein the cross-sectional area of the engaging end of the anvil combined with the shape of the engaging end enables the first vessel opening to be created at any position in which the cutting edge is initially set against the engaging end.

40. A method as recited in claim 35, wherein the engaging end of the anvil is adapted to engage an area of the interior surface of the wall of the first vessel which is greater than the cross-sectional area defined by the cutting edge.

* * * * *

UNITED STATES PATENT AND TRADEMARK OFFICE
CERTIFICATE OF CORRECTION

PATENT NO. : 6,551,334 B2  
APPLICATION NO. : 09/736781  
DATED : April 22, 2003  
INVENTOR(S) : Duane D. Blatter et al.

It is certified that error appears in the above-identified patent and that said Letters Patent is hereby corrected as shown below:

The titled is incorrect. It should read, --EXTERNALLY DIRECTED METHODS FOR FORMING AN ANASTOMOSIS OPENING IN A VESSEL--

Column 6, line 7 reads, "needle-and-suture-radiated . . ." which should read --needle-and-suture-mediated . . .--

Column 7, line 23 reads, "nonpenetrated intiral . . ." which should read --nonpenetrated intimal . . .--

Column 7, line 32 reads, "Nonpenetrating Stapling:" which should be in italics.

Column 9, line 31 reads, "and Uttan IC . . ." which should read --Uttam K. . . .--

Column 9, line 55 reads, "fibrinogen solution to and thrombin . ." which should read --fibrinogen solution and thrombin . . .--

Column 17, line 54 reads, "will become more filly . . ." which should read --will become more fully . . .--

Column 54, line 63 reads, "the engaging end of tube . ." which should read --the engaging end of the . . .--

Signed and Sealed this

Eighth Day of April, 2008

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 6,551,334 B2 |
| APPLICATION NO. | : 09/736781 |
| DATED | : April 22, 2003 |
| INVENTOR(S) | : Duane D. Blatter et al. |

It is certified that error appears in the above-identified patent and that said Letters Patent is hereby corrected as shown below:

Item [54] and column 1, lines 1-4 should read, --EXTERNALLY DIRECTED METHODS FOR FORMING AN ANASTOMOSIS OPENING IN A VESSEL--

Column 6, line 7 reads, "needle-and-suture-radiated . . ." which should read --needle-and-suture-mediated . . .--

Column 7, line 23 reads, "nonpenetrated intiral . . ." which should read --nonpenetrated intimal . . .--

Column 7, line 32 reads, "Nonpenetrating Stapling:" which should be in italics.

Column 9, line 31 reads, "and Uttan IC . . ." which should read --Uttam K. . . .--

Column 9, line 55 reads, "fibrinogen solution to and thrombin . ." which should read --fibrinogen solution and thrombin . . .--

Column 17, line 54 reads, "will become more filly . . ." which should read --will become more fully . . .--

Column 54, line 63 reads, "the engaging end of tube . ." which should read --the engaging end of the . . .--

This certificate supersedes the Certificate of Correction issued April 8, 2008.

Signed and Sealed this

Sixth Day of May, 2008

JON W. DUDAS
*Director of the United States Patent and Trademark Office*